(12) United States Patent
Roberts

(10) Patent No.: US 6,197,517 B1
(45) Date of Patent: Mar. 6, 2001

(54) ESSENTIAL GENES OF YEAST AS TARGETS FOR ANTIFUNGAL AGENTS, HERBICIDES, INSECTICIDES AND ANTI-PROLIFERATIVE DRUGS

(75) Inventor: Christopher J. Roberts, Seattle, WA (US)

(73) Assignee: Rosetta Inpharmatics, Inc., Kirkland, WA (US)

( * ) Notice: Subject to any disclaimer, the term of this patent is extended or adjusted under 35 U.S.C. 154(b) by 0 days.

(21) Appl. No.: 09/315,794

(22) Filed: May 21, 1999

(51) Int. Cl.$^7$ ............................ C12Q 1/68; C12N 15/00; C12N 1/15; C12N 15/11; C07H 21/04

(52) U.S. Cl. ..................... 435/6; 435/69.1; 435/91.1; 435/254.1; 435/254.11; 435/254.2; 435/254.21; 536/23.1; 536/23.7; 536/23.74; 536/24.3

(58) Field of Search ........................ 435/6, 69.1, 91.1, 435/254.1, 254.11, 254.2, 254.21; 536/23.1, 23.7, 23.74, 24.3

(56) References Cited

U.S. PATENT DOCUMENTS

| | | |
|---|---|---|
| 4,816,567 | 3/1989 | Cabilly et al. . |
| 5,091,513 | 2/1992 | Huston et al. . |
| 5,223,408 | 6/1993 | Goeddel et al. . |
| 5,225,538 | 7/1993 | Capon et al. . |
| 5,359,046 | 10/1994 | Capon et al. . |
| 5,569,588 | 10/1996 | Ashby et al. . |
| 5,587,458 | 12/1996 | King et al. . |
| 5,608,039 | 3/1997 | Pastan et al. . |
| 5,668,255 | 9/1997 | Murphy . |
| 5,777,085 | 7/1998 | Co et al. . |
| 5,777,888 | 7/1998 | Rine et al. . |
| 5,783,398 | 7/1998 | Marcy et al. . |
| 5,789,554 | 8/1998 | Leung et al. . |
| 5,821,047 | 10/1998 | Garrard et al. . |

FOREIGN PATENT DOCUMENTS

| | | |
|---|---|---|
| WO 97/10365 | 3/1997 | (WO) . |
| WO 98/38329 | 9/1998 | (WO) . |

OTHER PUBLICATIONS

Murakami et al., Nature Genet 10, 261–268 (Jul. 1995).*
Volckaert et al., Yeast 13 (3), 251–259 (1997).*
Garcia–Cantalejo et al., Yeast 10 (2), 231–245 (1994).*
Zuniga et al., Gene 233, 141–150 (Jun. 11, 1999).*
Pohl et al., Genbank, Accession No. Z28296 Y13137, May 9, 1994.*
Pohl et al., Genbank, Accession No. Z28304, Y13137, May 9, 1994.*
Agrawal and Iyer, 1997, "Perspectives in Antisense Therapeutics", Pharamcol. Ther. 76:151–160.
Altschul et al., 1997, "Gapped Blast and PSI–Blast: A New Generation of Protein Database Search Programs", Nucl. Acids Res. 25:3389–3402.

Atkins et al., 1994, "Antisense Gene Expression in Yeast", Biol. Chem. Hoppe–Seyler 375:721–729.
Brachmann et al., 1998, "Designer Deletion Strains Derived from *Saccharomyces cerevisiae* S288C: A Useful Set of Strains and Plasmids for PCR–Mediated Gene Disruption and Other Applications", Yeast 14:115–132.
Burbaum and Sigal, 1997, "New Technologies for High–Throughput Screening", Curr. Opin. Chem. Biol. 1:72–78.
Castanotto et al., 1998, "Structural Similarities Between Hammerhead Ribozymes and the Spliceosomal RNAs Could Be Responsible for Lack of Ribozyme Cleavage in Yeast", Antisense & Nucl. Acid Drug Devel. 8:1–13.
Chien et al., 1991, "The Two–Hybrid System: A Method to Identify and Clone Genes for Proteins that Interact with a Protein of Interest", Proc. Natl. Acad. Sci. USA 88:9578–9582.
Clackson, 1998, "Redesigning Small Molecule–Protein Interfaces", Curr. Opin. Structural Biol. 8:451–458.
Crooke, 1998, "Antisense Therapeutics", Biotechnol. & Genetic Engineering Rev. 15:121–157.
Cunningham and Wells, 1997, "Minimized Proteins", Curr. Opin. Structural Biol. 7:457–462.
Eckstein, 1997, "Exogenous Application of Ribozymes for Inhibiting Gene Expression", in: *Oligonucleotides as Therapeutic Agents*. Ciba Foundation Symposium 209, John Wiley & Sons, Chichester, England, pp. 207–217.
Garfinkel et al., 1998, "Ty Mutagenesis", Meth. Microbiol. 26:101–117.
Godowski et al., 1988, "Signal Transduction and Transcriptional Regulation by Glucocorticoid Receptor–LexA Fusion Proteins", Science 241:812–816.
Goffeau et al., 1996, "Life with 6000 Genes", Science 274:546–567.
Hubbard, 1997, "Can Drugs be Designed?", Curr. Opin. Biotechnol. 8:696–700.

(List continued on next page.)

Primary Examiner—Remy Yucel
Assistant Examiner—Mark L. Shibuya
(74) Attorney, Agent, or Firm—Pennie & Edmonds LLP

(57) ABSTRACT

The present invention relates to genes in *Saccharomyces cerevisiae* which are essential for germination and proliferation of *S. cerevisiae* and using the identified genes or their encoded proteins as targets for highly specific antifungal agents, insecticides, herbicides and anti-proliferation drugs. The present invention provides antisense molecules and ribozymes comprising sequences complementary to the sequences of mRNAs of essential genes that function to inhibit the essential genes. The present invention also provides neutralizing antibodies to proteins encoded by essential genes that bind to and inactivate the essential gene products. The present invention further provides pharmaceutical compositions for treating fungal and proliferative diseases, as well as methods of treatment of fungal and proliferative diseases.

15 Claims, 37 Drawing Sheets

OTHER PUBLICATIONS

Huse et al., 1989, "Generation of a Large Combinatorial Library of the Immunoglobulin Repertoire in Phage Lambda", Science 246:1275–1281.

Ito et al., 1983, "Transformation of Intact Yeast Cells Treated with Alkali Cations", J. Bacteriol. 153:163–168.

Johnson et al., 1992, "Ubiquitin as a Degradation Signal", EMBO J. 11:497–505.

Kanehisa, 1984, "Use of Statistical Criteria for Screening Potential Homologies in Nucleic Acid Sequences", Nucl. Acid Res. 12:203–213.

Kleinberg and Wanke, 1995, "New Approaches and Technologies in Drug Design and Discovery", Am. J. Health Syst. Pharm. 52:1323–1336.

Kubinyi, 1995, "Strategies and Recent Technologies in Drug Discovery", Pharmazie 50:647–662.

Lavrovsky et al., 1997, "Therapeutic Potential and Mechanism of Action of Oligonucleotides and Ribozymes", Biochem. & Mol. Med. 62:11–22.

Mattos and Ringe, 1996, "Locating and Characterizing Binding Sites on Proteins", Nature Biotechnol. 14:595–599.

Merrifield and Stewart, 1965, "Automated Peptide Synthesis", Nature 207:522–523.

Mewes et al., 1997, "Overview of the Yeast Genome", Nature 387(Supp.):7–65.

Nasr et al., 1995, "Artificial Antisense RNA Regulation of YBR1012(YBR136w), an Essential Gene from *Saccharomyces cerevisiae* which Is Important for Progression through G1/S", Mol. Gen. Genet. 249:51–57.

Olsson et al., 1997, "Silencing MIG1 in *Saccharomyces cerevisiae*: Effects of Antisense MIG1 Expression and MIG1 Gene Disruption", Appl. Environ. Microbiol. 63:2366–2371.

Pearson, 1990, "Rapid and Sensitive Sequence Comparison with FASTP and FASTA", Meth. Enzymol. 183:63–98.

Pearson, 1994, "Using the FASTA Program to Search Protein and DNA Sequence Databases", Meth. Mol. Biol. 24:307–331.

Rothstein, 1991, "Targeting, Disruption, Replacement, and Allele Rescue: Integrative DNA Transformation in Yeast", Meth. Enzymol. 194:281–301.

Schiestl and Gietz, 1989, "High Efficiency Transformation of Intact Yeast Cells Using Single Stranded Nucleic Acids as a Carrier", Curr. Genet. 16:339–346.

Schullek et al., 1997, "A High–Density Screening Format for Encoded Combinatorial Libraries: Assay Miniaturization and Its Application to Enzymatic Reactions", Anal. Biochem. 246:20–29.

Sherman, 1991, "Getting Started with Yeast", Meth. Enzymol. 194:3–21.

Sherman and Wakem, 1991, "Mapping Yeast Genes", Meth. Enzymol. 194:38–57.

Stark, 1998, "Studying Essential Genes: Generating and Using Promoter Fusions and Conditional Alleles", Meth. Microbiol. 26:83–99.

Vaughan et al., 1996, "Human Antibodies with Sub–Nanomolar Affinities Isolated from a Large Non–Immunized Phage Display Library", Nature Biotechnol. 14:309–314.

Wach et al., 1994, "New Heterologous Modules for Classical or PCR–Based Gene Disruptions in *Saccharomyces cerevisiae*", Yeast 10:1793–1808.

Ward et al., 1989, "Binding Activities of a Repertoire of Single Immunoglobulin Variable Domains Secreted from *Escherichia coli*", Nature 341:544–546.

Zhao and Lemke, 1998, "Rules for Ribozymes", Mol. Cell. Neurosci. 11:92–97.

* cited by examiner

YFR003C on chromosome VI from coordinates 153118 to 152651.

UPTAG primer:
ATTAAGTCTATAAGGATGGATGTCCACGAGGTCTCTATCGAACCAGCATTGCAGAGCGTA
CGCTGCAGGTCGAC DOWNTAG primer:
TCGTTGTACAAAGCCTCACGGTGTCGGTCTCGTAGTACTTCGTAAGAGGCTTGAGATCGA
TGAATTCGAGCTCG Upstream45 primer:
TGCCAGGAGTTGCGAGCTAAGTCTTCAATTAAGTCTATAAGGATG Downstream45 primer:
TTGCTGCTTCATCGAATATTTTGGCTTTCGTTGTACAAAGCCTCA A primer: CCTCTTAATTGTGTTATCACCTGCT B primer: CATGTTTTCATTGTCAATCACATTT C primer: GAACGTAGACAAAGAAGATTGGAAA D primer: TCTGCTAGAAAGAAAGCACAAGATT KanB1 primer: TGTACGGGCGACAGTCACAT KanC3 primer: CCTCGACATCATCTGCCCAGAT

FIG.3 yfr003C

```
  1 ATGAGTGGAA ATCAAATGGC TATGGGATCA GAACAACAAC AGACCGTAGG
 51 GTCCCGAACG GTGAGTGTGG AAGAGGTTCC CGCAGTTTTG CAGCTTCGAG
101 CAACTCAAGA TCCTCCAAGA AGCCAGGAGG CAATGCCTAC AAGGCACAAT
151 GTAAGATGGG AAGAAAATGT GATTGACAAT GAAAACATGA ATAAAAAAAA
201 GACCAAGATA TGCTGCATTT TTCATCCACA AAATGAGGAT GAAGAAGAGT
251 GCAACCATCA TTCAGATGAT GATGGATCCT CTTCTTCCGG ATCCTCTTCT
301 TCAGAATCTG AGAATGAGAA GGATCTTGAC TTTAACGAAC GTAGACAAAG
351 AAGATTGGAA AGGCGCCATC GTAAACTTGA GAAAAAAAGG TCATATAGCC
401 CCAATGCTTA TGAAATCCAA CCAGATTATT CTGAATACAG GCGAAAACAG
451 CAGGAAAAGA AGGACTGA
```

FIG.4 yfr003cp

```
  1 MSGNQMAMGS EQQQTVGSRT VSVEEVPAVL QLRATQDPPR SQEAMPTRHN
 51 VRWEENVIDN ENMNKKKTKI CCIFHPQNED EEECNHHSDD DGSSSSGSSS
101 SESENEKDLD FNERRQRRLE RRHRKLEKKR SYSPNAYEIQ PDYSEYRRKQ
151 QEKKD
```

FIG.5 yfr003c blastp   nr   results

```
                                                                            Score    E
Sequences producing significant alignments:                                 (bits) Value
sp|P43587|YFH3_YEAST HYPOTHETICAL 18.2 KD PROTEIN IN NIC96-MPR1...            247   4e-65
sp|O14218|YDTD_SCHPO HYPOTHETICAL 11.7 KD PROTEIN IN C6B12.13 IN C...          53   7e-07
emb|CAB05783|   (z83236) K10K10.7 (Caenorhabditis elegans).                   43   8e-04
sp|Q09384|YS88_CAEEL HYPOTHETICAL 12.3 KD PROTEIN 2K945.8 IN CM...             39   0.016
gi|3176438  (U53588) HCG V (Homo sapiens)                                     39   0.021
sp|P06916| FIRA_PLAFF  300 KD ANTIGEN AG231 >gi|72398|pir| |YAZQ31
pir||A54641  interspersed repeat antigen precursor - Plasmodium...            32   1.6
gi|3551821  (AF058803) mucin 4 (Homo sapiens)                                 32   1.6
emb|CAA03985|   (AJ000281) mucin (Homo sapiens)                               30   7.8
                                                                              30   7.8
```

FIG.6 yfr003c blast results vs. C. elegans from Yeast Protein
Database, Proteome, Inc.

Report generated 04 May 1999, 10:27 AM
BLAST Alignments for YPR003C vs. C. elegans HITS
C07H6.2 K10H10.7 ZK947.8 3

Query Results for: YFR003C Protein of unknown function (Length = 155)
Gene GenBank Synonyms/Description Match
Length & Iden & Sim High
Score E Val
C07h6.2 C07H6.2 No Description 104 33% 45% 127 4e-06
K10H10.7 3878543 K10H10.7 No Description 124 27% 42% 119 7e-05
IK945.8 3881892 IK945.8 No Description 92 28% 42% 98 6e-05

C07H6.2 No Description
Score = 127 Length = 107 Expect = 4e-06
Identities = 34/104 (33%0 Similarities =47/104 (45%0 Gaps = 7/104 (7%)

```
|---*******************************************.........................|

Query    6 MGSEQQQTVGSRTVSVEEVPAVLQ--LRATQDPPRSQEAMPTRHNVRWEENVIDNENMNK 65
           M   QQT  S   S  VP  + L      P +Q +   R +V W    +DNE M  K
Sbjct    1 MSHTQQQTASSTETSTVTVPPSREQNLVLHLSPNPAQPSTSERRHVVWATETVDNEGNGK 60

Query   66 KKTKICCIF-HPQNEDEEECNHHSDDDGSSSSGSSSSESENEKD 108
           KK+K CCI+  P+N  +      SD D  +G      E++K+
Sbjct   61 KKSKCCCIYKKPKNWQDSS----SDSDSDCETGHCRGHVEHKKN 100
```

K10H10.7 Description
Score = 119 Length = 132 Expect = 7e-05
Identities = 34/124 (27%) Similarities = 52/124 (42%) Gaps = 31/124 (25%)

```
|---*******************************************.........................|

Query    6 MAMGSEQQQTVGSRTVSVEEVPA--VLQLRATQDPPRSQEAMPTRHNVRWEENVIDNENM 63
           MA  +    T+ ++    EEV    VL+LRA   PP           +V W E V+DNE+M
Sbjct    1 MAQSNTTTTTLVVKSEDQEEVQEEHVLRLRAPPSPP----------HVTWAEGVVDNEHM 50

Query   64 NKKKTKICCIF------------HPQNEDEEECNHHS-------DDDGSSSSGSSSSESE 104
           + K+  CCI+              P    + E C  H+       +DG      + E++
Sbjct   51 GRLKSNCCCIYVAPRQWDDPSTWEPNEYETEHCRGHTLPERKKKKEDGGDEGDDENKENK 110

Query  105 NEKD 106
           + KD
Sbjct  111 DNKD 114
```
LK945.8 No Description
Score = 98 Length = 109 Expect = 6e-05
Identities - 26/92 (28%) Similarities = 39/92 (42%) Gaps = 23/92 (25%)

```
|-----------*****************************************.................|

Query   29 VLQLRATQDPPRSQEAMPTRHNVRWEENVIDNENMNKKKTKICCIF-----------HP 76
           VL+LRA  + PR            V W   VIDNE+M  + K+ CCI+              P
Sbjct   20 VLRLRAPVERPR---------VTWGAGVIDNEHMGRLKSNCCCIYTPPRVWDDPSTWEP 69

Query   77 QNEDEEECHHHS-DDDGSSSSGSSSSESENEK 107
           +  +E C H+ +     G   S+  +   +K
Sbjct   70 EEHETEHCRGHTLPEKKQKPQGGHGSDKDEDK 101
```

FIG.7 yfr003c blast results vs. C. albicans from Yeast Protein Database, Proteome, Inc Report generated 04 May 1999, 10:35 AM
Blast Alignment for YFR003C vs. C. albicans fragments HITS
Oop-F1-F2A4-Forward 384019E09.sl.seq.2

Query Results for: YFR003C Protein of unknown function (length = 155)
Compared with C. albicans fragments protein sequences (Documentation)
Gene Genbank Synonyms/Descriptions Match
Length % Iden % Sim High
Score E Val
Unp-F1F2A4-Forward Unp-F1-F2A4-Forward (-) Assignments:YFR3 66 48% 67% 185 1e-08
384019E09.sl.seq  384019E06.sl.seq No Description 19 63% 84% 33 0.006

Unp-F1-F2A4-Forward (-) Assignment:YFR3
Score = 185  Length = 257  Expect = 1e-08  Frame = +1
Identities = 32/66 (48%) Similarities = 44/66 (67%) Gaps = 2/66 (3%)

```
|--------***********************************........................|

Query  18  SRTVSVEEVPAVLQLRATQQPPRSQEAMPTRHNVRWEENVIDNENMNKKKTKICCIFHP-  76
           S+T +      P +L+LRA +   R        +V W+ NV+DNE++NKKKTKICCIFHP
Sbjct  51  SQTTTTTASP-ILKLRAQERQAR---------DVSWDANVVDNEHLNKKKTKICCIFHPS  100

Query  77  -QNEDEEE  83
           +N DEE+
Sbjct  101 DRNCDEED  106
```

384019E09.sl.seq No Description
Score = 33  Length = 100  Expect = 0.006  Frame = +2
Identities =12/19 (63%) Similarities =16/19  (84%)

```
|-----------------------**********...................|

Query 65   KKKTKICCIFHPQNEDEEE 03
           +++TKICCIFHPQ   +EE
Sbjct 10   QEETKICCIFHPQRSFDEE 28
```

FIG.8

Sequences producing significant alignments :

| | | Score (BITS) | E Value |
|---|---|---|---|
| sp|P10614|CP51_YEAST | CYTOCHROME P450 LI (14DM) (LANOSTEROL 14-A... | 1095 | 0.0 |
| sp|P50859|CP51_CANGA | CYTOCHROME P450 LI (14DM) (LANOSTEROL 14-A... | 929 | 0.0 |
| sp|P14263|CP51_CANTR | CYTOCHROME P450 LI (P450-L1A1) (LANOSTEROL... | 707 | 0.0 |
| sp|P10613|CP51_CANAL | CYTOCHROME P450 LI (P450-L1A1) (LANOSTEROL... | 707 | 0.0 |
| sp|Q02315|CP51_ISSOR | CYTOCHROME P450 LI (P450-L1A1) (LANOSTEROL... | 553 | e-157 |
| sp|Q09736|CP51_SCHPO | PUTATIVE CYTOCHROME P450 LI (LANOSTEROL 14... | 491 | e-138 |
| sp|P49602|CP51_USTMA | CYTOCHROME P450 LI (14DM) (LANOSTEROL 14-A... | 469 | e-132 |
| sp|Q12664|CP51_PENIT | CYTOCHROME P450 LI (P450-L1A1) (EBURICOL 1... | 464 | e-130 |
| sp|Q16850|CP51_HUMAN | CYTOCHROME P450 LI (LANOSTEROL 14-ALPHA DE... | 318 | 2e-86 |
| sp|Q64654|CP51_RAT | CYTOCHROME P450 LI (LANOSTEROL 14-ALPHA DEME. | 315 | 1e-85 |
| sp|P22680|CP70_HUMAN | CYTOCHROME P450 VII (CHOLESTEROL 7-ALPHA-M... | 98 | 4e-20 |
| sp|P29980|CPXN_ANASP | PROBABLE CYTOCHROME P450 (ORF3) | 95 | 3e-19 |

FIG. 9 yfr003c

YGR277C on chromosome VII from coordinates 1046557 to 1045640.

UPTAG primer:
GTAAAGAAGTGTAAGATGGATGTCCACGAGGTCTCTATTGCAGACTACGGCCTACGCGTA
CGCTGCAGGTCGAC DOWNTAG primer:
TATACAAAAATATGTTTACGGTGTCGGTCTCGTAGATTGCATTGTAACCGCGCCGATCGA
TGAATTCGAGCTCG Upstream45 primer:
AGACGTGATTAAACCTAAAAATCTAAAGTAAAGAAGTGTAAGATG Downstream45 primer:
AAATAATAGTGAACTACAACAATAAAATATACAAAAATATGTTTA A primer: TTATCATTTCCCAGTTTTCTCTCTG B primer: TCAACAATATTTTATGTCCATCGTG C primer: CACTTTTGAAACTTGGAAGCTAGAG D primer: ACTTCCGATACCACATTTGTATGAT KanB1 primer: TGTACGGGCGACAGTCACAT KanC3 primer: CCTCGACATCATCTGCCCAGAT

FIG. 11 ygr277c

```
  1 ATGGTTGAGG AAAATTCCAG AGTTTTGATT GTTCTTCCTT ATACACCGCC
 51 TAGTGCTACT TTGCAGAGGA TTATAGGGCA AACTATTCCG TTCTTAAGAG
101 AATGTCAAAG TCAACTAGAC ATCGTGATTG TACCTGAATT CAAAACCTCA
151 TTCCAGTTGG ATTCTGCGCT AGGGAAGATG TACAGTATTA CCAGGGATGT
201 CCTTTTGGGC TATGGAATGA TCAACAGCGG AATCAACATC ATATTCAACA
251 ATATTCATTT CGTCGAGAGT AATTTGCAAT GGAAAGTGGT TTTATTGCCA
301 CAGGAATCCA CTTTTGAAAC TTGGAAGCTA GAGTTGGGAC AAGGACAATA
351 CCATAGTATA GAACATTATG CATTACACGA TAATATAATG GAAGAGATAG
401 AAGGTCCCAA AGATGCTAAC AAATTTCATG TCACCGCATT GGGCGGAACG
451 TTCGACCACA TTCACGATGG ACATAAAATA TTGTTGAGCG TCTCTACATT
501 CATCACGTCA CAAAGGTTAA TTTGTGGAAT TACGTGCGAT GAGCTCTTGC
551 AAAACAAGAA ATACAAAGAG TTGATTGAAC CTTATGATAC ACGATGCAGG
601 CACGTACATC AATTCATCAA GTTGTTAAAA CCGGATCTCT CCGTAGAACT
651 AGTTCCCTTA AGGGACGTGT GCGGCCCCAC AGGGAAAGTA CCCGAGATAG
701 AATGTTTAGT TGTGAGTAGA GAAACCGTCA GTGGGGCAGA GACTGTGAAT
751 AAGACTAGGA TTGAAAAAGG CATGAGCCCA TTGGCAGTAC ATGTGGTTAA
801 TGTACTTGGA GGAAGGGAGG AAGACGGCTG GAGCGAGAAG TTAAGCAGCA
851 CGGAAATCAG ACGCCTACTT AAGTCCTCTG CTTCGCCAAC GTGCACTCCA
901 CAAAACCCTT GCGTATAA
```

FIG. 12 ygr277cp

```
  1 MVEENSRVLI VLPYTPPSAT LQRIIGQTIP FLRECQSQLD IVIVPEFKTS
 51 FQLDSALGKM YSITRDVLLG YGMINSGINI IFNNIHFVES NLQWKVVLLP
101 QESTFETWKL ELGQGQYHSI EHYALHDNIM EEIEGPKDAN KFHVTALGGT
151 FDHIHDGHKI LLSVSTFITS QRLICGITCD ELLQNKKYKE LIEPYDTRCR
201 HWIQFIKLLK PDLSVELVPL RDVCGPTGKV PEIECLVVSR ETVSGAETVN
251 KTRIEKGMSP LAVHVVNVLG GREEDGWSEK LSSTEIRRLL KSSASPTCTP
301 QNPCV
```

FIG. 13

Sequences producing significant alignments:

|  | Score (bits) | E Value |
|---|---|---|
| sp\|PS3332\|YG5T_YEAST HYPOTHETICAL 34.3 KD PROTEIN IN TAF145-YOR... | 597 | e-170 |
| gb\|AAD15511\| (AC006439) hypothetical protein [Arabidopsis thali... | 116 | 2e-25 |
| sp\|Q10350\| YDA8_SCHPO HYPOTHETICAL 37.0 KD PROTEIN C1F12.08 IN C... | 107 | 1e-22 |
| dbj\|BAA29713\| (AP000003) 177aa long hypothetical protein [Pyroc... | 82 | 4e-15 |
| pir\|\|E64428 hypothetical protein MJ1030 - Methanococcus jannasc... | 70 | 2e-11 |
| gi\|2623029 (AE000941) conserved protein [Methanobacterium therm... | 69 | 4e-11 |
| gi\|2648319 (AE000953) conserved hypothetical protein [Archaeogl... | 61 | 8e-09 |

FIG.14 ygr277c

YGR278W on chromosome VII from coordinates 1046727 to 1048460.

UPTAG primer:
AGGCTACAAACCAGCATGGATGTCCACGAGGTCTCTAAGTACAGGTAATGCCTACGCGTA
CGCTGCAGGTCGAC DOWNTAG primer:
GTTTGGCCGGGCTCTTCACGGTGTCGGTCTCGTAGGCACAAATATAACGTCGCCGATCGA
TGAATTCGAGCTCG Upstream45 primer:
GAGTAAGAAACCTAAAAAGGAATAAAAAGGCTACAAACCAGCATG Downstream45 primer:
ATATGTACGATTACATGTGTAATGTTTGTTTGGCCGGGCTCTTCA A primer: AATGAGGTTTTGAATTCAGGTACAA B primer: TCTGGAATATCAGAATTTAGCAAGG C primer: ATTATTCAAGAAGTTGAGGATGCAG D primer: TATATCAAAGGACTGCTTTCTGGTT KanB1 primer: TGTACGGGCGACAGTCACAT KanC3 primer: CCTCGACATCATCTGCCCAGAT

FIG.16 ygr278.w.

```
   1  ATGTCTACCG CTACCATACA GGATGAAGAC ATTAAATTTC AGAGAGAAAA
  51  CTGGGAAATG ATAAGGTCAC ACGTTTCACC CATAATATCC AATTTAACAA
 101  TGGACAACTT ACAGGAATCG CACAGAGACT TATTTCAAGT CAATATACTT
 151  ATTGGCCGCA ACATAATTTG TAAAAATGTT GTGGATTTTA CTCTGAACAA
 201  ACAGAATGGC AGGCTAATCC CTGCTTTATC CGCTTTGATT GCCCTTGCAA
 251  ATTCTGATAT TCCAGATATT GGAGAAACTT TAGCAAAAGA ACTAATGTTA
 301  ATGTTCGTGC AGCAATTCAA TCGCAAAGAT TACGTGTCCT GCGGAAATAT
 351  CCTTCAATGT CTGTCCATTT TATTTCTTTA TGATGTAATT CATGAAATCG
 401  TGATCTTACA GATTCTATTG CTACTCCTTG AAAAGAATTC TTTACGACTG
 451  GTCATTGCCG TGATGAAAAT ATGTGGCTGG AAACTTGCAC TTGTCAGTAA
 501  GAAAACCCAT GATATGATTT GGGAGAAGTT AAGATATATT TTGCAAACAC
 551  AGGAGTTATC TAGTACACTA CGTGAGTCGT TAGAGACTCT GTTTGAAATA
 601  AGGCAAAAAG ATTATAAATC TGGGTCTCAA GGTCTGTTTA TATTGGACCC
 651  AACTAGTTAC ACAGTTCATA CGCACTCCTA TATTGTTAGT GATGAGGATG
 701  AAGCCAACAA AGAACTGGGA AATTTTGAAA AGTGTGAAAA TTTCAATGAA
 751  CTAACCATGG CGTTTGATAC GCTACGACAG AAGCTGCTGA TAAATAATAC
 801  GTCCGACACA AATGAAGGTA GTAACAGTCA ATTACAAATC TATGACATGA
 851  CATCTACCAA TGATGTCGAG TTTAAAAAGA AGATTTATTT GGTTCTGAAA
 901  AGTTCATTAT CAGGTGACGA AGCGGCTCAC AAAATTGCTAA AATTAAAGAT
 951  TGCGAACAAT TTGAAAAAAA GCGTGGTAGA TATAATCATC AAATCTAGTT
1001  TGCAGGAATC TACATTCTCT AAATTTTATT CTATTTTGTC CGAACGTATG
1051  ATAACGTTCC ACAGGAGTTG GCAGACAGCT TACAATGAAA CTTTTGAGCA
1101  GAATTATACA CAAGATATCG AAGATTATGA AACTGACCAA CTGCGAATCT
1151  TAGGTAAGTT TTGGGGACAC TTAATATCTT ATGAATTTCT TCCAATGGAC
1201  TGTCTTAAGA TAATTAAGTT AACTGAGGAA GAATCGTGTC CTCAAGGAAG
1251  AATTTTCATC AAATTTTTAT TTCAAGAGCT CGTAAATGAG CTCGGATTAG
1301  ATGAGCTGCA ATTAAGGCTA AACTCCAGCA AGCTTGACGG AATGTTTCCG
1351  CTGGAAGGAG ACGCCGAACA TATAAGATAC TCCATAAATT TCTTTACTGC
1401  CATAGGATTG GGCCTGCTCA CAGAGGACAT GAGAAGCCGG TTGACAATTA
1451  TTCAAGAAGT TGAGGATCCA GAGGAAGAAG AAAAAAAATT GAGAGAAGAG
1501  GAGGAACTTG AAAAGTTACG GAAGAAGGCC AGAGAGTCAC AACCAACCCA
1551  AGGGCCAAAA ATTACGAAT CCAGGTTATT TTTACAGAAG GACACCAGAG
1601  AAAATAGTAG ATCAAGATCG CCATTCACAG TGGAAACAAG AAAACGTGCT
1651  AGATCCAGAA CTCCACCAAG AGGATCGAGA AACCATCGTA ACAGATCCAG
1701  GACTCCGCCT GCAAGAAGGC AACGGCATAG ATGA
```

FIG.17 ygr278wp

```
  1 MSTATIQDED IKFQRENWEM IRSHVSPIIS NLTMDNLQES HRDLFQVNIL
 51 IGRNIICKNV VDFTLNKQNG RLIPALSALI ALLNSDIPDI GETLAKELML
101 MFVQQFNRKD YVSCGNILQC LSILFLYDVI HEIVILQILL LLLEKNSLRL
151 VIAVMKICGW KLALVSKKTH DMIWEKLRYI LQTQELSSTL RESLETLFEI
201 RQKDYKSGSQ GLFILDPTSY TVHTHSYIVS DEDEANKELG NFEKCENFNE
251 LTMAFDTLRQ KLLINNTSDT NEGSNSQLQI YDMTSTNDVE FKKKIYLVLK
301 SSLSGDEAAH KLLKLKIANN LKKSVVDIII KSSLQESTFS KFYSILSERM
351 ITFHRSWQTA YNETFEQNYT QDIEDYETDQ LRILGKFWGH LISYEFLPMD
401 CLKIIKLTEE ESCPQGRIFI KFLFQELVNE LGLDELQLRL NSSKLDGMFP
451 LEGDAEHIRY SINFFTAIGL GLLTEDMRSR LTIIQEVEDA EEEEKKLREE
501 EELEKLRKKA RESQPTQGPK IHESRLFLQK DTRENSRSRS PFTVETRKRA
551 RSRTPPRGSR NHRNRSRTPP ARRQRHR
```

FIG. 18 ygr278wp blastp       nr    results

| Sequences producing significant alignments: | Score (bits) | E Value |
|---|---|---|
| sp\|P53333\|YG5U_YEAST HYPOTHETICAL 67.3 KD PROTEIN IN TAF145-YOR... | 984 | 0.0 |
| emb\|CAA20491\|   (AL031349) conserved hypothetical protein [Schizo... | 208 | 8e-53 |
| gi\|987227  (U19615) LET 858 [Caenorhabditis elegans] >gi\|3876636... | 171 | 1e-41 |
| dbj\|BAA13763\|  (D89100) similar to Saccharomyces cerevisiae ORF ... | 98 | 2e-19 |
| gi\|2996650  (AC004493) KIAA0324 [Homo sapiens] | 48 | 2e-04 |
| dbj\|BAA20782\|  (AB002322) KIAA0324 [Homo sapiens] | 48 | 2e-04 |

FIG.19

YKR071C on chromosome XI from coordinates 575616 to 574570.

UPTAG primer:
TAAGTGAAGGTATCGATGGATGTCCACGAGGTCTCTGGCACTCTGACATAGTACCGCGTA
CGCTGCAGGTCGAC DOWNTAG primer:
ACGAATGTGCAGGGTTTACGGTGTCGGTCTCGTAGATATGCCACTCCATTGAGCGATCGA
TGAATTCGAGCTCG Upstream45 primer:
TCACATTTGATCTAAGCATATACACTGTAAGTGAAGGTATCGATG Downstream45 primer:
GTAGACCAATTGACGTCATTTACTGAAACGAATGTGCAGGGTTTA A primer: AATGCCATACTAGCGTACATAGAGC B primer: TTTCGGAAACTTAATATCAGTCTGG C primer: TCCATTGAAGAAGAAGAATTAATCG D primer: TGCGGTTACTAAAACGTTAGAAAAG KanB1 primer:   TGTACGGGCGACAGTCACAT KanC3 primer:   CCTCGACATCATCTGCCCAGAT

FIG.21 ykr071c

```
   1  ATGTCACAAT ACAAAACTGG TTTACTTTTA ATACATCCGG CGGTGACTAC
  51  AACGCCAGAG CTAGTAGAGA ACACTAAGGC TCAAGCTGCA TCAAAGAAAG
 101  TCAAGTTCGT GGACCAGTTT TTAATCAATA AACTAAATGA TGGGTCCATA
 151  ACTTTGGAAA ACGCAAAATA TGAAACAGTA CACTATTTGA CGCCAGAAGC
 201  CCAGACTGAT ATTAAGTTTC CGAAAAAGTT AATTTCTGTC TTAGCTGACT
 251  CATTGAAACC AAACGGCTCA CTAATTGGTT TAAGTGATAT TTATAAAGTA
 301  GATGCATTAA TCAATGGGTT TGAAATAATT AACGAACCAG ATTATTGCTG
 351  GATTAAAATG GATTCCTCTA AACTAAACCA AACTGTTTCT ATACCACTGA
 401  AAAAAAAGAA AACGAACAAT ACTAAGCTAC AGAGTGGTAG TAAGCTACCA
 451  ACTTTTAAAA AAGCTAGTTC TTCAACCTCT AATTTACCCT CATTCAAAAA
 501  AGCAGATCAC AGTAGGCAAC CTATAGTTAA GGAAACAGAC AGCTTCAAAC
 551  CACCTAGTTT CAAAATGACC ACTGAACCAA AAGTCTACCG AGTCGTAGAC
 601  GACCTGATTG AGGATAGCGA TGATGATGAT TTCTCTAGTG ACTCTTCCAA
 651  AGCCCAATAT TTTGATCAAG TGGATACCAG CGATGATTCC ATTGAAGAAG
 701  AAGAATTAAT CGACGAGGAT GGTTCTGGTA AGTCAATGAT TACTATGATT
 751  ACATGCGGTA AATCCAAAAC TAAGAAGAAG AAGGCTTGTA AAGATTGCAC
 801  CTGTGGTATG AAAGAACAGG AAGAAAATGA AATAAACGAT ATAAGATCTC
 851  AACAAGATAA AGTTGTCAAA TTTACAGAAG ACGAGTTGAC CGAGATTGAT
 901  TTCACTATCG ATGGGAAGAA AGTTGGCGGC TGTGGTTCTT GTTCTCTAGG
 951  GGATGCCTTT AGATGTAGTG GTTGTCCCTA CTTGGGTCTT CCTGCTTTCA
1001  AGCCTGGTCA ACCTATCAAT TTGGACAGCA TTTCAGATGA CTTGTAA
```

FIG. 22 ykr071cp

```
  1  MSQYKTGLLL  IHPAVTTTPE  LVENTKAQAA  SKKVKFVDQF  LINKLNDGSI
 51  TLENAKYETV  HYLTPEAQTD  IKFPKKLISV  LADSLKPNGS  LIGLSDIYKV
101  DALINGFEII  NEPDYCWIKM  DSSKLNQTVS  IPLKKKKTNN  TKLQSGSKLP
151  TFKKASSSTS  NLPSFKKADH  SRQPIVKETD  SFKPPSFKMT  TEPKVYRVVD
201  DLIEDSDDDD  FSSDSSKAQY  FDQVDTSDDS  IEEEELIDED  GSGKSMITMI
251  TCGKSKTKKK  KACKDCTCGM  KEQEENEIND  IRSQQDKVVK  FTEDELTEID
301  FTIDGKKVGG  CGSCSLGDAF  RCSGCPYLGL  PAFKPGQPIN  LDSISDDL
```

FIG.23 ykr071cp

```
                                                                 Score      E
Sequences producing significant alignments:                      (bits)  Value
sp|P36152|YK51_YEAST  HYPOTHETICAL 38.5 KD PROTEIN IN MET1-SIS2 ...  559  e-158
emb|CAA21280|         (AL031854) conserved hypothetical protein [Schizo...  75  1e-12
sp|P41847|Y097_CAEEL  HYPOTHETICAL 25.6 KD PROTEIN T20B12.7 IN C...   62  4e-09
gi|2293332            (AF011338) unknown [Dictyostelium discoideum]    60  2e-08
gi|3252825            (AC004382) Unknown gene product [Homo sapiens]   59  6e-08
gi|3252826            (AC004382) Unknown gene product [Homo sapiens]   59  6e-08
```

FIG.24 ykr071cp gi|3252825 (AC004382) Unknown gene product [Homo sapiens]
Length = 312
          Score = 58.6 bits (139), Expect = 6e-08
 Identities = 22/31 (70%), Positives = 27/31 (86%)
Query: 311 CGSCSLGDAFRCSGCPYLGLPAFKPGQPINL 341
           CG+C LGDAFRC+ CPYLG+PAFKPG+ + L
Sbjct: 274 CGNCYLGDAFRCASCPYLGMPAFKPGEKVLL 304

FIG.25

BLAST ALIGNMENTS FOR YKR071CP VS H. sapiens    HITS
A-152E5.9   A-152E5.9           2

QUERY RESULTS FOR: YKR071C PROTEIN OF UNKNOWN FUNCTION (LENGTH=348)
COMPARED WITH H. sapiens PROTEIN SEQUENCES (DOCUMENTATION)

| GENE | GenBank | SYNONYMS/DESCRIPTION | MATCH LENGTH | % IDEN | % SIM | HIGH SCORE | E VAL |
|---|---|---|---|---|---|---|---|
| A-152E5.9 | 3252825 | A-152E5.9 CC CHEMOKINE STCP-1 | 324 | 28% | 42% | 243 | 3e-20 |
| A-152E5.9 | 3252826 | A-152E5.9 CC CHEMOKINE STCP-1 | 364 | 26% | 41% | 218 | 9e-18 |

A-152E5.9 CC CHEMOKINE STCP-1
SCORE = 243    LENGTH = 312    EXPECT = 3e-20
IDENTITIES = 92/324 (28%)    SIMILARITIES = 137/324 (42%)    GAPS = 67/324 (21%)

FIG.26 ykr071c

YKR079C on chromosome XI from coordinates 588941 to 586425.

UPTAG primer:
GGAAGGTTTTCAACGATGGATGTCCACGAGGTCTCTATAGCATACCGAGTGACCCGCGTA
CGCTGCAGGTCGAC DOWNTAG primer:
TTAAGATGAATTATACTACGGTGTCGGTCTCGTAGACGGGACACTCATATTAGCGATCGA
TGAATTCGAGCTCG Upstream45 primer:
ACGACCACCCGCAAAGAAAAGAGTCCTGGAAGGTTTTCAACGATG Downstream45 primer:
CTACTGAAAAAGCAACAATATAAGAAGTTAAGATGAATTATACTA A primer: TTGCCTCCTTTTCTCTCTCTAAAAT B primer: CGTTCAAGTCTATTCCGAATCTAAA C primer: GATCTTAACACACTTTTCCCAGAGA D primer: AGGATGAATACCGCATTGTATTAAA KanB1 primer:    TGTACGGGCGACAGTCACAT KanC3 primer:    CCTCGACATCATCTGCCCAGAT

FIG.28 ykr079c

```
   1 ATGTTCACAT TTATACCCAT CACCCATCCT ACATCGGATA CAAAGCACCC
  51 ATTGCTGCTA GTCCAGTCTG CACATGGGGA AAAGTATTTC TTCGGTAAAA
 101 TTGGTGAAGG ATCCCAAAGG AGTCTGACTG AAAATAAGAT CAGGATATCC
 151 AAATTGAAGG ATATTTTCCT TACTGGTGAA TTAAACTGGT CAGATATAGG
 201 TGGATTACCT GGAATGATTT TGACTATTGC TGATCAAGGG AAAAGTAATC
 251 TTGTTTTGCA TTACGGCAAT GACATTTTGA ATTACATAGT TTCCACTTGG
 301 AGATACTTCG TCTTTAGATT CGGAATAGAC TTGAACGATC ACATTATGAA
 351 AGACAAGGAA GTATATAAAG ATAAGATAAT AGCTGTTAAA TCCTTTAATG
 401 TTCTGAAAAA TGGGGGGGAA GACAGGTTAG GCGTCTTCGA TAGTTTTCAA
 451 AAAGGTGTAT TACGTTCCAT AGTAGCAAAA ATGTTCCCCA AACATGCACC
 501 CACCGATAGG TACGATCCTT CTAGTGATCC GCACTTGAAT GTAGAGTTGC
 551 CTGACTTAGA CGCCAAAGTG GAAGTTTCTA CGAATTACGA GATTTCATTC
 601 AGTCCAGTGA GGGGTAAATT TAAAGTGGAG GAAGCTATTA AACTAGGTGT
 651 TCCGAAGGGT CCCTTATTTG CAAAGTTAAC CAAGGGCCAA ACAATTACTT
 701 TGGATAACGG TATTGTTGTA ACTCCGGAAC AGGTATTGGA GAATGAACGT
 751 CATTTTGCCA AAGTATTGAT CCTGGATATC CCAGATGACC TATATTTGAA
 801 CGCTTTCGTA GAAAAATTCA AGGATTATGA TTGTGCTGAG CTTGGCATGG
 851 TGTATTATTT TCTTGGTGAT GAGGTTACCA TTAATGATAA TCTATTCGCG
 901 TTCATTGACA TATTTGAGAA AAACAATTAT GGTAAAGTAA ATCATATGAT
 951 ATCCCACAAT AAAATTTCTC CAAACACGAT ATCATTTTTC GGTTCTGCAT
1001 TGACCACATT GAAATTAAAG GCACTACAAG TAAATAATTA CAATTTACCA
1051 AAAACAGATC GTGTGTTTTC CAAGGACTTC TACGACAGAT TCGATACACC
1101 ACTCAGCAGA GGTACATCTA TGTGTAAATC CCAGGAAGAG CCTTTGAATA
1151 CAATAATAGA GAAGGATAAC ATTCATATTT TTTCACAAAA CAAGACAGTA
1201 ACTTTCGAAC CATTTCGGAT GAACGAAGAA CCGATGAAAT GCAACATCAA
1251 CGGTGAAGTG GCGGATTTCT CGTGGCAAGA AATTTTCGAA GAACATGTAA
1301 AACCATTAGA ATTTCCCTTA GCTGATGTCG ATACAGTTAT CAATAATCAA
1351 CTACACGTGG ATAACTTTAA CAATTCAGCA GAAAAGAAGA AACACGTTGA
1401 AATTATCACC TTAGGAACCG GTAGTGCATT GCCTTCTAAA TATAGAAACG
1451 TTGTCTCCAC ACTTGTTAAA GTTCCTTTTA CTGACGCCGA TGGAAATACC
1501 ATAAATAGAA ACATTATGCT AGATGCTGGT GAAAATACTT TAGGTACCAT
1551 ACACAGGATG TTTTCTCAGC TAGCAGTCAA GTCAATATTT CAGGATTTGA
1601 AAATGATATA TCTGAGTCAC TTGCATGCAG ACCACCATTT GGGAATAATC
1651 AGCGTGCTAA ATGAATGGTA CAAATATAAC AAGGATGATG AAACGAGTTA
1701 TATATATGTG GTTACTCCAT GGCAATATCA CAAATTTGTT AATGAATGGT
1751 TAGTTCTAGA AAATAAAGAG ATTTTAAAGA GAATCAAATA CATAAGTTGT
1801 GAGCATTTCA TCAATGATTC GTTTGTAAGA ATGCAGACAC AATCTGTTCC
1851 TTTGGCAGAG TTCAATGAAA TATTGAAAGA AAATAGCAAT CAAGAATCAA
1901 ACAGAAAACT GGAACTGGAT AGAGATTCTT CATATAGGGA TGTTGACTTG
1951 ATCAGACAAA TGTATGAGGA TTTATCGATA GAATATTTTC AAACTTGCAG
```

FIG.29A

```
2001 AGCTATACAT TGTGACTGGG CATATTCGAA CTCAATTACC TTCCGAATGG
2051 ACGAAAACAA TGAGCATAAT ACATTCAAGG TTTCATATTC AGGCCATACA
2101 AGACCTAACA TCGAGAAATT TTCCCTCGAA ATAGGCTATA ATTCACATCT
2151 ATTAATTCAC GAAGCTACAC TAGAAAATCA GCTACTGGAG GATGCCGTGA
2201 AGAAAAAACA CTGCACTATT AATGAAGCAA TCGGTGTTTC GAACAAAATG
2251 AATGCTAGGA AGTTGATCTT AACACACTTT TCCCAGAGAT ATCCCAAATT
2301 GCCCCAATTA GACAATAATA TTGATGTGAT GGCGAGAGAA TTTTGTTTTG
2351 CTTTCGACAG TATGATCGTT GATTATGAGA AAATTGGTGA ACAGCAGCGT
2401 ATTTTTCCAC TGCTGAATAA GGCATTTGTT GAAGAAAAGG AAGAAGAAGA
2451 AGATGTTGAT GACGTTGAAA GCGTACAAGA TTTGGAAGTC AAACTTAAGA
2501 AACACAAGAA AAATTAG
```

FIG.29B ykr079cp

```
  1  MFTFIPITHP TSDTKHPLLL VQSAHGEKYF FGKIGEGSQR SLTENKIRIS
 51  KLKDIFLTGE LNWSDIGGLP GMILTIADQG KSNLVLHYGN DILNYIVSTW
101  RYFVFRFGID LNDHIMKDKE VYKDKIIAVK SFNVLKNGGE DRLGVFDSFQ
151  KGVLRSIVAK MFPKHAPTDR YDPSSDPHLN VELPDLDAKV EVSTNYEISF
201  SPVRGKFKVE EAIKLGVPKG PLFAKLTKGQ TITLDNGIVV TPEQVLENER
251  HFAKVLILDI PDDLYLNAFV EKFKDYDCAE LGMVYYFLGD EVTINDNLFA
301  FIDIFEKNNY GKVNHMISHN KISPNTISFF GSALTTLKLK ALQVNNYNLP
351  KTDRVFSKDF YDRFDTPLSR GTSMCKSQEE PLNTIIEKDN IHIFSQNKTV
401  TFEPFRMNEE PMKCNINGEV ADFSWQEIFE EHVKPLEFPL ADVDTVINNQ
451  LHVDNFNNSA EKKKHVEIIT LGTGSALPSK YRNVVSTLVK VPFTDADGNT
501  INRNIMLDAG ENTLGTIHRM FSQLAVKSIF QDLKMIYLSH LHADHHLGII
551  SVINEWYKYN KDDETSYIYV VTPWQYHKFV NEWLVLENKE ILKRIKYISC
601  EHFINDSFVR MQTQSVPLAE FNEILKENSN QESNRKLELD RDSSYRDVDL
651  IRQMYEDLSI EYFQTCRAIH CDWAYSNSIT FRMDENNEHN TFKVSYSGDT
701  RPNIEKFSLE IGYNSDLLIH EATLENQLLE DAVKKKHCTI NEAIGVSNKM
751  NARKLILTHF SQRYPKLPQL DNNIDVMARE FCFAFDSMIV DYEKIGEQQR
801  IFPLLNKAFV EEKEEEEDVD DVESVQDLEV KLKKHKKN
```

FIG.30 ykr079cp blastp          nr       results

```
                                                                        Score      E
Sequences producing significant alignments:                             (bits)   Value
sp|P36159|YK59_YEAST   HYPOTHETICAL 96.8 KD PROTEIN IN SIS2-MTD1 ...     1668    0.0
sp|Q10155|YATA_SCHPO   HYPOTHETICAL 90.6 KD PROTEIN C1D4.10 IN CH...      256    4e-67
gi|2702418  (AF038611) contains similarity to sulphatases [Caeno...      121    2e-26
emb|CAB09123.1|   (Z95620) conserved hypothetical protein [Schizo...     112    1e-23
gi|2649658  (AE001039) conserved hypothetical protein [Archaeogl...       84    3e-15
sp|Q58897|YF02_METJA   HYPOTHETICAL PROTEIN MJ1502 >gi|2128059|pi...      79    1e-13
dbj|BAA30251|   (AP000005) 307aa long hypothetical sulfatase [Pyr...      73    6e-12
gi|2622965  (AE000936) conserved protein [Methanobacterium therm...       73    8e-12
sp|P54548|YQJK_BACSU   HYPOTHETICAL 34.0 KD PROTEIN IN GLNQ-ANSR ...      64    4e-09
gi|2688688  (AE001175) conserved hypothetical protein [Borrelia ...       56    9e-07
gi|2196998  (U93844) Orf310 [Treponema pallidum] >gi|3323126 (AE...       53    8e-06
gb|AAD18178|   (AE001588) Sulphohydrolase/Glycosulfatase [Chlamyd...      53    8e-06
sp|Q55132|Y050_SYNY3   HYPOTHETICAL 36.1 KD PROTEIN >gi|1001126|d...      51    4e-05
```

FIG.31 ykr079c

YKR083C on chromosome XI from coordinates 596458 to 596057

UPTAG primer:
ATTCAGACAGTTATTATGGATGTCCACGAGGTCTCTAACTGTGTGGAATTAGCCCGCGTA
CGCTGCAGGTCGAC DOWNTAG primer:
TCCTTTTCTTTCTGTTCACGGTGTCGGTCTCGTAGACTATATGCGGAGACACGCGATCGA
TGAATTCGAGCTCG Upstream45 primer:
CTATTGAATAGGTTTGAAAAACTCATAATTCAGACAGTTATTATG Downstream45 primer:
AACTGCCTTCTTCCGATTTATATAAGATCCTTTTCTTTCTGTTCA A primer: AAGAGTTGTTCTTAGAAAGGACGGT B primer: TGATCTGCTCATTCAACTCTGTTAG C primer: AAAAAGGAATCTGAACAATCAAATG D primer: TGCCATACGTGAAGAGATATATGAA KanB1 primer: TGTACGGGCGACAGTCACAT KanC3 primer: CCTCGACATCATCTGCCCAGAT

FIG.33 ykr083c
```
  1  ATGGATTCAA TAGATGAACA AATTGCTATA AAGCGAAAAG AACTTCAGTC
 51  ATTACAAAAG ATAACCAGTT TAACGGATGG CTTAAAAATT CAGCTAACAG
101  AGTTGAATGA GCAGATCAAA GAAATGGGAA TGAATGCGGA TTCAGTGGCC
151  CAATTGATGA ACAATTGGGA TTCTATAATA AACAATATAT CGCAAGCAAG
201  TTTGGGATTA TTGCAATATG CAGAGGGTGA TTATGAGATA GGACCGTGGA
251  AAGATTCTAA GAAAAAGGAA TCTGAACAAT CAAATGAAAC AGGTCTTGAA
301  GCGCAAGAAA ATGATAAGAA TGATGAAGAT AATGATGAGG ATGAAGATCT
351  GGTACCCTTG CCGGAAACAA TGGTCAGAAT TAGGGTAGAT GGTAACGAAT
401  GA
```

FIG.34 ykr083cp

```
1    MDSIDEQIAI KRKELQSLQK ITSLTDGLKI QLTELNEQIK EMGMNADSVA
51   QLMNNWDSII NNISQASLGL LQYAEGDYEI GPWKDSKKKE SEQSNETGLE
101  AQENDKNDED NDEDEDLVPL PETMVRIRVD GNE
```

FIG. 35

```
Sequences producing significant alignments:                                              Score    E
                                                                                         (bits)  Value
sp|P36162|YK63_YEAST HYPOTHETICAL 15.1 KD PROTEIN IN NUP133-HBS...                        211    2E-60
gi|2702447 (AF038618) contains similarity to the HESA/MOEB/THIF...                        36    0.13
emb|CAA18504|(AL022373)  hypothetical protein [Arabidopsis thal...                        32    1.1
gi|2736151 (AF021935) mytonic dystrophy kinase-related Cdc42-bi...                        32    1.5
sp|Q18823|LML1_CAEEL LAMININ-LIKE PROTEIN CS4D1.5 PRECURSOR >gi...                        31    3.4
gb|AAD20127| (AC006201) unknown protein [Arabidopsis thaliana]                            31    3.4
sp|P06198|MYSP_SCHMA  PARAMYOSIN >gi|161059 (M36871) paramyosin...                        31    3.4
gi|2394450 (AF024496) ZC178.1 gene product [Caenorhabditis eleg...                        31    3.4
dbj|BAA13194| (D86958) similar to mouse CC1. [Homo sapiens]                               31    4.4
sp|P32380|NUF1_YEAST NUF1 PROTEIN (SPINDLE POLY BODY SPACER PRO...                        31    4.4
gi|1763304  (U75357) myosin II [Schizosaccharomyces pombe)                                31    4.4
gi|2772930  (AF029395) Genghis Khan [Drosophila malanogaster]                             31    4.4
sp|Q10368|YDBI_SCHPO  HYPOTHETICAL  38.4 KD PROTEIN C22E12.18 IN...                       31    4.4
gi|3329323  (AE001358) hypothetical protein [Chlamydia trachomatis]                       31    4.4
emb|CAB39901.1|  (AL049498) myosin ii [Schizosaccharomyces pombe]                         31    4.4
```

FIG.36 ykr083c

SEQUENCE LISTING

<160> NUMBER OF SEQ ID NOS: 64

<210> SEQ ID NO 1
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 1
attaagtcta taaggatgga tgtccacgag gtctctatcg aaccagcatt gcagagcgta      60
cgctgcaggt cgac                                                       74

<210> SEQ ID NO 2
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 2
tcgttgtaca aagcctcacg gtgtcggtct cgtagtactt cgtaagaggc ttgagatcga      60
tgaattcgag ctcg                                                       74

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 3

```
tgccaggagt tgcgagctaa gtcttcaatt aagtctataa ggatg              45

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 4
ttgctgcttc atcgaatatt ttggctttcg ttgtacaaag cctca              45

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 5
cctcttaatt gtgttatcac ctgct                                    25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 6
catgttttca ttgtcaatca cattt                                    25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 7
gaacgtagac aaagaagatt ggaaa                                    25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 8
tctgctagaa agaaagcaca agatt                                    25

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 9
tgtacgggcg acagtcacat                                          20

<210> SEQ ID NO 10
<211> LENGTH: 22
<212> TYPE: DNA
<213> ORGANISM: Artificial Sequence
```

-continued

```
<220> FEATURE:
<223> OTHER INFORMATION: Description of Artificial Sequence: primer

<400> SEQUENCE: 10
cctcgacatc atctgcccag at                                              22

<210> SEQ ID NO 11
<211> LENGTH: 468
<212> TYPE: DNA
<213> ORGANISM: Saccharomyces cerevisiae

<400> SEQUENCE: 11
atgagtggaa atcaaatggc tatgggatca gaacaacaac agaccgtagg gtcccgaacg     60
gtgagtgtgg aagaggttcc cgcagttttg cagcttcgag caactcaaga tcctccaaga    120
agccaggagg caatgcctac aaggcacaat gtaagatggg aagaaaatgt gattgacaat    180
gaaaacatga ataaaaaaaa gaccaagata tgctgcattt ttcatccaca aaatgaggat    240
gaagaagagt gcaaccatca ttcagatgat gatggatcct cttcttccgg atcctcttct    300
tcagaatctg agaatgagaa ggatcttgac tttaacgaac gtagacaaag aagattggaa    360
aggcgccatc gtaaacttga gaaaaaagg tcatatagcc ccaatgctta tgaaatccaa    420
ccagattatt ctgaatacag gcgaaaacag caggaaaaga aggactga               468

<210> SEQ ID NO 12
<211> LENGTH: 155
<212> TYPE: PRT
<213> ORGANISM: Saccharomyces cerevisiae

<400> SEQUENCE: 12

Met Ser Gly Asn Gln Met Ala Met Gly Ser Glu Gln Gln Gln Thr Val
  1               5                  10                  15

Gly Ser Arg Thr Val Ser Val Glu Glu Val Pro Ala Val Leu Gln Leu
                 20                  25                  30

Arg Ala Thr Gln Asp Pro Pro Arg Ser Gln Glu Ala Met Pro Thr Arg
             35                  40                  45

His Asn Val Arg Trp Glu Glu Asn Val Ile Asp Asn Glu Asn Met Asn
         50                  55                  60

Lys Lys Lys Thr Lys Ile Cys Cys Ile Phe His Pro Gln Asn Glu Asp
 65                  70                  75                  80

Glu Glu Glu Cys Asn His His Ser Asp Asp Asp Gly Ser Ser Ser Ser
                 85                  90                  95

Gly Ser Ser Ser Ser Glu Ser Glu Asn Glu Lys Asp Leu Asp Phe Asn
                100                 105                 110

Glu Arg Arg Gln Arg Arg Leu Glu Arg Arg His Arg Lys Leu Glu Lys
            115                 120                 125

Lys Arg Ser Tyr Ser Pro Asn Ala Tyr Glu Ile Gln Pro Asp Tyr Ser
        130                 135                 140

Glu Tyr Arg Arg Lys Gln Gln Glu Lys Lys Asp
145                 150                 155

<210> SEQ ID NO 13
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 13
```
gtaaagaagt gtaagatgga tgtccacgag gtctctattg cagactacgg cctacgcgta    60
cgctgcaggt cgac    74

<210> SEQ ID NO 14
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 14
tatacaaaaa tatgtttacg gtgtcggtct cgtagattgc attgtaaccg cgccgatcga    60
tgaattcgag ctcg    74

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 15
agacgtgatt aaacctaaaa atctaaagta aagaagtgta agatg    45

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 16
aaataatagt gaactacaac aataaaatat acaaaaatat gttta    45

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 17
ttatcatttc ccagttttct ctctg    25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 18
tcaacaatat tttatgtcca tcgtg    25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 19
cacttttgaa acttggaagc tagag    25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 20
acttccgata ccacatttgt atgat                                    25

<210> SEQ ID NO 21
<211> LENGTH: 918
<212> TYPE: DNA
<213> ORGANISM: Saccharomyces cerevisiae

<400> SEQUENCE: 21
atggttgagg aaaattccag agttttgatt gttcttcctt ataccaccgcc tagtgctact    60 ttgcagagga ttatagggca aactattccg ttcttaagag aatgtcaaag tcaactagac   120
atcgtgattg tacctgaatt caaaaccctca ttccagttgg attctgcgct agggaagatg   180
tacagtatta ccagggatgt ccttttgggc tatggaatga tcaacagcgg aatcaacatc   240
atattcaaca atattcattt cgtcgagagt aatttgcaat ggaaagtggt tttattgcca   300
caggaatcca cttttgaaac ttggaagcta gagttgggac aaggacaata ccatagtata   360
gaacattatg cattcacga taatataatg aagagatag aaggtcccaa agatgctaac   420
aaatttcatg tcaccgcatt gggcggaacg ttcgaccaca ttcacgatgg acataaaata   480
ttgttgagcg tctctacatt catcacgtca caaaggttaa tttgtggaat tacgtgcgat   540
gagctcttgc aaaacaagaa atacaaagag ttgattgaac cttatgatac acgatgcagg   600
cacgtacatc aattcatcaa gttgttaaaa ccggatctct ccgtagaact agttccctta   660
agggacgtgt gcggccccac agggaaagta cccgagatag aatgtttagt tgtgagtaga   720
gaaaccgtca gtggggcaga gactgtgaat aagactagga ttgaaaaagg catgagccca   780
ttggcagtac atgtggttaa tgtacttgga ggaaggagg aagacggctg gagcgagaag   840
ttaagcagca cggaaatcag acgcctactt aagtcctctg cttcgccaac gtgcactcca   900 caaaacccctt gcgtataa                                              918

<210> SEQ ID NO 22
<211> LENGTH: 305
<212> TYPE: PRT
<213> ORGANISM: Saccharomyces cerevisiae

<400> SEQUENCE: 22

Met Val Glu Glu Asn Ser Arg Val Leu Ile Val Leu Pro Tyr Thr Pro
 1               5                  10                  15

Pro Ser Ala Thr Leu Gln Arg Ile Ile Gly Gln Thr Ile Pro Phe Leu
             20                  25                  30

Arg Glu Cys Gln Ser Gln Leu Asp Ile Val Ile Val Pro Glu Phe Lys
         35                  40                  45

Thr Ser Phe Gln Leu Asp Ser Ala Leu Gly Lys Met Tyr Ser Ile Thr
     50                  55                  60

Arg Asp Val Leu Leu Gly Tyr Gly Met Ile Asn Ser Gly Ile Asn Ile
 65                  70                  75                  80

Ile Phe Asn Asn Ile His Phe Val Glu Ser Asn Leu Gln Trp Lys Val
                 85                  90                  95

Val Leu Leu Pro Gln Glu Ser Thr Phe Glu Thr Trp Lys Leu Glu Leu
            100                 105                 110

```
Gly Gln Gly Gln Tyr His Ser Ile Glu His Tyr Ala Leu His Asp Asn
            115                 120                 125
Ile Met Glu Glu Ile Glu Gly Pro Lys Asp Ala Asn Lys Phe His Val
    130                 135                 140
Thr Ala Leu Gly Gly Thr Phe Asp His Ile His Asp Gly His Lys Ile
145                 150                 155                 160
Leu Leu Ser Val Ser Thr Phe Ile Thr Ser Gln Arg Leu Ile Cys Gly
                165                 170                 175
Ile Thr Cys Asp Glu Leu Leu Gln Asn Lys Lys Tyr Lys Glu Leu Ile
            180                 185                 190
Glu Pro Tyr Asp Thr Arg Cys Arg His Val His Gln Phe Ile Lys Leu
        195                 200                 205
Leu Lys Pro Asp Leu Ser Val Glu Leu Val Pro Leu Arg Asp Val Cys
    210                 215                 220
Gly Pro Thr Gly Lys Val Pro Glu Ile Glu Cys Leu Val Val Ser Arg
225                 230                 235                 240
Glu Thr Val Ser Gly Ala Glu Thr Val Asn Lys Thr Arg Ile Glu Lys
                245                 250                 255
Gly Met Ser Pro Leu Ala Val His Val Asn Val Leu Gly Gly Arg
            260                 265                 270
Glu Glu Asp Gly Trp Ser Glu Lys Leu Ser Ser Thr Glu Ile Arg Arg
        275                 280                 285
Leu Leu Lys Ser Ser Ala Ser Pro Thr Cys Thr Pro Gln Asn Pro Cys
    290                 295                 300
Val
305

<210> SEQ ID NO 23
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 23
aggctacaaa ccagcatgga tgtccacgag gtctctaagt acaggtaatg cctacgcgta      60
cgctgcaggt cgac                                                        74

<210> SEQ ID NO 24
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 24
gtttggccgg gctcttcacg gtgtcggtct cgtaggcaca aatataacgt cgccgatcga      60
tgaattcgag ctcg                                                        74

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 25
gagtaagaaa cctaaaaagg aataaaaagg ctacaaaacca gcatg                     45
```

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 26
atatgtacga ttacatgtgt aatgtttgtt tggccgggct cttca                    45

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 27
aatgaggttt tgaattcagg tacaa                                          25

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 28
tctggaatat cagaatttag caagg                                          25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 29
attattcaag aagttgagga tgcag                                          25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 30
tatatcaaag gactgctttc tggtt                                          25

<210> SEQ ID NO 31
<211> LENGTH: 1734
<212> TYPE: DNA
<213> ORGANISM: Saccharomyces cerevisiae

<400> SEQUENCE: 31
atgtctaccg ctaccataca ggatgaagac attaaatttc agagagaaaa ctgggaaatg     60
ataaggtcac acgtttcacc cataatatcc aatttaacaa tggacaactt acaggaatcg    120
cacagagact tatttcaagt caatatactt attggccgca acataaattt gtaaaaatgtt  180 gtggatttta ctctgaacaa acagaatggc aggctaatcc ctgctttatc cgctttgatt    240
gccttgctaa attctgatat tccagatatt ggagaaactt tagcaaaaga actaatgtta    300

-continued

| | |
|---|---|
| atgttcgtgc agcaattcaa tcgcaaagat tacgtgtcct gcggaaatat ccttcaatgt | 360 |
| ctgtccattt tatttcttta tgatgtaatt catgaaatcg tgatcttaca gattctattg | 420 |
| ctactccttg aaaagaattc tttacgactg gtcattgccg tgatgaaaat atgtggctgg | 480 |
| aaacttgcac ttgtcagtaa gaaaacccat gatatgattt gggagaagtt aagatatatt | 540 |
| ttgcaaacac aggagttatc tagtacacta cgtgagtcgt tagagactct gtttgaaata | 600 |
| aggcaaaaag attataaatc tgggtctcaa ggtctgttta tattggaccc aactagttac | 660 |
| acagttcata cgcactccta tattgttagt gatgaggatg aagccaacaa agaactggga | 720 |
| aattttgaaa gtgtgaaaa tttcaatgaa ctaaccatgg cgtttgatac gctacgacag | 780 |
| aagctgctga taaataatac gtccgacaca atgaaggta gtaacagtca attacaaatc | 840 |
| tatgacatga catctaccaa tgatgtcgag tttaaaaaga gatttatttt ggttctgaaa | 900 |
| agttcattat caggtgacga agcggctcac aaattgctaa aattaaagat tgcgaacaat | 960 |
| ttgaaaaaaa gcgtggtaga tataatcatc aaatctagtt tgcaggaatc tacattctct | 1020 |
| aaattttatt ctattttgtc cgaacgtatg ataacgttcc acaggagttg gcagacagct | 1080 |
| tacaatgaaa cttttgagca gaattataca caagatatcg aagattatga aactgaccaa | 1140 |
| ctgcgaatct taggtaagtt ttggggacac ttaatatctt atgaatttct tccaatggac | 1200 |
| tgtcttaaga taattaagtt aactgaggaa gaatcgtgtc ctcaaggaag aattttcatc | 1260 |
| aaattttat ttcaagagct cgtaaatgag ctcggattag atgagctgca attaaggcta | 1320 |
| aactccagca agcttgacgg aatgtttccg ctggaaggag acgccgaaca tataagatac | 1380 |
| tccataaatt tctttactgc cataggattg ggcctgctca cagaggacat gagaagccgg | 1440 |
| ttgacaatta ttcaagaagt tgaggatgca gaggaagaag aaaaaaaatt gagagaagag | 1500 |
| gaggaacttg aaaagttacg gaagaaggcc agagagtcac aaccaaccca agggccaaaa | 1560 |
| attcacgaat ccaggttatt tttacagaag gacaccagag aaaatagtag atcaagatcg | 1620 |
| ccattcacag tggaaacaag aaaacgtgct agatccagaa ctccaccaag aggatcgaga | 1680 |
| aaccatcgta acagatccag gactccgcct gcaagaaggc aacggcatag atga | 1734 |

<210> SEQ ID NO 32
<211> LENGTH: 577
<212> TYPE: PRT
<213> ORGANISM: Saccharomyces cerevisiae

<400> SEQUENCE: 32

Met Ser Thr Ala Thr Ile Gln Asp Glu Asp Ile Lys Phe Gln Arg Glu
1               5                   10                  15

Asn Trp Glu Met Ile Arg Ser His Val Ser Pro Ile Ile Ser Asn Leu
            20                  25                  30

Thr Met Asp Asn Leu Gln Glu Ser His Arg Asp Leu Phe Gln Val Asn
        35                  40                  45

Ile Leu Ile Gly Arg Asn Ile Ile Cys Lys Asn Val Val Asp Phe Thr
    50                  55                  60

Leu Asn Lys Gln Asn Gly Arg Leu Ile Pro Ala Leu Ser Ala Leu Ile
65                  70                  75                  80

Ala Leu Leu Asn Ser Asp Ile Pro Asp Ile Gly Glu Thr Leu Ala Lys
                85                  90                  95

Glu Leu Met Leu Met Phe Val Gln Gln Phe Asn Arg Lys Asp Tyr Val
            100                 105                 110

Ser Cys Gly Asn Ile Leu Gln Cys Leu Ser Ile Leu Phe Leu Tyr Asp
        115                 120                 125

```
Val Ile His Glu Ile Val Ile Leu Gln Ile Leu Leu Leu Leu Glu
130                 135                 140

Lys Asn Ser Leu Arg Leu Val Ile Ala Val Met Lys Ile Cys Gly Trp
145                 150                 155                 160

Lys Leu Ala Leu Val Ser Lys Lys Thr His Asp Met Ile Trp Glu Lys
                165                 170                 175

Leu Arg Tyr Ile Leu Gln Thr Gln Glu Leu Ser Ser Thr Leu Arg Glu
                180                 185                 190

Ser Leu Glu Thr Leu Phe Glu Ile Arg Gln Lys Asp Tyr Lys Ser Gly
        195                 200                 205

Ser Gln Gly Leu Phe Ile Leu Asp Pro Thr Ser Tyr Thr Val His Thr
        210                 215                 220

His Ser Tyr Ile Val Ser Asp Glu Asp Glu Ala Asn Lys Glu Leu Gly
225                 230                 235                 240

Asn Phe Glu Lys Cys Glu Asn Phe Asn Glu Leu Thr Met Ala Phe Asp
                245                 250                 255

Thr Leu Arg Gln Lys Leu Leu Ile Asn Asn Thr Ser Asp Thr Asn Glu
                260                 265                 270

Gly Ser Asn Ser Gln Leu Gln Ile Tyr Asp Met Thr Ser Thr Asn Asp
        275                 280                 285

Val Glu Phe Lys Lys Lys Ile Tyr Leu Val Leu Lys Ser Ser Leu Ser
        290                 295                 300

Gly Asp Glu Ala Ala His Lys Leu Leu Lys Leu Lys Ile Ala Asn Asn
305                 310                 315                 320

Leu Lys Lys Ser Val Val Asp Ile Ile Ile Lys Ser Ser Leu Gln Glu
                325                 330                 335

Ser Thr Phe Ser Lys Phe Tyr Ser Ile Leu Ser Glu Arg Met Ile Thr
                340                 345                 350

Phe His Arg Ser Trp Gln Thr Ala Tyr Asn Glu Thr Phe Glu Gln Asn
        355                 360                 365

Tyr Thr Gln Asp Ile Glu Asp Tyr Glu Thr Asp Gln Leu Arg Ile Leu
370                 375                 380

Gly Lys Phe Trp Gly His Leu Ile Ser Tyr Glu Phe Leu Pro Met Asp
385                 390                 395                 400

Cys Leu Lys Ile Ile Lys Leu Thr Glu Glu Glu Ser Cys Pro Gln Gly
                405                 410                 415

Arg Ile Phe Ile Lys Phe Leu Gln Glu Leu Val Asn Glu Leu Gly
                420                 425                 430

Leu Asp Glu Leu Gln Leu Arg Leu Asn Ser Ser Lys Leu Asp Gly Met
        435                 440                 445

Phe Pro Leu Glu Gly Asp Ala Glu His Ile Arg Tyr Ser Ile Asn Phe
        450                 455                 460

Phe Thr Ala Ile Gly Leu Gly Leu Leu Thr Glu Asp Met Arg Ser Arg
465                 470                 475                 480

Leu Thr Ile Ile Gln Glu Val Glu Asp Ala Glu Glu Glu Lys Lys
                485                 490                 495

Leu Arg Glu Glu Glu Glu Leu Glu Lys Leu Arg Lys Ala Arg Glu
                500                 505                 510

Ser Gln Pro Thr Gln Gly Pro Lys Ile His Glu Ser Arg Leu Phe Leu
        515                 520                 525

Gln Lys Asp Thr Arg Glu Asn Ser Arg Ser Arg Ser Pro Phe Thr Val
        530                 535                 540
```

```
Glu Thr Arg Lys Arg Ala Arg Ser Arg Thr Pro Pro Arg Gly Ser Arg
545                 550                 555                 560

Asn His Arg Asn Arg Ser Arg Thr Pro Pro Ala Arg Arg Gln Arg His
                565                 570                 575

Arg

<210> SEQ ID NO 33
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 33
taagtgaagg tatcgatgga tgtccacgag gtctctggca ctctgacata gtaccgcgta      60
cgctgcaggt cgac                                                        74

<210> SEQ ID NO 34
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 34
acgaatgtgc agggtttacg gtgtcggtct cgtagatatg ccactccatt gagcgatcga      60
tgaattcgag ctcg                                                        74

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 35
tcacatttga tctaagcata tacactgtaa gtgaaggtat cgatg                      45

<210> SEQ ID NO 36
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 36
gtagaccaat tgacgtcatt tactgaaacg aatgtgcagg gttta                      45

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 37
aatgccatac tagcgtacat agagc                                            25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: primer
```

```
<400> SEQUENCE: 38
tttcggaaac ttaatatcag tctgg                                         25

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 39
tccattgaag aagaagaatt aatcg                                         25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 40
tgcggttact aaaacgttag aaaag                                         25

<210> SEQ ID NO 41
<211> LENGTH: 1047
<212> TYPE: DNA
<213> ORGANISM: Saccharomyces cerevisiae

<400> SEQUENCE: 41
atgtcacaat acaaaactgg tttactttta atacatccgg cggtgactac aacgccagag     60
ctagtagaga acactaaggc tcaagctgca tcaaagaaag tcaagttcgt ggaccagttt    120
ttaatcaata aactaaatga tgggtccata actttggaaa acgcaaaata tgaaacagta    180
cactatttga cgccagaagc ccagactgat attaagtttc cgaaaaagtt aatttctgtc    240
ttagctgact cattgaaacc aaacggctca ctaattggtt taagtgatat ttataaagta    300
gatgcattaa tcaatgggtt tgaaataatt aacgaaccag attattgctg gattaaaatg    360
gattcctcta aactaaacca aactgtttct ataccactga aaaaaagaa acgaacaat     420 actaagctac agagtggtag taagctacca acttttaaaa aagctagttc ttcaacctct    480
aatttaccct cattcaaaaa agcagatcac agtaggcaac ctatagttaa ggaaacagac    540
agcttcaaac cacctagttt caaaatgacc actgaaccaa aagtctaccg agtcgtagac    600
gacctgattg aggatagcga tgatgatgat ttctctagtg actcttccaa agcccaatat    660
tttgatcaag tggataccag cgatgattcc attgaagaag aagaattaat cgacgaggat    720
ggttctggta agtcaatgat tactatgatt acatgcggta atccaaaac taagaagaag     780 aaggcttgta agattgcac ctgtggtatg aagaacagg aagaaaatga aataaacgat      840
ataagatctc aacaagataa agttgtcaaa tttacagaag acgagttgac cgagattgat    900
ttcactatcg atgggaagaa agttggcggc tgtggttctt gttctctagg ggatgccttt    960
agatgtagtg gttgtcccta cttgggtctt cctgctttca gcctggtca acctatcaat    1020 ttggacagca tttcagatga cttgtaa                                      1047

<210> SEQ ID NO 42
<211> LENGTH: 348
<212> TYPE: PRT
<213> ORGANISM: Saccharomyces cerevisiae
```

<400> SEQUENCE: 42

| | | | | | | | | | | | | | | |
|---|---|---|---|---|---|---|---|---|---|---|---|---|---|---|
| Met | Ser | Gln | Tyr | Lys | Thr | Gly | Leu | Leu | Leu | Ile | His | Pro | Ala | Val | Thr |
| 1 | | | | 5 | | | | | 10 | | | | | 15 |

Met Ser Gln Tyr Lys Thr Gly Leu Leu Leu Ile His Pro Ala Val Thr
  1               5                  10                 15

Thr Thr Pro Glu Leu Val Glu Asn Thr Lys Ala Gln Ala Ala Ser Lys
             20                  25                  30

Lys Val Lys Phe Val Asp Gln Phe Leu Ile Asn Lys Leu Asn Asp Gly
         35                  40                  45

Ser Ile Thr Leu Glu Asn Ala Lys Tyr Glu Thr Val His Tyr Leu Thr
     50                  55                  60

Pro Glu Ala Gln Thr Asp Ile Lys Phe Pro Lys Leu Ile Ser Val
 65              70                  75                  80

Leu Ala Asp Ser Leu Lys Pro Asn Gly Ser Leu Ile Gly Leu Ser Asp
                 85                  90                  95

Ile Tyr Lys Val Asp Ala Leu Ile Asn Gly Phe Glu Ile Ile Asn Glu
            100                 105                 110

Pro Asp Tyr Cys Trp Ile Lys Met Asp Ser Ser Lys Leu Asn Gln Thr
            115                 120                 125

Val Ser Ile Pro Leu Lys Lys Lys Thr Asn Asn Thr Lys Leu Gln
 130                 135                 140

Ser Gly Ser Lys Leu Pro Thr Phe Lys Lys Ala Ser Ser Ser Thr Ser
 145                 150                 155                 160

Asn Leu Pro Ser Phe Lys Lys Ala Asp His Ser Arg Gln Pro Ile Val
                 165                 170                 175

Lys Glu Thr Asp Ser Phe Lys Pro Pro Ser Phe Lys Met Thr Thr Glu
             180                 185                 190

Pro Lys Val Tyr Arg Val Val Asp Asp Leu Ile Glu Asp Ser Asp
             195                 200                 205

Asp Asp Phe Ser Ser Asp Ser Ser Lys Ala Gln Tyr Phe Asp Gln Val
 210                 215                 220

Asp Thr Ser Asp Asp Ser Ile Glu Glu Glu Leu Ile Asp Glu Asp
 225                 230                 235                 240

Gly Ser Gly Lys Ser Met Ile Thr Met Ile Thr Cys Gly Lys Ser Lys
             245                 250                 255

Thr Lys Lys Lys Ala Cys Lys Asp Cys Thr Cys Gly Met Lys Glu
             260                 265                 270

Gln Glu Glu Asn Glu Ile Asn Asp Ile Arg Ser Gln Gln Asp Lys Val
             275                 280                 285

Val Lys Phe Thr Glu Asp Glu Leu Thr Glu Ile Asp Phe Thr Ile Asp
 290                 295                 300

Gly Lys Lys Val Gly Gly Cys Gly Ser Cys Ser Leu Gly Asp Ala Phe
 305                 310                 315                 320

Arg Cys Ser Gly Cys Pro Tyr Leu Gly Leu Pro Ala Phe Lys Pro Gly
             325                 330                 335

Gln Pro Ile Asn Leu Asp Ser Ile Ser Asp Asp Leu
             340                 345

<210> SEQ ID NO 43
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 43
ggaaggtttt caacgatgga tgtccacgag gtctctatag cataccgagt gacccgcgta    60
cgctgcaggt cgac                                                         74

<210> SEQ ID NO 44
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 44
ttaagatgaa ttatactacg gtgtcggtct cgtagacggg acactcatat tagcgatcga      60
tgaattcgag ctcg                                                         74

<210> SEQ ID NO 45
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 45
acgaccaccc gcaaagaaaa gagtcctgga aggttttcaa cgatg                       45

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 46
ctactgaaaa agcaacaata taagaagtta agatgaatta tacta                       45

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 47
ttgcctcctt ttctctctct aaaat                                             25

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 48
cgttcaagtc tattccgaat ctaaa                                             25

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 49
gatcttaaca cacttttccc agaga                                             25

<210> SEQ ID NO 50
<211> LENGTH: 25

```
<212> TYPE: DNA
<213> ORGANISM: Artificial Sequence
<220> FEATURE:
<223> OTHER INFORMATION: Description of Artificial Sequence: primer

<400> SEQUENCE: 50
aggatgaata ccgcattgta ttaaa                                      25

<210> SEQ ID NO 51
<211> LENGTH: 2517
<212> TYPE: DNA
<213> ORGANISM: Saccharomyces cerevisiae

<400> SEQUENCE: 51
atgttcacat ttatacccat cacccatcct acatcggata caaagcaccc attgctgcta    60
gtccagtctg cacatgggga aaagtatttc ttcggtaaaa ttggtgaagg atcccaaagg   120
agtctgactg aaaataagat caggatatcc aaattgaagg atattttcct tactggtgaa   180
ttaaactggt cagatatagg tggattacct ggaatgattt tgactattgc tgatcaaggg   240
aaaagtaatc ttgttttgca ttacggcaat gacatttga  attacatagt ttccacttgg   300
agatacttcg tctttagatt cggaatagac ttgaacgatc acattatgaa agacaaggaa   360
gtatataaag ataagataat agctgttaaa tcctttaatg ttctgaaaaa tggggggggaa   420 gacaggttag gcgtcttcga tagttttcaa aaaggtgtat tacgttccat agtagcaaaa   480
atgttcccca aacatgcacc caccgatagg tacgatcctt ctagtgatcc gcacttgaat   540
gtagagttgc ctgacttaga cgccaaagtg gaagtttcta cgaattacga gatttcattc   600
agtccagtga ggggtaaatt taagtggag  gaagctatta actaggtgt tccgaagggt   660 cccttatttg caaagttaac caagggccaa acaattactt tggataacgg tattgttgta   720
actccggaac aggtattgga gaatgaacgt cattttgcca aagtattgat cctggatatc   780
ccagatgacc tatatttgaa cgctttcgta gaaaaattca aggattatga ttgtgctgag   840
cttggcatgg tgtattattt tcttggtgat gaggttacca ttaatgataa tctattcgcg   900
ttcattgaca tatttgagaa aaacaattat ggtaaagtaa atcatatgat atcccacaat   960
aaaatttctc caaacacgat atcattttc  ggttctgcat tgaccacatt gaaattaaag  1020
gcactacaag taaataatta caatttacca aaaacagatc gtgtgttttc caaggacttc  1080
tacgacagat tcgatacacc actcagcaga ggtacatcta tgtgtaaatc ccaggaagag  1140
cctttgaata caataataga gaaggataac attcatattt tttcacaaaa caagacagta  1200
actttcgaac catttcggat gaacgaagaa ccgatgaaat gcaacatcaa cggtgaagtg  1260
gcggatttct cgtggcaaga aattttcgaa gaacatgtaa aaccattaga atttccctta  1320
gctgatgtcg atacagttat caataatcaa ctacacgtgg ataactttaa caattcagca  1380
gaaaagaaga aacacgttga aattatcacc ttaggaaccg gtagtgcatt gccttctaaa  1440
tatagaaacg ttgtctccac acttgttaaa gttccttta ctgacgccga tggaaatacc  1500
ataaatagaa acattatgct agatgctggt gaaaatactt taggtaccat acacaggatg  1560
ttttctcagc tagcagtcaa gtcaatattt caggatttga aatgatata  tctgagtcac  1620 ttgcatgcag accaccattt gggaataatc agcgtgctaa atgaatggta caaatataac  1680
aaggatgatg aaacgagtta tatatatgtg gttactccat ggcaatatca caatttgtt   1740 aatgaatggt tagttctaga aaataagag  atttaaaga  gaatcaaata cataagttgt  1800
gagcatttca tcaatgattc gtttgtaaga atgcagacac aatctgttcc tttggcagag  1860
```

```
ttcaatgaaa tattgaaaga aaatagcaat caagaatcaa acagaaaact ggaactggat      1920
agagattctt catataggga tgttgacttg atcagacaaa tgtatgagga tttatcgata      1980
gaatattttc aaacttgcag agctatacat tgtgactggg catattcgaa ctcaattacc      2040
ttccgaatgg acgaaaacaa tgagcataat acattcaagg tttcatattc aggcgataca      2100
agacctaaca tcgagaaatt tcccctcgaa ataggctata attcagatct attaattcac      2160
gaagctacac tagaaaatca gctactggag gatgccgtga agaaaaaaca ctgcactatt      2220
aatgaagcaa tcggtgtttc gaacaaaatg aatgctagga agttgatctt aacacacttt      2280
tcccagagat atcccaaatt gccccaatta gacaataata ttgatgtgat ggcgagagaa      2340
ttttgttttg ctttcgacag tatgatcgtt gattatgaga aaattggtga acagcagcgt      2400 attttccac tgctgaataa ggcatttgtt gaagaaaagg aagaagaaga agatgttgat      2460
gacgttgaaa gcgtacaaga tttggaagtc aaacttaaga aacacaagaa aaattag        2517

<210> SEQ ID NO 52
<211> LENGTH: 838
<212> TYPE: PRT
<213> ORGANISM: Saccharomyces cerevisiae

<400> SEQUENCE: 52

Met Phe Thr Phe Ile Pro Ile Thr His Pro Thr Ser Asp Thr Lys His
  1               5                  10                  15

Pro Leu Leu Leu Val Gln Ser Ala His Gly Glu Lys Tyr Phe Phe Gly
                 20                  25                  30

Lys Ile Gly Glu Gly Ser Gln Arg Ser Leu Thr Glu Asn Lys Ile Arg
             35                  40                  45

Ile Ser Lys Leu Lys Asp Ile Phe Leu Thr Gly Glu Leu Asn Trp Ser
         50                  55                  60

Asp Ile Gly Gly Leu Pro Gly Met Ile Leu Thr Ile Ala Asp Gln Gly
     65                  70                  75                  80

Lys Ser Asn Leu Val Leu His Tyr Gly Asn Asp Ile Leu Asn Tyr Ile
                 85                  90                  95

Val Ser Thr Trp Arg Tyr Phe Val Phe Arg Phe Gly Ile Asp Leu Asn
                100                 105                 110

Asp His Ile Met Lys Asp Lys Glu Val Tyr Lys Asp Lys Ile Ile Ala
            115                 120                 125

Val Lys Ser Phe Asn Val Leu Lys Asn Gly Gly Glu Asp Arg Leu Gly
        130                 135                 140

Val Phe Asp Ser Phe Gln Lys Gly Val Leu Arg Ser Ile Val Ala Lys
    145                 150                 155                 160

Met Phe Pro Lys His Ala Pro Thr Asp Arg Tyr Asp Pro Ser Ser Asp
                165                 170                 175

Pro His Leu Asn Val Glu Leu Pro Asp Leu Asp Ala Lys Val Glu Val
            180                 185                 190

Ser Thr Asn Tyr Glu Ile Ser Phe Ser Pro Val Arg Gly Lys Phe Lys
        195                 200                 205

Val Glu Glu Ala Ile Lys Leu Gly Val Pro Lys Gly Pro Leu Phe Ala
    210                 215                 220

Lys Leu Thr Lys Gly Gln Thr Ile Thr Leu Asp Asn Gly Ile Val Val
225                 230                 235                 240

Thr Pro Glu Gln Val Leu Glu Asn Glu Arg His Phe Ala Lys Val Leu
                245                 250                 255

Ile Leu Asp Ile Pro Asp Asp Leu Tyr Leu Asn Ala Phe Val Glu Lys
```

-continued

```
                260                 265                 270
Phe Lys Asp Tyr Asp Cys Ala Glu Leu Gly Met Val Tyr Tyr Phe Leu
            275                 280                 285
Gly Asp Glu Val Thr Ile Asn Asp Asn Leu Phe Ala Phe Ile Asp Ile
        290                 295                 300
Phe Glu Lys Asn Asn Tyr Gly Lys Val Asn His Met Ile Ser His Asn
305                 310                 315                 320
Lys Ile Ser Pro Asn Thr Ile Ser Phe Phe Gly Ser Ala Leu Thr Thr
            325                 330                 335
Leu Lys Leu Lys Ala Leu Gln Val Asn Asn Tyr Asn Leu Pro Lys Thr
            340                 345                 350
Asp Arg Val Phe Ser Lys Asp Phe Tyr Asp Arg Phe Asp Thr Pro Leu
            355                 360                 365
Ser Arg Gly Thr Ser Met Cys Lys Ser Gln Glu Glu Pro Leu Asn Thr
        370                 375                 380
Ile Ile Glu Lys Asp Asn Ile His Ile Phe Ser Gln Asn Lys Thr Val
385                 390                 395                 400
Thr Phe Glu Pro Phe Arg Met Asn Glu Glu Pro Met Lys Cys Asn Ile
            405                 410                 415
Asn Gly Glu Val Ala Asp Phe Ser Trp Gln Glu Ile Phe Glu Glu His
        420                 425                 430
Val Lys Pro Leu Glu Phe Pro Leu Ala Asp Val Asp Thr Val Ile Asn
            435                 440                 445
Asn Gln Leu His Val Asp Asn Phe Asn Asn Ser Ala Glu Lys Lys Lys
        450                 455                 460
His Val Glu Ile Ile Thr Leu Gly Thr Gly Ser Ala Leu Pro Ser Lys
465                 470                 475                 480
Tyr Arg Asn Val Val Ser Thr Leu Val Lys Val Pro Phe Thr Asp Ala
                485                 490                 495
Asp Gly Asn Thr Ile Asn Arg Asn Ile Met Leu Asp Ala Gly Glu Asn
            500                 505                 510
Thr Leu Gly Thr Ile His Arg Met Phe Ser Gln Leu Ala Val Lys Ser
            515                 520                 525
Ile Phe Gln Asp Leu Lys Met Ile Tyr Leu Ser His Leu His Ala Asp
        530                 535                 540
His His Leu Gly Ile Ile Ser Val Leu Asn Glu Trp Tyr Lys Tyr Asn
545                 550                 555                 560
Lys Asp Asp Glu Thr Ser Tyr Ile Tyr Val Val Thr Pro Trp Gln Tyr
                565                 570                 575
His Lys Phe Val Asn Glu Trp Leu Val Leu Glu Asn Lys Glu Ile Leu
            580                 585                 590
Lys Arg Ile Lys Tyr Ile Ser Cys Glu His Phe Ile Asn Asp Ser Phe
            595                 600                 605
Val Arg Met Gln Thr Gln Ser Val Pro Leu Ala Glu Phe Asn Glu Ile
        610                 615                 620
Leu Lys Glu Asn Ser Asn Gln Glu Ser Asn Arg Lys Leu Glu Leu Asp
625                 630                 635                 640
Arg Asp Ser Ser Tyr Arg Asp Val Asp Leu Ile Arg Gln Met Tyr Glu
                645                 650                 655
Asp Leu Ser Ile Glu Tyr Phe Gln Thr Cys Arg Ala Ile His Cys Asp
            660                 665                 670
Trp Ala Tyr Ser Asn Ser Ile Thr Phe Arg Met Asp Glu Asn Asn Glu
            675                 680                 685
```

```
His Asn Thr Phe Lys Val Ser Tyr Ser Gly Asp Thr Arg Pro Asn Ile
    690                 695                 700

Glu Lys Phe Ser Leu Glu Ile Gly Tyr Asn Ser Asp Leu Leu Ile His
705                 710                 715                 720

Glu Ala Thr Leu Glu Asn Gln Leu Leu Glu Asp Ala Val Lys Lys
                725                 730                 735

His Cys Thr Ile Asn Glu Ala Ile Gly Val Ser Asn Lys Met Asn Ala
                740                 745                 750

Arg Lys Leu Ile Leu Thr His Phe Ser Gln Arg Tyr Pro Lys Leu Pro
            755                 760                 765

Gln Leu Asp Asn Asn Ile Asp Val Met Ala Arg Glu Phe Cys Phe Ala
    770                 775                 780

Phe Asp Ser Met Ile Val Asp Tyr Glu Lys Ile Gly Glu Gln Gln Arg
785                 790                 795                 800

Ile Phe Pro Leu Leu Asn Lys Ala Phe Val Glu Glu Lys Glu Glu Glu
                805                 810                 815

Glu Asp Val Asp Asp Val Glu Ser Val Gln Asp Leu Glu Val Lys Leu
                820                 825                 830

Lys Lys His Lys Lys Asn
        835

<210> SEQ ID NO 53
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 53
attcagacag ttattatgga tgtccacgag gtctctaact gtgtggaatt agcccgcgta      60
cgctgcaggt cgac                                                       74

<210> SEQ ID NO 54
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 54
tccttttctt tctgttcacg gtgtcggtct cgtagactat atgcggagac acgcgatcga      60
tgaattcgag ctcg                                                       74

<210> SEQ ID NO 55
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 55
ctattgaata ggtttgaaaa actcataatt cagacagtta ttatg                     45

<210> SEQ ID NO 56
<211> LENGTH: 45
<212> TYPE: DNA
<213> ORGANISM: Artificial Sequence
<220> FEATURE:
<223> OTHER INFORMATION: Description of Artificial Sequence: primer
```

<400> SEQUENCE: 56
aactgccttc ttccgattta tataagatcc ttttctttct gttca   45

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 57
aagagttgtt cttagaaagg acggt   25

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 58
tgatctgctc attcaactct gttag   25

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 59
aaaaaggaat ctgaacaatc aaatg   25

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 60
tgccatacgt gaagagatat atgaa   25

<210> SEQ ID NO 61
<211> LENGTH: 402
<212> TYPE: DNA
<213> ORGANISM: Saccharomyces cerevisiae

<400> SEQUENCE: 61
atggattcaa tagatgaaca aattgctata aagcgaaaag aacttcagtc attacaaaag   60
ataaccagtt taacggatgg cttaaaaatt cagctaacag agttgaatga gcagatcaaa   120
gaaatgggaa tgaatgcgga ttcagtggcc caattgatga acaattggga ttctataata   180
aacaatatat cgcaagcaag tttgggatta ttgcaatatg cagagggtga ttatgagata   240
ggaccgtgga aagattctaa gaaaaaggaa tctgaacaat caaatgaaac aggtcttgaa   300
gcgcaagaaa atgataagaa tgatgaagat aatgatgagg atgaagatct ggtacccttg   360
ccggaaacaa tggtcagaat tagggtagat ggtaacgaat ga   402

<210> SEQ ID NO 62
<211> LENGTH: 133
<212> TYPE: PRT
<213> ORGANISM: Saccharomyces cerevisiae -continued

<400> SEQUENCE: 62

Met Asp Ser Ile Asp Glu Gln Ile Ala Ile Lys Arg Lys Glu Leu Gln
1               5                   10                  15

Ser Leu Gln Lys Ile Thr Ser Leu Thr Asp Gly Leu Lys Ile Gln Leu
            20                  25                  30

Thr Glu Leu Asn Glu Gln Ile Lys Glu Met Gly Met Asn Ala Asp Ser
        35                  40                  45

Val Ala Gln Leu Met Asn Asn Trp Asp Ser Ile Ile Asn Asn Ile Ser
    50                  55                  60

Gln Ala Ser Leu Gly Leu Leu Gln Tyr Ala Glu Gly Asp Tyr Glu Ile
65                  70                  75                  80

Gly Pro Trp Lys Asp Ser Lys Lys Lys Glu Ser Glu Gln Ser Asn Glu
                85                  90                  95

Thr Gly Leu Glu Ala Gln Glu Asn Asp Lys Asn Asp Glu Asp Asn Asp
            100                 105                 110

Glu Asp Glu Asp Leu Val Pro Leu Pro Glu Thr Met Val Arg Ile Arg
            115                 120                 125

Val Asp Gly Asn Glu
    130

<210> SEQ ID NO 63
<211> LENGTH: 31
<212> TYPE: PRT
<213> ORGANISM: Saccharomyces cerevisiae

<400> SEQUENCE: 63

Cys Gly Ser Cys Ser Leu Gly Asp Ala Phe Arg Cys Ser Gly Cys Pro
1               5                   10                  15

Tyr Leu Gly Leu Pro Ala Phe Lys Pro Gly Gln Pro Ile Asn Leu
            20                  25                  30

<210> SEQ ID NO 64
<211> LENGTH: 31
<212> TYPE: PRT
<213> ORGANISM: Homo sapiens

<400> SEQUENCE: 64

Cys Gly Asn Cys Tyr Leu Gly Asp Ala Phe Arg Cys Ala Ser Cys Pro
1               5                   10                  15

Tyr Leu Gly Met Pro Ala Phe Lys Pro Gly Glu Lys Val Leu Leu
            20                  25                  30

ESSENTIAL GENES OF YEAST AS TARGETS FOR ANTIFUNGAL AGENTS, HERBICIDES, INSECTICIDES AND ANTI-PROLIFERATIVE DRUGS

FIELD OF THE INVENTION

The present invention relates to genes in *Saccharomyces cerevisiae* which are essential for germination and proliferation of *S. cerevisiae* and using the identified genes or their encoded proteins as targets for highly specific antifungal agents, insecticides, herbicides and anti-proliferation drugs. Specifically, the present invention relates to essential genes YFR003C, YGR277C, YGR278W, YKR071C, YKR079C, and YKR083C. The present invention provides antisense molecules and ribozymes comprising sequences complementary to the sequences of mRNAs of essential genes that function to inhibit the essential genes. The present invention also provides neutralizing antibodies to proteins encoded by essential genes that bind to and inactivate the essential gene products.

BACKGROUND OF THE INVENTION

Fungal pathogens are responsible for a large number of diseases in humans, animals and plants. Fungal diseases often occur as opportunistic infections in humans who have a suppressed immune system, such as in patients with AIDS, leukemia, or diabetes mellitus, or in patients receiving immunosuppressive drugs or chemotherapy. Fungal infections are a significant problem in veterinary medicine as well, and fungal diseases also affect plant crops which are critical to the agricultural industry. Since fungi are eukaryotic cells, many metabolic pathways and genes of fungi are similar to those of mammalian and/or plant cells. Therefore, treatment of fungal diseases is frequently hindered because antifungal agents are often toxic to mammalian or plant cells.

The most widely used class of antifungal compounds in human medicine is the family of azole compounds, which are used to treat both systemic and topical fungal infections. The common target of all azole compounds is the cytochrome P450 lanosterol 14α-demethylase. Lanosterol demethylase is an essential gene required for the intracellular biosynthesis of sterols, which are critical components of biological membranes. In *S. cerevisiae,* the ERG11 gene encodes lanosterol demethylase. Although azole compounds are effective antifungal inhibitors, the enzymes involved in sterol biosynthesis are highly conserved in all eukaryotic cells. Lanosterol demethylases from all eukaryotic cells, including human, exhibit a high degree of nucleotide sequence identity, as shown in FIG. 9. Thus, the azoles inhibit lanosterol demethylase from the host cell as well as lanosterol demethylase from yeast, which causes undesirable side effects upon administration. These side effects may be especially deleterious in patients who are already immunocompromised because it may make them more susceptible to other opportunistic infections. Therefore, the identification of new targets for new antifungal compounds with fewer side effects is an active area of clinical research.

The use of herbicides and insecticides are critical in agriculture to ensure an adequate food supply for a growing world population. One problem with current herbicides and insecticides is that agricultural pests often become resistant to them. Another problem is that many pesticides currently in use are highly toxic to farmworkers working in the fields, humans or animals who eat the food produced by the treated crops, or other plant and animal species that come in contact with the pesticide through soil, water or air contamination. Thus, new herbicides and insecticides that are less toxic to humans and animals and that are effective against resistant species of weeds and insects are desirable.

Drugs to prevent proliferation are critical in the treatment of diseases characterized by uncontrolled or poorly controlled cell proliferation. For instance, anti-proliferation drugs are used to treat many types of cancer, benign tumors, psoriasis, and to prevent restenosis after angioplasty. Identifying new targets for anti-proliferation drugs is an active area of research because different cells, especially malignant cells, vary dramatically in their responses to particular anti-proliferation drugs. It is often the case that an anti-proliferation drug will inhibit cell proliferation in one cell type but be ineffective in another cell type. Thus, the identification of new anti-proliferation drugs, directed against novel targets, provides a larger arsenal from which a physician can treat a patient with a cell proliferation disorder.

As discussed above, identifying new targets and compounds for antifungal drugs, herbicides, insecticides and anti-proliferation agents is critical for improvements in agriculture and in veterinary and human health. One promising avenue for identifying targets and compounds is the information contained within the complete genomic sequence of baker's yeast, *Saccharomyces cerevisiae. S. cerevisiae* has long been used as a model for eukaryotic cells. *S. cerevisiae* shares many basic cellular functions with other eukaryotic cells, including vertebrate, insect and plant cells. Furthermore, it is easy to grow *S. cerevisiae* and to manipulate its genes. Many of the genes of *S. cerevisiae* are specific to *S. cerevisiae* or to fungi in general, and have no homologs in other eukaryotic organisms. However, many genes from *S. cerevisiae* exhibit significant homology to genes in other organisms, including mammals, plants and insects.

The sequencing of the *S. cerevisiae* genome marked the first complete, ordered set of genes from a eukaryotic organism. The sequencing of *S. cerevisiae* revealed the presence of over 6,000 genes on 16 chromosomes (Mewes et al. (1997) *Nature* 387:7–65; Goffeau et al. (1996) *Science* 274:546–67). The sequence of the roughly 6,000 ORFs in the yeast genome is compiled in the Saccharomyces Genome Database (SGD). The SGD provides Internet access to the complete genomic sequence of *S. cerevisiae,* ORFs, and the putative polypeptides encoded by these ORFs. The SGD can be accessed via the World Wide Web. A gazetteer and genetic and physical maps of *S. cerevisiae* is found in Mewes et al., 1997. References therein also contain the sequence of each chromosome of *S. cerevisiae.*

Approximately half of the putative proteins encoded by the open reading frames (ORF) identified in the sequencing of the yeast genome have no known function. The function of many others is assigned only by structural similarity to homologous proteins in other cell types. Thus, the role of many genes in *S. cerevisiae* is unknown. However, in order to use the information gathered from the sequencing of *S. cerevisiae* most efficiently for identifying targets or compounds for antifungal and anti-proliferation drugs, as well as herbicides and insecticides, the function of the many *S. cerevisiae* genes must be identified.

Citation of a reference herein shall not be construed as indicating that such reference is prior art to the present invention.

SUMMARY OF THE INVENTION

This invention provides genes in *S. cerevisiae,* a budding yeast, which are essential for germination or proliferation.

The essential genes are useful as targets for new antifungal agents, insecticides, herbicides and anti-proliferation drugs. Specifically, the invention provides yeast essential genes YFR003C, YGR277C, YGR278W, YKR071C, YKR079C, and YKR083C.

The invention provides a method of comparing the sequences of the essential *S. cerevisiae* genes to sequences from plants, insects and vertebrates, including humans and non-human mammals, to determine whether the essential *S. cerevisiae* genes have any homologs in these higher eukaryotes. If no human or mammalian homologs exist, the *S. cerevisiae* genes themselves, or the proteins which these genes encode, provide targets for the design or discovery of highly specific antifungal agents for use in human patients or in veterinary settings. Similarly, if no plant homologs exist, the *S. cerevisiae* genes or their encoded proteins provide targets for the production of highly specific antifungal agents for plants. The advantage of the method is that the new antifungal agents would be expected to have few or no side effects in human or non-human mammals or in plants. The invention further encompasses methods of identifying antifungal targets from fungi other than *S. cerevisiae*, including Aspergillus and Candida.

The invention also encompasses methods of identifying targets for herbicides and insecticides when an essential *S. cerevisiae* gene has either or both a plant or insect homolog, respectively. The method comprises the steps of identifying essential *S. cerevisiae* genes and comparing the sequence of the essential *S. cerevisiae* gene to sequences from plants and/or insects. If a plant or insect homolog exists, the method comprises the step of determining whether the plant or insect homolog is critical to growth or proliferation. If the plant or insect homolog is critical for growth or proliferation, the insect, plant or yeast gene and/or its encoded protein can be used as targets for the design and discovery of new herbicides and insecticides.

The invention also includes a method of identifying targets for anti-proliferation drugs in cases in which an essential *S. cerevisiae* gene has a human or non-human mammalian homolog. After identification of an essential *S. cerevisiae* gene, the method comprises determining whether a human or non-human mammalian homolog exists. The method further comprises the step of determining if the mammalian or human homolog is important for cell proliferation. If the identified human or mammalian gene is important for cell proliferation, the human, mammalian or yeast gene or its encoded protein can be used as targets in the design of new anti-proliferation drugs.

An essential gene from *S. cerevisiae*, YFR003C (FIG. 4) has been identified. The polypeptide encoded by this gene (FIG. 5), Yfr003cp has very weak homolgs in *C. elegans* and *C. albicans*, and no homology to any known plant, insect, mammalian or other vertebrate polypeptide (FIGS. 6–8). The invention thus provides the polynucleotide sequence of YFR003C (FIG. 4, SEQ ID NO: 11) and vectors and host cells comprising YFR003C for use in methods of identifying, designing and discovering highly specific antifungal agents. The invention also provides the amino acid sequence of Yfr003cp (FIG. 5, SEQ ID NO: 12), a method of recombinantly producing Yfr003cp for use as a target, and a method for producing antibodies directed against Yfr003cp.

A number of other essential genes in *S. cerevisiae* have been identified, including YGR277C (FIG. 12, SEQ ID NO: 21), YGR278W (FIG. 17, SEQ ID NO: 31) YKR071C (FIG. 22, SEQ ID NO: 41), YKR079C (FIG. 29, SEQ ID NO: 51) and YKR083C (FIG. 34, SEQ ID NO: 61). These genes were previously identified only as hypothetical ORFs and had no known function. The polypeptide encoded by YGR277C (FIG. 13, SEQ ID NO: 22) has weak homologs (Type 2 homologs, defined below) in Arabidopsis, *S. pombe*, Pyrococcus, Methanococcus, and Methanobacterium (FIG. 14). The polypeptide encoded by YGR278W (FIG. 18, SEQ ID NO: 32) has strong homologs (Type 1 homologs, defined below) from *S. pombe* and *C. elegans*, and a weak homolog from its own genome (FIG. 19). The polypeptide encoded by YKR071C (FIG. 23, SEQ ID NO: 42) has a weak homolog in *S. pombe* (FIG. 24). In addition, a 30 amino acid polypeptide encoded by YKR071C has 70% sequence identity (86% sequence homology) with a 30 amino acid polypeptide that is an unknown gene product from *H. sapiens* (FIG. 25). Furthermore, the polypeptide encoded by YKR071C shows weak sequence similarity with the human chemokine STCP-1 (FIG. 26). The polypeptide encoded by YKR079C (FIG. 30, SEQ ID NO: 51) has a strong homolog in *S. pombe*, and weak homologs in *C. elegans*, *S. pombe*, Archaeoglobus, Methanococcus, Pyrococcus, and Methanobacterium (FIG. 31). The polypeptide encoded by YKR083C (FIG. 35, SEQ ID NO: 62) exhibits no homology to any sequences in any of the databases that were searched (FIG. 36).

The invention provides the polynucleotide sequences of these ORFs and vectors and host cells comprising these ORFs for use in methods of identifying, designing and discovering highly specific antifungal agents. The invention also provides a methods of recombinantly producing the protein encoded these ORFs for use as a target in methods of identifying, designing and discovering highly specific antifungal agents and for producing antibodies directed against the encoded protein.

Highly specific antifungal compounds encompassed by this invention include antisense polynucleotides that target RNAs transcribed from YFR003C, YGR277C, YGR278W, YKR071C, YKR079C, and YKR083C. Highly specific antifungal compounds also include ribozymes that cleave YFR003C, YGR277C, YGR278W, YKR071C, YKR079C, or YKR083C polynucleotides. The invention also encompasses antibodies which bind to and neutralize Yfr003cp or the proteins encoded by the YGR277C, YGR278W, YKR071C, YKR079C, and YKR083C ORFs. The invention also encompasses small organic molecules which inhibit Yfr003cp activity or the activity of the YGR277C, YGR278W, YKR071C, YKR079C, or YKR083C encoded proteins. Also contemplated are methods for specific inhibition of transcription of YFR003C, YGR277C, YGR278W, YKR071C, YKR079C, or YKR083C by inhibiting specific transcriptional factors or combinations of such factors. The invention also provides methods of isolating highly specific antifungal compounds using Yfr003cp or the proteins encoded by one of the YGR277C, YGR278W, YKR071C, YKR079C, and YKR083C ORFs.

BRIEF DESCRIPTION OF THE DRAWINGS

FIG. 3. The ten oligonucleotides used as PCR primers for the construction and analysis of the YFR003C knock-out mutant. Four of the primers were used to construct the DNA molecule use to transform yeast: UPTAG (SEQ ID NO: 1), DOWNTAG (SEQ ID NO: 2), Upstream45 (SEQ ID NO: 3), and Downstream45 (SEQ ID NO: 4). The other six primers were used to analyze the mutant allele: A (SEQ ID NO: 5), B (SEQ ID NO: 6), C (SEQ ID NO: 7), D (SEQ ID NO: 8), KanB (SEQ ID NO: 9), and KanC (SEQ ID NO: 10).

FIG. 4. Nucleotide sequence of the coding region of the *S. cerevisiae* gene YFR003C (SEQ ID NO: 11). There are 468 nucleotides including the start codon (ATG, in bold) and the stop codon (TGA, in bold).

FIG. 5. Amino acid sequence of the *S. cerevisiae* protein Yfr003cp (SEQ ID NO: 12) as predicted by the nucleotide sequence of the YFR003C gene. The gene encodes a protein of 155 amino acids.

FIG. 6. Blastp (Altschul et al. (1997) *Nucleic Acids Res.* 25:3389–402) search results of the yeast protein Yfr003cp against the amino acid sequences in the Swiss protein database swissprot shows that this polypeptide has very weak homologs in *C. elegans* and *C. albicans*.

FIG. 7. Blast (Altschul et al., 1997) alignment of Yfr003cp with proteins of *C. elegans* shows that Yfr003cp has weak homologs in *C. elegans*.

FIG. 8. Blast (Altschul et al., 1997) alignment of Yfr003cp with proteins of *C. albicans* shows that Yfr003cp has a weak homolog in *C. albicans*.

FIG. 9. Blastp (Altschul et al., 1997) search results of the yeast protein Erg11p (cytochrome P450 lanosterol 14α-demethylase) against the Swiss protein database. Cytochrome P450 lanosterol 14α-demethylase proteins from numerous species show significant sequence homologies.

FIG. 11. The ten oligonucleotides used as PCR primers for the construction and analysis of the YGR277C knock-out mutant. Four of the primers were used to construct the DNA molecule use to transform yeast: UPTAG (SEQ ID NO: 13), DOWNTAG (SEQ ID NO: 14), Upstream45 (SEQ ID NO: 15), and Downstream45 (SEQ ID NO: 16). The other six primers were used to analyze the mutant allele: A (SEQ ID NO: 17), B (SEQ ID NO: 18), C (SEQ ID NO: 19), D (SEQ ID NO: 20), KanB (SEQ ID NO: 9), and KanC (SEQ ID NO: 10).

FIG. 12. Nucleotide sequence of the coding region of the *S. cerevisiae* gene YGR277C (SEQ ID NO: 21). The gene comprises 918 nucleotides of coding sequence including the start codon (ATG, in bold) and the stop codon (TAA, in bold).

FIG. 13. The predicted amino acid sequence of the *S. cerevisiae* protein encoded by the YGR277C gene, Ygr277cp (SEQ ID NO: 22). The gene encodes a protein of 305 amino acids.

FIG. 14. Blastp (Altschul et al., 1997) search results of the yeast protein Ygr277cp against the NCBI non-redundant database Ygr277cp has Type 2 homologs in Arabidopsis, *S. pombe*, Pyrococcus, Methanococcus, and Methanobacterium.

FIG. 16. The ten oligonucleotides used as PCR primers for the construction and analysis of the YGR278W knock-out mutant. Four of the primers were used to construct the DNA molecule use to transform yeast: UPTAG (SEQ ID NO: 23), DOWNTAG (SEQ ID NO: 24), Upstream45 (SEQ ID NO: 25), and Downstream45 (SEQ ID NO: 26). The other six primers were used to analyze the mutant allele: A (SEQ ID NO: 27), B (SEQ ID NO: 28), C (SEQ ID NO: 29), D (SEQ ID NO: 30), KanB (SEQ ID NO: 9), and KanC (SEQ ID NO: 10).

FIG. 17. Nucleotide sequence of the coding region of the *S. cerevisiae* gene YGR278W (SEQ ID NO: 31). The gene comprises 1,734 nucleotides of coding sequence, including the start codon (ATG, in bold) and the stop codon (TGA, in bold).

FIG. 18. The predicted amino acid sequence of the *S. cerevisiae* protein encoded by the YGR278W gene, Ygr278wp (SEQ ID NO: 32). The gene encodes a protein of 577 amino acids.

FIG. 19. Blastp (Altschul et al., 1997) search results of the yeast protein Ygr278wp against the NCBI non-redundant database, supra. Ygr278wp has Type 1 homologs in *S. pombe* and *C. elegans*, and a weak homolog in its own genome.

FIG. 21. The ten oligonucleotides used as PCR primers for the construction and analysis of the YKR071C knock-out mutant. Four of the primers were used to construct the DNA molecule use to transform yeast: UPTAG (SEQ ID NO: 33), DOWNTAG (SEQ ID NO: 34), Upstream45 (SEQ ID NO: 35), and Downstream45 (SEQ ID NO: 36). The other six primers were used to analyze the mutant allele: A (SEQ ID NO: 37), B (SEQ ID NO: 38), C (SEQ ID NO: 39), D (SEQ ID NO: 40), KanB (SEQ ID NO: 9), and KanC (SEQ ID NO: 10).

FIG. 22. Nucleotide sequence of the coding region of the S. cerevisiae gene YKR071C (SEQ ID NO: 41). The gene comprises 1,047 nucleotides of coding sequence, including the start codon (ATG, in bold) and the stop codon (TAA, in bold).

FIG. 23. The predicted amino acid sequence of the S. cerevisiae protein encoded by the YKR071C gene, Ykr071cp (SEQ ID NO: 42). The gene encodes a protein of 348 amino acids.

FIG. 24. Blastp (Altschul et al., 1997) search results of the yeast protein Ykr071cp against the NCBI non-redundant database, supra. Ykr071cp has a weak homolog in S. pombe.

FIG. 25. Amino acid sequence alignment of a portion of Ykr071cp (SEQ ID NO: 63) and an EST from an unknown gene product of H. sapiens (SEQ ID NO: 64). This is the closest match to Ykr071cp using the tblastn algorithm (Altschul et al., 1997) and the EST database at the NCBI with a score of 6e-08.

FIG. 26. Blast (Altschul et al., 1997) alignment of Ykr071cp with proteins of H. sapiens shows that H. sapiens chemokine STCP-1 is a weak homolog of Ykr071cp.

FIG. 28. The ten oligonucleotides used as PCR primers for the construction and analysis of the YKR079C knock-out mutant. Four of the primers were used to construct the DNA molecule use to transform yeast: UPTAG (SEQ ID NO: 43), DOWNTAG (SEQ ID NO: 44), Upstream45 (SEQ ID NO: 45), and Downstream45 (SEQ ID NO: 46). The other six primers were used to analyze the mutant allele: A (SEQ ID NO: 47), B (SEQ ID NO: 48), C (SEQ ID NO: 49), D (SEQ ID NO: 50), KanB (SEQ ID NO: 9), and KanC (SEQ ID NO: 10).

FIG. 29. Nucleotide sequence of the coding region of the S. cerevisiae gene YKR079C (SEQ ID NO: 51). The gene comprises 2,517 nucleotides of coding sequence, including the start codon (ATG, in bold) and the stop codon (TAG, in bold).

FIG. 30. The predicted amino acid sequence of the S. cerevisiae protein encoded by the YKR079C gene, Ykr079cp (SEQ ID NO: 52). The gene encodes a protein of 838 amino acids.

FIG. 31. Blastp (Altschul et al., 1997) search results of the yeast protein Ykr079cp against the NCBI non-redundant database, supra. Ykr079cp has a Type 1 homolog in S. pombe, and Type 2 homologs in C. elegans, S. pombe, Archaeoglobus, Methanococcus, Pyrococcus, and Methanobacterium.

FIG. 33. The ten oligonucleotides used as PCR primers for the construction and analysis of the YKR083C knock-out mutant. Four of the primers were used to construct the DNA molecule use to transform yeast: UPTAG (SEQ ID NO: 53), DOWNTAG (SEQ ID NO: 54), Upstream45 (SEQ ID NO: 55), and Downstream45 (SEQ ID NO: 56). The other six primers were used to analyze the mutant allele: A (SEQ ID NO: 57), B (SEQ ID NO: 58), C (SEQ ID NO: 59), D (SEQ ID NO: 60), KanB (SEQ ID NO: 9), and KanC (SEQ ID NO: 10).

FIG. 34. Nucleotide sequence of the coding region of the S. cerevisiae gene YKR083C (SEQ ID NO: 61). The gene comprises 402 nucleotides of coding sequence, including the start codon (ATG, in bold) and the stop codon (TGA, in bold).

FIG. 35. The predicted amino acid sequence of the S. cerevisiae protein encoded by the YKR083C gene, Ykr083cp (SEQ ID NO: 62). The gene encodes a protein of 133 amino acids.

FIG. 36. Blast-p (Altschul et al., 1997) search results of the yeast protein Ykr083cp against the NCBI non-redundant database, supra. Ykr083cp has no significant homology to any protein in the database.

DETAILED DESCRIPTION OF THE INVENTION

Goals of the Invention

Figure 1:
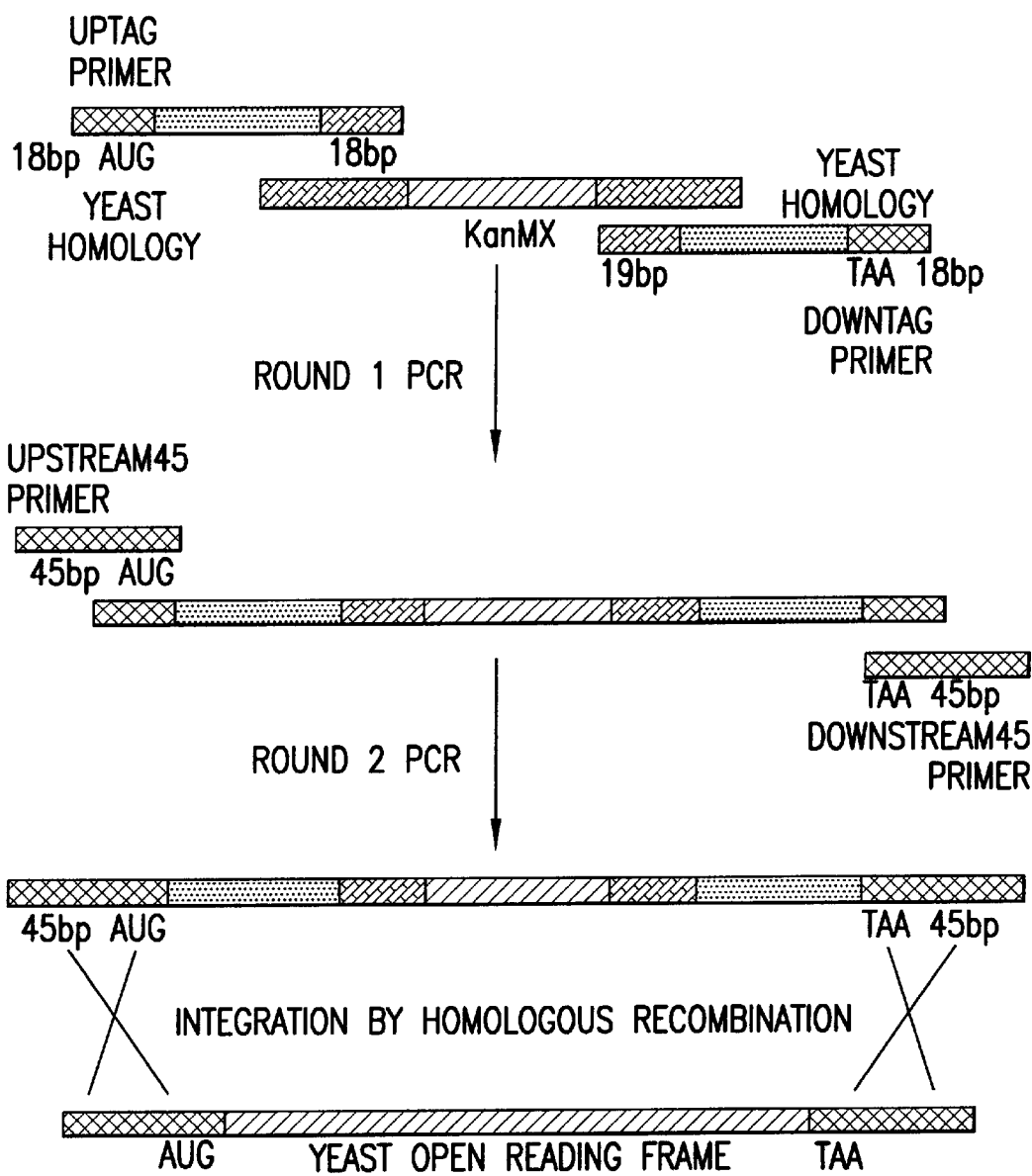
FIG. 1. A one-step, PCR based strategy for the construction of a yeast strain containing a specific gene deletion, e.g., a "knock-out" mutation (Rothstein (1991) *Methods Enzymol.* 194:281–301). Two rounds of PCR are utilized to produce a DNA molecule containing the KanMX marker flanked by 45 basepairs of the yeast sequence immediately upstream of the start codon of the target gene and 45 basepairs of the yeast sequence immediately downstream of the stop codon of the target gene. In round 1, primer pair UPTAG and DOWNTAG are used to produce a DNA molecule having 18 basepairs of yeast sequence upstream of the start codon of the target gene and 19 basepairs of yeast sequence downstream of the stop codon of the target gene at the ends of the DNA molecule. In round 2, the primer pair UPSTREAM45 and DOWNSTREAM45 are used to produce a DNA molecule having 45 base pairs of the yeast sequence both upstream and downstream of the target gene at the end of the DNA molecule. The DNA is then transformed into yeast (Ito et al. (1983) *J Bacteriol.* 153:163–68; Schiestl & Gietz (1989) *Curr. Genet.* 16: 339–46) where the integration event is targeted to the correct locus by homologous recombination. The resulting mutant allele is a precise replacement of the targeted open reading frame with the KanMX marker (Wach et al. (1994) *Yeast* 10:1793–1808). The KanMX marker confers resistance to the drug G-418.

The essential genes from S. cerevisiae provide targets for the design or discovery of antifungal agents, herbicides and insecticides, and anti-proliferation drugs, that can be used in a variety of therapeutic, veterinary and agricultural settings.

Genes demonstrated to be essential in S. cerevisiae can be used to define a number of different categories of targets. Essential genes of S. cerevisiae that do not have plant and/or mammalian homologs can be used as targets for the design and discovery of highly specific antifungal agents. Alternatively, essential S. cerevisiae genes that have insect or plant homologs can be used as targets for the preparation of insecticides and herbicides, respectively. Lastly, essential S. cerevisiae genes that have mammalian homologs can be used as targets for the design of anti-proliferative agents, such as those that can be used in the treatment of psoriasis, prevention of restenosis after angioplasty, benign tumors and cancer, for example. These groups may not be mutually exclusive. For instance, an essential S. cerevisiae gene may have a plant homolog but no mammalian homolog. The gene or the protein it encodes may be used as a target to identify potential antifungal agents for mammals as well as a target to isolate herbicides which will be safe to mammals. Similarly, an essential S. cerevisiae gene may have plant, insect and mammalian homologs, and may be used as a target for the design or discovery of potential herbicides, insecticides and mammalian anti-proliferative agents.

A primary goal of the instant invention is thus to identify a new collection of antifungal targets for rational drug design based upon the sequence and function of S. cerevisiae genes.

The rationale underlying the identification of S. cerevisiae genes encoding new antifungal targets described here is two-fold. First, the genes encoding the potential antifungal targets must be essential for germination or vegetative growth. If a gene is essential, an inhibitor of the gene or its encoded protein will prevent germination or inhibit the growth of the cell. Second, the gene encoding the potential antifungal target preferably does not have a human or non-human mammalian homolog. If a target is to be useful for production of agricultural antifungal agents, it is preferable that the gene does not have a plant homolog. If the genes of a mammal or plant do not encode a protein that is homologous to the protein encoded by the essential S. cerevisiae gene, the targets defined by the essential S. cerevisiae genes have the potential to be highly fungal specific. Alternatively, if the target exhibits some homology with mammalian or plant proteins, antifungal agents may be designed to exploit the differences between the yeast target and the homologous mammalian or plant proteins to produce a specific antifungal agent. Finally, even if there is substantial homology between an essential S. cerevisiae gene or encoded protein and a mammalian or plant gene or encoded protein, the invention encompasses methods in which the S. cerevisiae gene or the protein target encoded by the gene can be used in the design or discovery of antifungal agents that can be selected or designed for few side effects in host organisms.

A second goal of the instant invention is the use of essential S. cerevisiae genes to identify novel targets for new herbicides and insecticides.

Genes that are homologous between S. cerevisiae and plants or insect not only exhibit sequence similarities but often exhibit functional similarities as well. Thus, if an S. cerevisiae gene is essential and is homologous to an insect or plant gene, there is a reasonable likelihood that the homologous insect or plant gene will be important for growth of the insect or plant as well.

Once a homologous gene to an essential S. cerevisiae gene has been identified, a number of techniques can be used to determine whether the homologous insect or plant gene is important or essential for insect or plant growth. For instance, one could knock out the homologous gene using standard genetic techniques in Drosophila, a well-characterized insect system, to determine whether the homologous insect gene is critical for cell proliferation in an insect. Similarly, the homologous gene could be knocked out in the well-characterized plant system Arabidopsis to determine whether the homologous plant gene is critical for germination or proliferation in a plant. If the homologous insect or plant gene is critical for growth and/or proliferation, the gene or its encoded protein can be used as a target for the design or discovery of insecticides or herbicides. One advantage of this approach is that previously unknown targets can be identified. Another advantage is that insecticides and herbicides designed to interact with certain specific targets may have fewer toxic side effects or be less likely to promote the development of resistance by a pest.

A third goal of the instant invention is to provide targets for the design of anti-proliferation drugs for mammals, especially humans.

As discussed above, genes from S. cerevisiae often have homologs in other eukaryotic organisms, including humans. Thus, if a gene is essential for proliferation in S. cerevisiae, there is a reasonable likelihood that the gene is also important for cell proliferation in vertebrates, including human and non-human mammals. Although many partial and full-length cDNAs have been identified in humans via expressed sequence tags (ESTS) and other large-scale sequencing schemes, the function of most of these sequenced cDNAs is as yet unknown. Once a vertebrate, preferably a human or non-human mammalian, gene homologous to an essential S. cerevisiae gene is identified, a variety of techniques can be used to determine whether the homologous gene is important for cell proliferation. For example, antisense molecules or ribozymes complementary to the vertebrate gene can be produced to determine if the inhibition of the gene inhibits cell proliferation. Alternatively, the gene can be deleted ("knocked out") in a cell line, a mouse or another transgenic organism.

If the homologous mammalian gene is critical for proliferation, the gene or its encoded protein can be used as a target for the design or discovery of anti-proliferation drugs. One advantage of this method is that genes previously unknown to be important for cell proliferation can be targeted. Anti-proliferation drugs directed against these targets may be more effective than those currently available, or they may be used in conjunction with currently available drugs to inhibit cell proliferation.

By systematically disrupting certain ORFs in the yeast genome or a portion thereof and determining whether the gene is essential to S. cerevisiae germination or vegetative growth, essential genes have been identified.

Second, the invention encompasses analyzing the collection of essential genes for sequence similarity to human, other mammalian and vertebrate, insect and plant genes, such that the genes or the proteins they encode can be used as targets for antifungal targets, insecticides, herbicides, or anti-proliferation drugs, as discussed above. This large scale analysis of a collection of essential genes permits the determination of whether there are common motifs that can be exploited in antifungal agents. The method also allows one to identify essential genes included in the same metabolic or signaling pathway, such that a number of genes or encoded proteins within a single pathway can be targeted by a combination of antifungal agents. A combination of antifungal agents directed against many targets may be more effective than an antifungal agent directed against a single target.

Although this invention is exemplified using S. cerevisiae, this method can be practiced using a number of other fungal genera. These include the human pathogens such as Aspergillus, Candida, Neurospora, and Trichoderma. In addition, plant pathogens such as Fusarium can be targeted as well. A large number of genes, as well as parts of some of these fungal genomes other than *S. cerevisiae,* have been cloned and methods of disrupting genes in these fungi are also known.

According to the present invention, newly identified essential genes are YFR003C, YGR277C, YGR278W, YKR071C, YKR079C, and YKR083C.

Definitions and General Techniques

Unless otherwise defined, all technical and scientific terms used herein have the meaning as commonly understood by one of ordinary skill in the art to which this invention belongs. The practice of the present invention employs, unless otherwise indicated, conventional techniques of chemistry, molecular biology, microbiology, recombinant DNA, genetics and immunology. See, e.g., Maniatis et al. (1982) *Molecular Cloning, A Laboratory Manual,* 2d ed., Cold Spring Harbor Laboratory, Cold Spring Harbor, N.Y.; Sambrook et al. (1989) *Molecular Cloning: A Laboratory Manual* (Cold Spring Harbor, N.Y.: Cold Spring Harbor Laboratory Press); Ausubel et al. (1992) *Current Protocols in Molecular Biology* (New York: John Wiley & Sons); Guthrie & Fink (1991) *Methods Enzymol.* 194:1–863.

An "isolated" protein or polypeptide is one that has been separated from naturally associated components that accompany it in its native state. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art. A "protein" as used herein can be a peptide or polypeptide.

A "functional fragment" of a protein is any portion of the amino acid sequence that retains a functional activity of the protein, including but not limited to biological activity (e.g. ability to rescue a mutant in the gene encoding the protein so as to provide yeast growth or germination, immunogenicity, antigenicity, etc.)

A monomeric protein is "substantially pure," "substantially homogeneous" or "substantially purified" when at least about 60 to 75% of a sample exhibits a single polypeptide sequence. A substantially pure protein will typically comprise about 60 to 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "essential" refers to a gene that encodes a gene product whose function is required for vegetative growth or germination. An essential gene may be identified by a complete loss-of-function mutation (a knockout) of the gene which prevents yeast vegetative growth or germination on rich medium. However, a complete loss-of-function mutation is not the only way to identify an essential gene in yeast. An essential gene may also be identified by a non-null allele of the gene wherein the non-null allele encodes a protein with a sufficiently reduced biochemical activity that the protein is insufficient to meet the essential function required by the yeast, with the result that yeast vegetative growth or germination is prevented. For example, a non-null allele may be a gene having a point mutation at the active site of an enzyme. Finally, there are a number of genes in yeast that may be essential but which are duplicated in the yeast genome, such that there are multiple copies of a gene that encode proteins with the same function. Methods of identifying whether duplicate genes are essential are defined below in "Methods to Identify Essential Yeast Genes." Thus, the definition of essential genes also includes those duplicate genes in which the function of at least one copy of the duplicate gene is required for yeast vegetative growth or germination.

A *S. cerevisiae* protein has "homology" or is "homologous" to a protein from another organism if the encoded amino acid sequence of the yeast protein has a similar sequence to the encoded amino acid sequence of a protein of a different organism. Alternatively, a *S. cerevisiae* protein may have homology or be homologous to another *S. cerevisiae* protein if the two proteins have similar amino acid sequences. Although two proteins are said to be "homologous," this does not imply that there is necessarily an evolutionary relationship between the proteins. Instead, the term "homologous" is defined to mean that the two proteins have similar amino acid sequences. In addition, although in many cases proteins with similar amino acid sequences will have similar functions, the term "homologous" does not imply that the proteins must be functionally similar to each other.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al. (1994) *Methods in Molecular Biology* 24:307–31).

The following six groups each contain amino acids that are conservative substitutions for one another:

1) Alanine (A), Serine (S), Threonine (T);
2) Aspartic Acid (D), Glutamic Acid (E);
3) Asparagine (N), Glutamine (Q);
4) Arginine (R), Lysine (K);
5) Isoleucine (I), Leucine (L), Methionine (M), Valine (V), and
6) Phenylalanine (F), Tyrosine (Y), Tryptophan (W).

Sequence homology for polypeptides, which is also referred to as sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof.

A preferred algorithm when comparing a *S. cerevisiae* sequence to a database containing a large number of sequences from different organisms is the computer program BLAST, especially blastp or tblastn (Altschul et al., 1997). Preferred parameters for blastp are:

| | |
|---|---|
| Expectation value: | 10 (default) |
| Filter: | seg (default) |
| Cost to open a gap: | 11 (default) |
| Cost to extend a gap: | 1 (default |
| Max. alignments: | 100 (default) |
| Word size: | 11 (default) |
| No. of descriptions: | 100 (default) |
| Penalty Matrix: | BLOWSUM62 |

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms using a *S. cerevisiae* query sequence, it is preferable to compare amino acid sequences. Comparison of amino acid sequences is preferred to comparing nucleotide sequences because *S. cerevisiae* has significantly different codon usage compared to mammalian or plant codon usage.

Database searching using amino acid sequences can be measured by algorithms other than blastp known in the art. For instance, polypeptide sequences can be compared using Fasta, a program in GCG Version 6.1. Fasta provides alignments and percent sequence identity of the regions of the best overlap between the query and search sequences (Pearson (1990) *Methods in Enzymology* 183:63–98). For example, percent sequence identity between amino acid sequences can be determined using Fasta with its default parameters (a word size of 2 and the PAM250 scoring matrix), as provided in GCG Version 6.1.

The invention envisions two general types of polypeptide "homologs." Type 1 homologs are strong homologs. A comparison of two polypeptides that are Type 1 homologs would result in a blastp score of less than $1 \times 10^{-40}$, using the blastp algorithm and the parameters listed above. The lower the blastp score, that is, the closer it is to zero, the better the match between the polypeptide sequences. For instance, yeast lanosterol demethylase, which is a common target of antifungal agents, as discussed above, has a Type 1 homolog in humans. Comparison of yeast and human lanosterol demethylases produces a blastp score of $1 \times 10^{-86}$.

Type 2 homologs are weaker homologs. A comparison of two polypeptides that are Type 2 homologs would result in a blastp score of between $1 \times 10^{-40}$ and $1 \times 10^{-10}$, using the Blast algorithm and the parameters listed above. One having ordinary skill in the art will recognize that other algorithms can be used to determine weak or strong homology.

The terms "no substantial homology" or "no human (or mammalian, vertebrate, insect or plant) homolog" refers to a yeast polypeptide sequence which exhibits no substantial sequence identity with a polypeptide sequence from human, non-human mammals, other vertebrates, insects or plants. A comparison of two polypeptides which have no substantial homology to one another would result in a blastp score of greater than $1 \times 10^{-10}$, using the Blast algorithm and the parameters listed above. One having ordinary skill in the art will recognize that other algorithms can be used to determine whether two polypeptides demonstrate no substantial homology to each other.

A polypeptide "fragment," "portion" or "segment" refers to a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

A polypeptide "mutein" refers to a polypeptide whose sequence contains substitutions, insertions or deletions of one or more amino acids compared to the amino acid sequence of the native or wild type protein. A mutein has at least 50% sequence homology to the wild type protein, preferred is 60% sequence homology, more preferred is 70% sequence homology. Most preferred are muteins having 80%, 90% or 95% sequence homology to the wild type protein, in which sequence homology is measured by any common sequence analysis algorithm, such as Gap or Bestfit.

A "derivative" refers to polypeptides or fragments thereof that are substantially homologous in primary structural sequence but which include, e.g., in vivo or in vitro chemical and biochemical modifications or which incorporate unusual amino acids. Such modifications include but are not limited to, for example, acetylation, carboxylation, phosphorylation, glycosylation, ubiquitination, labeling, e.g., with radionuclides, and various enzymatic modifications, or conservative substitutions, as will be readily appreciated by those well skilled in the art. A variety of methods for labeling polypeptides and of substituents or labels useful for such purposes are well known in the art, and include radioactive isotopes such as $^{125}I$, $^{32}P$, $^{35}S$, and $^{3}H$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See Ausubel et al., 1992.

The term "fusion protein" refers to polypeptides comprising polypeptides or fragments bound via a peptide bond to heterologous amino acid sequences. Fusion proteins are useful because they can be constructed to contain two or more desired functional elements from two or more different proteins. Fusion proteins can be produced recombinantly by constructing a nucleic acid sequence which encodes the polypeptide or a fragment thereof in frame with a nucleic acid sequence encoding a different protein or peptide and then expressing the fusion protein.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases, or genomic sequences with which it is naturally associated. The term embraces a nucleic acid or polynucleotide that has been removed from its naturally occurring environment. The term "isolated" or "substantially pure" also can be used in reference to recombinant or cloned DNA isolates, chemically synthesized polynucleotide analogs, or polynucleotide analogs that are biologically synthesized by heterologous systems.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using Fasta, a program in GCG Version 6.1. Fasta provides alignments and percent sequence identity of the regions of the best overlap between the query and search sequences (Pearson, 1990). For instance, percent sequence identity between nucleic acid sequences can be determined using Fasta with its default parameters (a word size of 6 and the NOPAMfactor for the scoring matrix) as provided in GCG Version 6.1.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases, as measured by any well-known algorithm of sequence identity, such as Fasta, as discussed above.

Alternatively, substantial homology or similarity exists when a nucleic acid or fragment thereof hybridizes to another nucleic acid, to a strand of another nucleic acid, or to the complementary strand thereof, under selective hybridization conditions. Typically, selective hybridization will occur when there is at least about 55% sequence identity— preferably at least about 65%, more preferably at least about 75%, and most preferably at least about 90%—over a stretch of at least about 14 nucleotides. See, e.g., Kanehisa (1984) *Nucl. Acids Res.* 12:203–213.

Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. "Stringent hybridization conditions" and "stringent wash conditions" in the context of nucleic acid hybridization experiments depend upon a number of different physical parameters. The most important parameters include temperature of hybridization, base composition of the nucleic acids, salt concentration and length of the nucleic acid. One having ordinary skill in the art knows how to vary these parameters to achieve a particular stringency of hybridization. In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., p. 9.51.

The $T_m$ for a particular DNA-DNA hybrid can be estimated by the formula:

$$T_m = 81.5° C. + 16.6 \ (\log_{10}[\text{Na}^+]) + 0.41 \ (\text{fraction G+C}) - 0.63 \ (\% \ \text{formamide}) - (600/l)$$

where l is the length of the hybrid in base pairs.

The $T_m$ for a particular RNA-RNA hybrid can be estimated by the formula:

$$T_m = 79.8° C. + 18.5 \ (\log_{10}[\text{Na}^+]) + 0.58 \ (\text{fraction G+C}) + 11.8 \ (\text{fraction G+C})^2 - 0.35 \ (\% \ \text{formamide}) - (820/l).$$

The $T_m$ for a particular RNA-DNA hybrid can be estimated by the formula:

$$T_m = 79.8° C. + 18.5 (\log_{10}[\text{Na}^+]) + 0.58 \ (\text{fraction G+C}) + 11.8 \ (\text{fraction G+C})^2 - 0.50 \ (\% \ \text{formamide}) - (820/l).$$

In general, the $T_m$ decreases by 1–1.5° C. for each 1% of mismatch between two nucleic acid sequences. Thus, one having ordinary skill in the art can alter hybridization and/or washing conditions to obtain sequences that have higher or lower degrees of sequence identity to the target nucleic acid. For instance, to obtain hybridizing nucleic acids that contain up to 10% mismatch from the target nucleic acid sequence, 10–15° C. would be subtracted from the calculated $T_m$ of a perfectly matched hybrid, and then the hybridization and washing temperatures adjusted accordingly. Probe sequences may also hybridize specifically to duplex DNA under certain conditions to form triplex or other higher order DNA complexes. The preparation of such probes and suitable hybridization conditions are well known in the art.

An example of stringent hybridization conditions for hybridization of complementary nucleic acid sequences having more than 100 complementary residues on a filter in a Southern or Northern blot or for screening a library is 50% formamide/6×SSC at 42° C. for at least ten hours. Another example of stringent hybridization conditions is 6×SSC at 68° C. for at least ten hours. An example of low stringency hybridization conditions for hybridization of complementary nucleic acid sequences having more than 100 complementary residues on a filter in a Southern or northern blot or for screening a library is 6×SSC at 42° C. for at least ten hours. Hybridization conditions to identify nucleic acid sequences that are similar but not identical can be identified by experimentally changing the hybridization temperature from 68° C. to 42° C. while keeping the salt concentration constant (6×SSC), or keeping the hybridization temperature and salt concentration constant (e.g. 42° C. and 6×SSC) and varying the formamide concentration from 50% to 0%. Hybridization buffers may also include blocking agents to lower background. These agents are well-known in the art. See Sambrook et al., pp. 8.46 and 9.46–9.58.

Wash conditions also can be altered to change stringency conditions. An example of stringent wash conditions is a 0.2×SSC wash at 65 ° C. for 15 minutes (see Sambrook et al., for SSC buffer). Often the high stringency wash is preceded by a low stringency wash to remove excess probe. An exemplary medium stringency wash for duplex DNA of more than 100 base pairs is 1×SSC at 45° C. for 15 minutes. An exemplary low stringency wash for such a duplex is 4×SSC at 40° C. for 15 minutes. In general, signal-to-noise ratio of 2× or higher than that observed for an unrelated probe in the particular hybridization assay indicates detection of a specific hybridization.

As defined herein, nucleic acids that do not hybridize to each other under stringent conditions are still substantially homologous to one another if they encode polypeptides that are substantially identical to each other. This occurs, for example, when a nucleic acid is created synthetically or recombinantly using a high codon degeneracy as permitted by the redundancy of the genetic code.

The polynucleotides of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

"Conservatively modified variations" of a particular nucleic acid sequence refers to nucleic acids that encode identical or essentially identical amino acid sequences or DNA sequences where no amino acid sequence is encoded. Due to the degeneracy of the genetic code, a large number of functionally identical nucleic acids encode any given polypeptide sequence. When a nucleic acid sequence is changed at one or more positions with no corresponding change in the amino acid sequence which it encodes, that mutation is called a "silent mutation." Thus, one species of a conservatively modified variation according to this invention is a silent mutation. Accordingly, every nucleic acid sequence herein which encodes a polypeptide also describes every possible silent mutation or variation.

Furthermore, one of skill in the art will recognize that individual substitutions, deletions, additions and the like, which alter, add or delete a single amino acid or a small percentage of amino acids (less than 5%, more typically less than 1%) in an encoded sequence are "conservatively modified variations" where the alterations result in the substitution of one amino acid with a chemically similar amino acid. Conservative substitution tables providing functionally similar amino acids are well known in the art.

The term "antibody" refers to a polypeptide encoded by an immunoglobulin gene, genes, or fragments thereof. The immunoglobulin genes include the kappa, lambda, alpha, gamma, delta, epsilon and mu constant regions, as well as a myriad of immunoglobulin variable regions. Light chains are classified as either kappa or lambda. Heavy chains are classified as gamma, mu, alpha, delta, or epsilon, which in turn define the immunoglobulin classes IgG, IgM, IgA, IgD and IgE, respectively.

Antibodies exist for example, as intact immunoglobulins or as a number of well-characterized fragments produced by digestion with various peptidases. For example, trypsin digests an antibody below the disulfide linkages in the hinge region to produce F(ab)'$_2$, a dimer of Fab which itself is a light chain joined to a $V_H$—$C_H1$ by a disulfide bond. The F(ab)'$_2$ may be reduced under mild conditions to break the disulfide linkage in the hinge region thereby converting the F(ab)'$_2$ dimer to a Fab' monomer. The Fab' monomer is essentially an Fab with part of the hinge region. See Paul, ed. (1993) *Fundamental Immunology,* Third Edition (New York: Raven Press), for a detailed description of epitopes, antibodies and antibody fragments. One of skill in the art recognizes that such Fab' fragments may be synthesized de novo either chemically or using recombinant DNA technology. Thus, as used herein, the term antibody includes antibody fragments produced by the modification of whole antibodies or those synthesized de novo. The term antibody also includes single-chain antibodies, which generally consist of the variable domain of a heavy chain linked to the variable domain of a light chain. The production of single-chain antibodies is well known in the art (see, e.g., U.S. Pat. No. 5,359,046). The antibodies of the present invention are optionally derived from libraries of recombinant antibodies in phage or similar vectors (see, e.g., Huse et al. (1989) *Science* 246:1275–81; Ward et al. (1989) *Nature* 341:544–46; Vaughan et al. (1996) *Nature Biotech.* 14:309–14).

As used herein, "epitope" refers to an antigenic determinant of a polypeptide, i.e., a region of a polypeptide that provokes an immunological response in a host. This region need not comprise consecutive amino acids. The term epitope is also known in the art as "antigenic determinant." An epitope may comprise as few as three amino acids in a spatial conformation which is unique to the immune system of the host. Generally, an epitope consists of at least five such amino acids, and more usually consists of at least 8–10 such amino acids. Methods for determining the spatial conformation of such amino acids are known in the art.

Methods for Construction Mutant Yeast Strains

There are a number of methods well known in the art by which a person can disrupt a particular gene in yeast. One of skill in the art can disrupt an entire gene and create a null allele, in which no portion of the gene is expressed. One can also produce and express an allele comprising a portion of the gene which is not sufficient for gene function. This can be done by inserting a nonsense codon into the sequence of the gene such that translation of the mutant mRNA transcript ends prematurely. One can also produce and express alleles containing point mutations, individually or in combination, that reduce or abolish gene function.

There are a number of different strategies for creating conditional alleles of genes. Broadly, an allele can be conditional for function or expression. An example of an allele that is conditional for function is a temperature sensitive mutation where the gene product is functional at one temperature but non-functional at another, e.g., due to misfolding or mislocalization. One of ordinary skill in the art can produce mutant alleles which may have only one or a few altered nucleotides but which encode inactive or temperature-sensitive proteins. Temperature-sensitive mutant yeast strains express a functional protein at permissive temperatures but do not express a functional protein at non-permissive temperatures.

An example of an allele that is conditional for expression is a chimeric gene where a regulated promoter controls the expression of the gene. Under one condition the gene is expressed and under another it is not. One may replace or alter the endogenous promoter of the gene with a heterologous or altered promoter that can be activated only under certain conditions. These conditional mutants only express the gene under defined experimental conditions. All of these methods are well known in the art. For example, see Stark (1998) *Methods in Microbiology* 26:83–100; Garfinkel et al. (1998) *Methods in Microbiology* 26:101–118; and Lawrence & Rothstein (1991) *Methods in Enzymology* 194:281–301.

One having ordinary skill in the art also may decrease expression of a gene without disrupting or mutating the gene. For instance, one can decrease the expression of an essential gene by transforming yeast with an antisense molecule under the control of a regulated or constitutive promoter (see Nasr et al. (1995) *Molecular & General Genetics* 249:51–57). One can introduce an antisense construct operably linked to an inducible promoter into *S. cerevisiae* to study the function of a conditional allele (see Nasr et al. supra). One problem that may be encountered, however, is that many antisense molecules do not work well in yeast, for reasons that are, as yet, unclear (see Atkins et al. (1994) *Biological Chemistry* 375:721–29; and Olsson et al. (1997) *Applied and Environmental Microbiology* 63:2366–71).

One may also decrease gene expression by inserting a sequence by homologous recombination into or next to the gene of interest wherein the sequence targets the mRNA or the protein for degradation. For instance, one can introduce a construct that encodes ubiquitin such that a ubiquitin fusion protein is produced. This protein will be likely to have a shorter half-life than the wildtype protein. See, e.g., Johnson et al. (1992) *EMBO J.* 11:497–505.

In a preferred mode, a gene of interest is completely disrupted in order to ensure that there is no residual function of the gene. One can disrupt a gene by "classical" or PCR-based methods. The "classical" method of gene knockout is described by Rothstein, 1991. However, it is preferable to use a PCR-based deletion method because it is faster and less labor intensive.

The strategy adopted by the consortium is to utilize a one-step, polymerase chain reaction (PCR) based gene deletion method (Rothstein, 1991). Each DNA construct that is used to create the mutations are produced by two rounds of PCR (FIG. 1). All oligonucleotide synthesis and the two rounds of construct PCR (see below) are performed at a central location (Ron Davis' laboratory, Stanford University). The purified PCR products and the primers required for the analysis of the mutants are then assigned and dispersed to the various consortium members.

Gene specific UPTAG and DOWNTAG primer pairs are designed for PCR amplification of the plasmid pFA6a-KanMX4 (Wach et al. (1994) *Yeast* 10:1793–1808). The 3' ends of the UPTAG and DOWNTAG synthetic oligonucleotides have been designed to include 18 basepairs (bp) and 19 bp, respectively, of nucleotide homology flanking the KanMX gene of the plasmid pFA6a-KanMX4 template (see FIG. 1). All of the gene specific UPTAG and DOWNTAG primer pairs contain these complementary sequences, such that the same plasmid pFA6a-KanMX4 template can be used for all of the first round PCR reactions. At their 5' ends, the UPTAG and DOWNTAG primers each have gene specific sequence homologies. The UPTAG primer contains a nucleotide sequence which includes the start codon of the gene to be knocked out and the sequence immediately upstream of the start codon. The DOWNTAG primer contains a nucleotide sequence which includes the stop codon of the gene and the sequence immediately downstream of the stop codon. For each set of primers, the sequences of the gene are derived from one of the 6000 ORFs identified in the SGD.

The UPTAG and DOWNTAG primers are then used to amplify the pFA6a-KanMX4 by PCR using conditions for PCR as described below. Hybridization conditions for specific UPTAG and DOWNTAG primers can be experimentally determined, or estimated by a number of formulas. One such formula is $T_m=81.5+16.6(\log_{10}[Na^+])+0.41$ (fraction G+C)−(600/N). See Sambrook et al. pages 11.46–11.47. The products of the first round PCR reactions are DNA molecules containing the KanMX marker (conferring resistance to the drug G-418 in *S. cerevisiae*) flanked on both ends by 18 bp of gene specific sequences (FIG. 1).

The gene specific flanking sequences are extended during the second round PCR reactions (FIG. 1). The sequences of the two gene specific PCR primers (Upstream45 and Downstream45) are derived from the 45 bp immediately upstream (including the start codon) and the 45 bp immediately downstream (including the stop codon) of each gene. Thus, following the second round of PCR the product contains the KanMX marker flanked by 45 bp of gene specific sequences corresponding to the sequences flanking the gene's ORF. The PCR products are purified by an isopropanol precipitation, and shipped with the analytical primers (see below) to the consortium members on dry ice. The precipitated PCR products are resuspended in TE buffer (10 mM Tris-HCl [pH 7.6], 1 mM EDTA).

The various mutations are constructed in two related *Saccharomyces cerevisiae* strains, BY4741 (MATa his3Δ1 leu2Δ0 met15Δ0 ura3Δ0) and BY4743 (MATa/MATα his3Δ1/his3Δ1 leu2Δ0/leu2Δ0 LYS2/lys2Δ0 met15Δ0/MET15 ura3Δ0/ura3Δ0) (Brachmann et al. (1998) *Yeast* 14:115–32). Both of these strains are transformed with the PCR products by the lithium acetate method as described by Ito et al. (1983) *J Bacteriol.* 153:163–68; and Schiestl & Gietz, 1989. The flanking, gene-specific yeast sequences target the integration event by homologous recombination to the desired locus (FIG. 1). Transformants are selected on rich medium (YPD) which contains G-418 (Geneticin, Life Technologies, Inc.) as described by Guthrie & Fink, 1991. Ideally, independent mutations are isolated in the haploid (BY4741) and the diploid (BY4743) strains. The heterozygous mutant diploid strain is then sporulated, and subjected to tetrad analysis (Sherman (1991) *Methods Enzymol.* 194:3–21; Sherman & Wakem (1991) *Methods Enzymol.* 194:38–57). This allows for the isolation of the mutation in a MATα haploid strain. The two independently isolated MATa and MATα haploid strains are then mated to create a homozygous mutant diploid strain. Additionally, the tetrad analysis of the heterozygous mutant diploid strain allows for the identification of genes that are essential for germination and/or vegetative growth.

Figure 2:
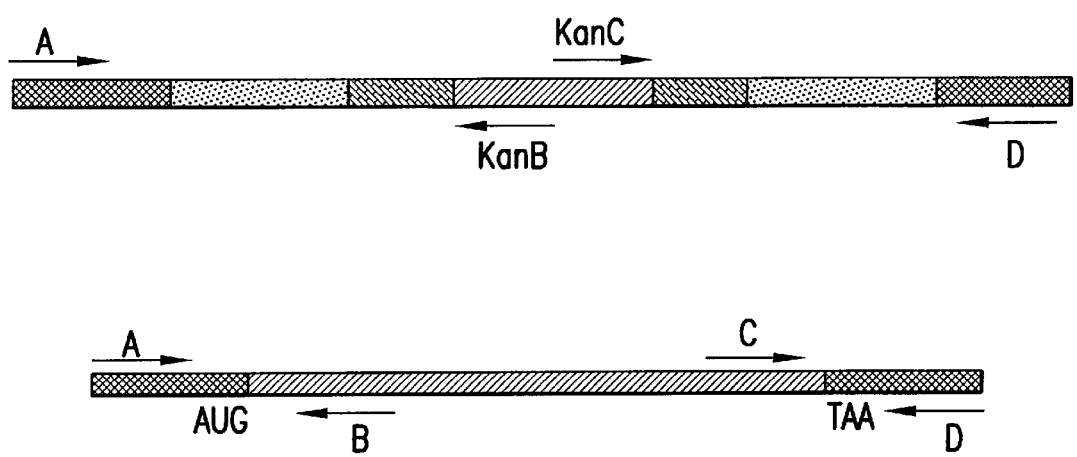
FIG. 2. A PCR based strategy for the analysis of the knock-out mutation. Four primers (A, B, C, and D) are gene specific (i.e. YFR003C, YGR277C, YGR278W, YKR071C, YKR079C, or YKR083C), and two primers are marker specific (KanB and KanC). The wildtype allele produces PCR products of predicted sizes with primer pairs AB, CD, and AD, but not with pairs AKanB and KanCD. The mutant allele produces PCR products of predicted sizes with primer pairs AKanB, KanCD, and AD, but not with pairs AB and CD.

The molecular structure of each mutation is confirmed by a PCR strategy, utilizing four gene specific primers and two marker specific primers (FIG. 2). Two primers (A and D) flank the gene, and two primers (B and C) are within the coding region. Both recombination junctions are examined using gene specific (A/B and C/D, 5' and 3' junctions respectively) and marker specific (A/KanB and KanC/D, 5' and 3' respectively) primer pairs. A correct mutant locus fails to produce PCR products with the gene specific primers, and produces PCR products of predicted sizes with the marker specific primers. Additionally, the overall size of the locus is confirmed utilizing the flanking (A/D) primers. The resulting locus is a precise deletion of the ORF (except the start and stop codons), and the insertion of the construct PCR product containing the KanMX marker.

Methods to Identify Essential Yeast Genes

One of skill in the art will recognize that a number of methods can be used to test whether a gene is essential for vegetative growth or germination. In general, the preferred strategy depends upon the assumptions made regarding the function of the gene. For example, if one creates a conditional allele of the gene, then one can engineer a mutant strain wherein the wildtype allele has been replaced by a conditional allele. See, e.g., Stark (1998) *Methods in Microbiology* 26:83–100. The strain is constructed and propagated under the permissive condition, and then the strain is switched to the non-permissive (or restrictive) condition and proliferation is monitored to test whether the gene is essential for growth. This can be done in a haploid cell, or in a diploid cell as either a homozygous or heterozygous mutant.

A preferred method of testing whether a gene is essential for vegetative growth or germination is to knockout the gene completely and then analyze the knockout yeast strain by tetrad analysis. This method is preferred because one does not need to be able to engineer a conditional allele. Furthermore, as the knockout is a null allele, one is assured that it is the null phenotype that is assessed, rather than a phenotype resulting from a potentially hypomorphic conditional allele. In addition, a complete knockout of the gene can be constructed in a diploid strain where the potentially essential function of the gene is complemented by the second copy of the gene.

Once the knockout has been constructed as a heterozygous mutant, the lethality of the mutation is assessed in the haploid spores. Tetrad analysis of the haploid spores allows for the genetic characterization of a mutation because it can be determined that lethality is due to a single, nuclear mutation linked to the knockout marker (G-418 resistance).

As discussed above, an essential gene may affect either germination or vegetative growth of a yeast cell. Germination refers to a spore's reentry into the cell cycle and proliferative growth, while vegetative growth refers to the growth of the spores after germination. Tetrad analysis can be used to determine the effects of a knockout gene on either germination or vegetative growth. Tetrad dissection is the most direct way to assess germination because one can immediately and visually determine (microscopically) whether a yeast spore has germinated, or, if it has germinated, whether it has proliferated. If a gene is essential either for vegetative growth or germination, those spores containing the knockout allele will not proliferate, while those containing the wildtype allele will grow normally.

One of ordinary skill in the art will recognize that whether a gene is characterized as essential is dependent in part upon the conditions under which tetrad analysis is performed. The choice of growth medium and growing conditions may influence the effect of the knockout on vegetative growth and germination. For instance, asci dissection and growth performed on minimal medium may produce a greater number of essential genes compared to asci dissection and growth performed on rich medium. Temperature will also affect the determination of essential genes. One having ordinary skill in the art will be able to determine what growth parameters are important for their particular use. Preferably, tetrad analysis is performed on a rich growth medium at 30° C. in order to minimize the number of genes that are essential only in medium that contains limited amounts of nutrients and under normal growth conditions.

Approximately 20% of the S. cerevisiae genome is duplicated. Therefore, there are a number of essential cellular functions that are encoded by two or more copies of the gene. For example, the genes RAS1 and RAS2 are highly homologous and encode GTP-binding proteins involved in the regulation of the essential cAMP pathway. Due to the overlapping functions of these two genes, a RAS1 mutation is not lethal in a wildtype background but is lethal in a RAS2 background (Toda et al. (1987) Cell 50:277–87). With the complete genomic sequence of S. cerevisiae known, it has been possible to compile all of the duplicated genes. Thus, it may be necessary to construct multiple mutations in order to assess which of the duplicated genes encode essential functions. This can be easily achieved by crossing the MATa haploid of one mutant to the MATα haploid of another mutant to create a double heterozygous diploid. Tetrad analysis can then be performed to determine if the double mutation is lethal. Further multiple mutations (i.e., triple, quadruple, etc.) can be created and assessed in an analogous manner.

If a gene is determined to be essential for the vegetative growth and/or germination of S. cerevisiae, further analysis can be performed to characterize the lethal phenotype. The dead spores can be examined microscopically to determine if any cell division had occurred. If the spore fails to divide even once, it would suggest that the gene product is required for germination. This can be addressed further by constructing a conditional allele of the gene, which allows for a separate assessment of the gene's involvement in vegetative growth and germination. If a spore divides a number of times before ceasing growth, it would indicate that the spore is able to germinate and that the gene is required for vegetative growth but not for germination. The cellular morphology can be examined further to determine if the cells are arrested at a specific point of the cell cycle (Lew et al. (1997) "Cell Cycle Control in Saccharomyces cerevisiae," in The Molecular and Cellular Biology of the Yeast Saccharomyces, J. R. Pringle, J. R. Broach and E. W. Jones, eds. (Cold Spring Harbor, N.Y.: Cold Spring Harbor Laboratory Press), pp. 607–696). A specific cell cycle arrest may provide some insights into the function of the gene product.

Another method for characterizing the essential gene is to determine whether the heterozygous diploid has a slow growth phenotype compared to the wildtype strain. In general, the heterozygous diploid will have only half of the amount of the essential gene product compared to the wildtype strain. Therefore, if the heterozygous diploid grows more slowly than the wildtype strain, it is likely that the quantity of the essential gene product is limiting for cell proliferation in the heterozygous diploid. If this is the case, it may indicate that it is not necessary to inhibit completely the function of the gene product to give rise to an impaired phenotype. This information is useful because it provides information about whether an antifungal agent would have to inhibit the gene completely to be effective, or whether only a decrease in the gene's activity would be required.

In order to characterize whether the heterozygous diploid has a slow growth phenotype, a co-culture experiment with the wildtype strain may be performed. During the course of co-culturing the two strains, samples are removed and the relative amounts of the two strains in the culture are determined. This can be achieved simply by plating a calculated dilution of the culture on rich media, counting the total number of cells, and then replica-plating the cells on selective media plates. In the case where the essential gene is disrupted using the KanMX marker, one can use YPD-G-418 plates to determine the fraction of these cells that are heterozygous diploids. If, after co-culturing, the heterozygous diploids are present as a smaller fraction of cells than the fraction they represented before co-culturing, then the heterozygous diploids exhibit a slow growth phenotype. Time courses of co-cultured strains may be done in order to provide more precise estimates of relative growth proficiencies.

Some fungal species are pathogenic only in the pseudohyphal or hyphal phase. For such species, genes can be assessed for their requirement for pseudohyphal or hyphal growth. For instance, S. cerevisiae genes required for pseudohyphal growth can be identified by growing the mutants on the appropriate medium which promotes pseudohyphal growth (i.e., a low nitrogen medium).

Methods to Identify Potential Homologs in Other Organs

Once a gene has been mutated and shown to be essential for vegetative growth or germination, one can determine whether the essential gene from yeast has homologs in other organisms, such as humans, non-human mammals, other vertebrates such as fish, insects, plants, or other fungi.

One method of determining whether an essential *S. cerevisiae* gene has homologs is by the use of low stringency hybridization and washing. In general, genomic DNA or cDNA libraries can be screened using probes derived from the essential *S. cerevisiae* gene using methods known in the art. See above and pp. 8.46–8.49 and 9.46–9.58 of Sambrook et al., 1989. Preferably, genomic DNA libraries are screened because cDNA libraries generally will not contain all the mRNA species an organism can make. Genomic DNA libraries from a variety of different organisms, such as plants, fungi, insects, and various mammalian species are commercially available and can be screened. This method is useful for determining whether there are homologs in organisms whose DNA sequences have not been characterized extensively.

A second method of determining whether an essential *S. cerevisiae* gene has homologs is through the use of degenerate PCR. In this method, degenerate oligonucleotides that encode short amino acid sequences of the essential *S. cerevisiae* gene are made. Methods of preparing degenerate oligonucleotides and using them in PCR to isolate uncloned genes are well known in the art (see Sambrook et al., 1989, pp. 14.7–14.8).

The most preferred method is to compare the sequence of the *S. cerevisiae* gene to sequences from other organism. Either the nucleotide sequence of the essential gene or its encoded amino acid sequence is compared to the sequences from other organisms. Preferably, the encoded amino acid sequence of the essential gene is compared to amino acid sequences from other organisms. The sequence of the essential gene can be compared by a number of different algorithms well known in the art (see definitions section). In general, computer programs designed for sequence analysis are used for the purpose of comparing the sequence of interest to a large database of other sequences. Any computer program designed for the purpose of sequence comparison can be used in this method. Some computer programs, such as Fasta, produce results that are typically presented as "% sequence identity." Other computer programs, such as blastp, produce results presented as "p-values." Preferably, the essential gene sequence will be compared to other sequences using the blastp algorithm.

Nucleotide and amino acid sequences of essential genes may be compared to vertebrate sequences, including human and non-human mammalian sequences, as well as plant and insect sequences using any one of the large number of programs known in the art for comparing nucleotide and amino acid sequences to sequences in a database. Examples of such programs are Fasta and blastp, discussed above. Examples of databases which can be searched include GenBank-EMBL, SwissProt, DDBJ, GeneSeq, and EST databases, as well as databases containing combinations of these databases.

The invention envisions that, regardless of how the homolog is first identified, the blastp algorithm or functional equivalent or improvement thereof, will be used to determine the "p-value" for the amino acid sequence encoded by an essential yeast gene and the amino acid sequence of its homolog. The invention envisions that the homolog will fall into one of three groups based upon its level of sequence identity to genes from other organisms. One group are those proteins wherein the sequence encoded by essential yeast genes exhibits no substantial homology to a protein sequence from the organism of interest. For instance, if a human antifungal agent is desired, the essential fungal gene or encoded protein target exhibits no substantial homology to any known gene or EST, or to any encoded protein from a gene from human. If a plant antifungal agent is desired, the essential fungal gene or encoded protein target exhibits no significant homology to any known gene, EST, or encoded protein from a plant. Conversely, if an herbicide or insecticide is desired, the essential fungal gene target preferably will exhibit strong (Type 1) or weak (Type 2) homology to a plant or insect protein. Similarly, if an anti-proliferative drug is desired, the essential fungal gene target preferably will exhibit strong (Type 1) homology, or less desirably weak (Type 2) homology, to a human or mammalian protein.

Essential yeast genes may encode potential antifungal targets even when there is homology with an amino acid sequence of a protein from a desired host. Preferably, the yeast gene exhibits a limited degree of homology with the amino acid sequence of a protein from a desired host. Members of this group would be considered a weak homolog (Type 2). For instance, the polypeptide of the essential yeast gene could show a low level of sequence identity or homology over the entire length of the host protein. Alternatively, the encoded yeast protein could exhibit substantial homology or sequence identity over small region(s) with the protein from a desired host. A third group of potential antifungal targets encompasses essential yeast genes which exhibit substantial homology (Type 1 homologs) with polypeptides from a desired host. This group is less preferred as antifungal targets than genes which encode proteins with no homology or with limited homology. However, even minor differences between the essential gene or its encoded protein and the homologous gene or its encoded protein in the desired host can be exploited using the essential yeast gene target to produce antifungal agents by the methods described below.

As a further characterization of the yeast essential gene (see above), any potential homologs from other organisms can be assessed for their ability to functionally complement the yeast mutant. This can be achieved by first cloning the homolog into a *S. cerevisiae* expression vector by standard methods. This plasmid can then be transformed into the heterozygous mutant diploid strain. Upon sporulation and tetrad dissection the ability of the homolog to complement the yeast function is determined by whether or not the haploid spores harboring the knockout mutation are able to grow. The ability of the homolog to complement the yeast mutant would indicate shared function(s) and suggest that the homolog may also be essential in the original organism.

Nucleic Acids, Vectors and Production of Recombinant Polypeptides

The present invention provides nucleic acids and recombinant DNA vectors which comprise *S. cerevisiae* essential gene DNA sequences. Specifically, vectors comprising all or portions of the DNA sequence of YFR003C, YGR277C, YGR278W, YKR071C, YKR079C, and YKR083C are provided. The vectors of this invention also include those comprising DNA sequences which hybridize under stringent conditions to the YFR003C, YGR277C, YGR278W, YKR071C, YKR079C, and YKR083C gene sequences, and conservatively modified variations thereof.

The nucleic acids of this invention include single-stranded and double-stranded DNA, RNA, oligonucleotides, antisense molecules, or hybrids thereof and may be isolated from biological sources or synthesized chemically or by recombinant DNA methodology. The nucleic acids, recombinant DNA molecules and vectors of this invention may be present in transformed or transfected cells, cell lysates, or in partially purified or substantially pure forms.

DNA sequences may be expressed by operatively linking them to an expression control sequence in an appropriate expression vector and employing that expression vector to transform an appropriate unicellular host. Expression control sequences are sequences which control the transcription, post-transcriptional events and translation of DNA sequences. Such operative linking of a DNA sequence of this invention to an expression control sequence, of course, includes, if not already part of the DNA sequence, the provision of a translation initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences.

Useful expression vectors for bacterial hosts include bacterial plasmids, such as those from *E. coli,* including pBluescript, pGEX-2T, pUC vectors, col E1, pCR1, pBR322, pMB9 and their derivatives, wider host range plasmids, such as RP4, phage DNAs, e.g., the numerous derivatives of phage lambda, e.g., NM989, λGT10 and λGT11, and other phages, e.g., M13 and filamentous single stranded phage DNA. In yeast, vectors include Yeast Integrating plasmids (e.g., YIp5) and Yeast Replicating plasmids (the YRp and YEp series plasmids), Yeast centromere plasmids (the YCp series plasmids), pGPD-2, 2μ plasmids and derivatives thereof, and improved shuttle vectors such as those described in Gietz& Sugino (1988) *Gene* 74:527–34 (YIplac, YEplac and YCplac). Expression in mammalian cells can be achieved using a variety of plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses). Useful vectors for insect cells include baculoviral vectors and pVL 941.

In addition, any of a wide variety of expression control sequences—sequences that control the expression of a DNA sequence when operatively linked to it—may be used in these vectors to express the DNA sequences of this invention. Such useful expression control sequences include the expression control sequences associated with structural genes of the foregoing expression vectors. Expression control sequences that control transcription include, e.g., promoters, enhancers and transcription termination sites. Expression control sequences that control post-transcriptional events include splice donor and acceptor sites and sequences that modify the half-life of the transcribed RNA, e.g., sequences that direct poly(A) addition or binding sites for RNA-binding proteins. Expression control sequences that control translation include ribosome binding sites, sequences which direct expression of the polypeptide to particular cellular compartments, and sequences in the 5' and 3' untranslated regions that modify the rate or efficiency of translation.

Examples of useful expression control sequences include, for example, the early and late promoters of SV40 or adenovirus, the lac system, the trp system, the TAC or TRC system, the T3 and T7 promoters, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast α-mating system, the GAL1 or GAL10 promoters, and other constitutive and inducible promoter sequences known to control the expression of genes of prokaryotic or eukaryotic cells or their viruses, and various combinations thereof. See, e.g., *The Molecular Biology of the Yeast Saccharomyces* (eds. Strathern, Jones and Broach) Cold Spring Harbor Lab., Cold Spring Harbor, N.Y. for details on yeast molecular biology in general and on yeast expression systems (pp. 181–209).

DNA vector design for transfection into mammalian cells should include appropriate sequences to promote expression of the gene of interest, including: appropriate transcription initiation, termination and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. A great number of expression control sequences—constitutive, inducible and/or tissue-specific—are known in the art and may be utilized. For eukaryotic cells, expression control sequences typically include a promoter, an enhancer derived from immunoglobulin genes, SV40, cytomegalovirus, etc., and a polyadenylation sequence which may include splice donor and acceptor sites. Substantial progress in the development of mammalian cell expression systems has been made in the last decade and many aspects of the system are well characterized.

Preferred DNA vectors also include a marker gene and means for amplifying the copy number of the gene of interest. DNA vectors may also comprise stabilizing sequences (e.g., ori- or ARS-like sequences and telomere-like sequences), or may alternatively be designed to favor directed or non-directed integration into the host cell genome. In a preferred embodiment, DNA sequences of this invention are inserted in frame into an expression vector that allows high level expression of an RNA which encodes a fusion protein comprising encoded DNA sequence of interest.

Of course, not all vectors and expression control sequences will function equally well to express the DNA sequences of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must be replicated in it. The vector's copy number, the ability to control that copy number, the ability to control integration, if any, and the expression of any other proteins encoded by the vector, such as antibiotic or other selection markers, should also be considered.

In selecting an expression control sequence, a variety of factors should also be considered. These include, for example, the relative strength of the sequence, its controllability, and its compatibility with the DNA sequence of this invention, particularly with regard to potential secondary structures. Unicellular hosts should be selected by consideration of their compatibility with the chosen vector, the toxicity of the product coded for by the DNA sequences of this invention, their secretion characteristics, their ability to fold the polypeptide correctly, their fermentation or culture requirements, and the ease of purification from them of the products coded for by the DNA sequences of this invention.

Within these parameters, one of skill in the art may select various vector/expression control sequence/host combinations that will express the DNA sequences of this invention in fermentation or in other large scale cultures.

Given the strategies described herein, one of skill in the art can construct a variety of vectors and nucleic acid molecules comprising functionally equivalent nucleic acids. DNA cloning and sequencing methods are well known to those of skill in the art and are described in an assortment of laboratory manuals, including Sambrook et al., 1989; and Ausubel et al., 1994 Supplement. Product information from manufacturers of biological, chemical and immunological reagents also provide useful information.

The recombinant DNA molecules and more particularly, the expression vectors of this invention may be used to express the essential genes from S. cerevisiae as recombinant polypeptides in a heterologous host cell. The polypeptides of this invention may be full-length or less than full-length polypeptide fragments recombinantly expressed from the DNA sequences according to this invention. Such polypeptides include variants and muteins having biological activity. The polypeptides of this invention may be soluble, or may be engineered to be membrane- or substrate-bound using techniques well known in the art.

Particular details of the transfection, expression and purification of recombinant proteins are well documented and are understood by those of skill in the art. Further details on the various technical aspects of each of the steps used in recombinant production of foreign genes in mammalian cell expression systems can be found in a number of texts and laboratory manuals in the art. See, e.g., Ausubel et al., 1989.

Transformation and other methods of introducing nucleic acids into a host cell (e.g., transfection, electroporation, liposome delivery, membrane fusion techniques, high velocity DNA-coated pellets, viral infection and protoplast fusion) can be accomplished by a variety of methods which are well known in the art (see, for instance, Ausubel, supra, and Sambrook, supra). Bacterial, yeast, plant or mammalian cells are transformed or transfected with an expression vector, such as a plasmid, a cosmid, or the like, wherein the expression vector comprises the DNA of interest. Alternatively, the cells may be infected by a viral expression vector comprising the DNA or RNA of interest. Depending upon the host cell, vector, and method of transformation used, transient or stable expression of the polypeptide will be constitutive or inducible. One having ordinary skill in the art will be able to decide whether to express a polypeptide transiently or stably, and whether to express the protein constitutively or inducibly.

A wide variety of unicellular host cells are useful in expressing the DNA sequences of this invention. These hosts may include well known eukaryotic and prokaryotic hosts, such as strains of E. coli, Pseudomonas, Bacillus, Streptomyces, fungi, yeast, insect cells such as Spodoptera frugiperda (SF9), animal cells such as CHO, BHK, MDCK and various murine cells, e.g., 3T3 and WEHI cells, African green monkey cells such as COS 1, COS 7, BSC 1, BSC 40, and BMT 10, and human cells such as VERO, WI38, and HeLa cells, as well as plant cells in tissue culture.

Expression of recombinant DNA molecules according to this invention may involve post-translational modification of a resultant polypeptide by the host cell. For example, in mammalian cells expression might include, among other things, glycosylation, lipidation or phosphorylation of a polypeptide, or cleavage of a signal sequence to produce a "mature" protein. Accordingly, the polypeptide expression products of this invention encompass full-length polypeptides and modifications or derivatives thereof, such as glycosylated versions of such polypeptides, mature proteins and polypeptides retaining a signal peptide. The present invention also provides for biologically active fragments of the polypeptides. Sequence analysis or genetic manipulation may identify those domains responsible for the essential function of the protein in yeast. Thus, the invention encompasses the production of biologically active fragments that can be used as antifungal targets. The invention also encompasses fragments of the polypeptides which would be valuable as antigens for the production of antibodies, or as competitors for antibody binding.

The polypeptides of this invention may be fused to other molecules, such as genetic, enzymatic or chemical or immunological markers such as epitope tags. Fusion partners include, inter alia, myc, hemagglutinin (HA), GST, immunoglobulins, β-galactosidase, biotin trpE, protein A, β-lactamase, α amylase, maltose binding protein, alcohol dehydrogenase, polyhistidine (for example, six histidine at the amino and/or carboxyl terminus of the polypeptide), lacZ, green fluorescent protein (GFP), yeast α mating factor, GAL4 transcription activation or DNA binding domain, luciferase, and serum proteins such as ovalbumin, albumin and the constant domain of IgG. See, e.g., Godowski et al. (1988) Science 241(4867):812–6; and Ausubel et al., supra. Fusion proteins may also contain sites for specific enzymatic cleavage, such as a site that is recognized by enzymes such as Factor XIII, trypsin, pepsin, or any other enzyme known in the art. Fusion proteins will typically be made by either recombinant nucleic acid methods, as described above, chemically synthesized using techniques such as those described in Merrifield, et al. (1965) Nature 207(996):522–3, or produced by chemical cross-linking.

Tagged fusion proteins permit easy localization, screening and specific binding via the epitope or enzyme tag. See Ausubel et al., 1991, Chapter 16. Some tags allow the protein of interest to be displayed on the surface of a phagemid, such as M13, which is useful for panning agents that may bind to the desired protein targets. Thus, fusion proteins are useful for screening potential antifungal agents, insecticides, herbicides or anti-proliferation drugs using the protein targets encoded by the essential genes.

One advantage of fusion proteins is that an epitope or enzyme tag can simplify purification. These fusion proteins may be purified, often in a single step, by affinity chromatography. For example, a $His^6$ tagged protein can be purified on a Ni affinity column and a GST fusion protein can be purified on a glutathione affinity column. Similarly, a fusion protein comprising the Fc domain of IgG can be purified on a Protein A or Protein G column and a fusion protein comprising an epitope tag such as myc can be purified using an immunoaffinity column containing an anti-c-myc antibody. It is preferable that the epitope tag be separated from the protein encoded by the essential gene by an enzymatic cleavage site that can be cleaved after purification. A second advantage of fusion proteins is that the epitope tag can be used to bind the fusion protein to a plate or column through an affinity linkage for screening targets.

In addition, fusion proteins comprising the constant domain of IgG or other serum proteins can increase a protein's half-life in circulation for use therapeutically. Fusion proteins comprising a targeting domain can be used to direct the protein to a particular cellular compartment or tissue target in order to increase the efficacy of the functional domain. See, e.g., U.S. Pat. No. 5,668,255, which discloses a fusion protein containing a domain which binds to an animal cell coupled to a translocation domain of a toxin protein. Fusion proteins may also be useful for improving antigenicity of a protein target. Examples of making and using fusion proteins are found in U.S. Pat. Nos. 5,225,538, 5,821,047, and 5,783,398.

Production of Polypeptide Fragments, Derivatives and Muteins and Biological Assays Thereof Fragments, derivatives and muteins of polypeptides encoded by essential genes can be produced recombinantly or chemically, as discussed above. One can produce fragments of a polypeptide encoding an essential gene by truncating the DNA encoding the essential gene and then expressing it recombinantly. Alternatively, one can produce a fragment by chemically synthesizing a portion of the full-length polypeptide. One may also produce a fragment by enzymatically cleaving the polypeptide. Methods of producing polypeptide fragments are well-known in the art (see, e.g., Sambrook et al. and Ausubel et al., supra). Molecules comprising a protein or fragment can also be made by cross-linking the protein or fragment to another chemical structure.

One may produce muteins of a polypeptide encoded by an essential gene by introducing mutations into the DNA sequence of the essential gene and then expressing it recombinantly. These mutations may be targeted, in which particular encoded amino acids are altered, or may be untargeted, in which random encoded amino acids within the polypeptide are altered. Muteins with random amino acid alterations can be screened for a particular biological activity. Methods of producing muteins with targeted or random amino acid alterations are well known in the art, see e.g., Sambrook et al. and Ausubel et al, supra, and U.S. Pat. No. 5,223,408. Production of polypeptide derivatives are well known in the art, see above.

There are a number of methods known in the art to determine whether fragments, muteins and derivatives of polypeptides encoded by essential genes have the same, enhanced or decreased biological activity as the wild type polypeptides. One of the simplest assays involves determining whether the fragment, mutein or derivative can complement the essential gene in a cell which does not contain the essential gene. For instance, one can introduce a DNA encoding a fragment or mutein of a polypeptide encoded by an essential gene into a mutant yeast strain which has the essential gene of interest deleted (see above under "Methods of Producing Mutant Yeast Strains"). If introduction of the DNA encoding the fragment or mutein permits the mutant yeast strain to grow, then the fragment or mutein is biologically active, and complements the deleted gene. One can determine whether the fragment or mutein is more or less active than the wild type polypeptide by co-culturing yeast cells containing the fragment or mutein and yeast cells containing the wild type gene and determining whether the wildtype polypeptide or fragment or mutein is more effective in promoting growth (see above under "Methods to Identify Essential Yeast Genes"). In cases in which there is an essential gene homologous to the essential yeast gene in another organism, this type of complementation analysis of muteins and fragments may be carried out either in yeast cells or in cells from the other organism provided that the essential gene in the cells is knocked out.

Screens may be performed to identify those genes and gene products that interact, either genetically or physically, with the essential gene in question. One may construct a yeast strain which has an essential gene that is non-functional (i.e., the gene is knocked-out or has a mutation that renders the gene product inactive), but which also contains a complementing plasmid bearing the essential gene. An expression library can be screened for clones that, when expressed in this type of yeast strain, allows the loss of the complementing plasmid bearing the essential gene (multi-copy suppression). Alternatively, a mutant screen can be performed in this type of yeast strain to identify second site mutations that allow the loss of the complementing plasmid bearing the essential gene in a strain with the knock-out mutation (synthetic viability).

In another type of screening assay, the essential gene or a fragment thereof can be used as the "bait" in a two-hybrid screen to identify molecules that physically interact with the essential gene. See Chien et al. (1991) *Proc. Natl. Acad. Sci. U.S.A.* 88(21):9578–82.

In addition, one may generate genome expression profiles of yeast strains to characterize the essential gene's function. In order to generate such profiles, a conditional allele of the essential gene in a yeast strain must be produced. The conditional allele may be constructed by any technique known in the art, including making a temperature-sensitive allele of the essential gene or operably linking the essential gene to an inducible promoter for regulated expression. The yeast strain containing the conditional allele is first grown under the permissive condition, allowing expression of the functional product of the essential gene, to permit the growth of the yeast strain for the assay. Then, the yeast strain is shifted to the nonpermissive condition, in which the product of the essential gene is not made or is non-functional. The genome expression profile of the yeast strain under the nonpermissive condition may be measured using, for example, hybridization chips, and the expression profile compared to known standards, e.g., the same yeast strain grown under permissive conditions or a wildtype yeast strain. Structure-function studies can be performed wherein a library of mutant forms of the gene is screened for the ability to complement the knock-out mutant strain.

Fragments, muteins and derivatives may also be microinjected into a mutant yeast strain in which the essential gene of interest is deleted to determine whether the introduction of the fragment, mutein or derivative can complement the genetic defect. Similarly, fragments, muteins and derivatives may be microinjected into other cell types in which the homologous gene has been deleted.

Finally, if a particular biochemical activity of a polypeptide encoded by an essential gene is known, this activity can be measured for fragments, muteins or derivatives of the polypeptide. For instance, if an essential gene encodes a kinase, one could measure the kinase activity of the wild type polypeptide and compare it to the activity of a fragment, mutein or derivative.

Production of Antibodies

The polypeptides encoded by the essential genes of this invention may be used to elicit polyclonal or monoclonal antibodies which bind to the essential gene product or a homolog from another species using a variety of techniques well known to those of skill in the art. Alternatively, peptides corresponding to specific regions of the polypeptide encoded by the essential gene may be synthesized and used to create immunological reagents according to well known methods.

Antibodies directed against the polypeptides of this invention are immunoglobulin molecules or portions thereof that are immunologically reactive with the polypeptide of the present invention. It should be understood that the antibodies of this invention include antibodies immunologically reactive with fusion proteins.

Antibodies directed against a polypeptide encoded by an essential gene may be generated by immunization of a mammalian host. Such antibodies may be polyclonal or monoclonal. Preferably they are monoclonal. Methods to produce polyclonal and monoclonal antibodies are well known to those of skill in the art. For a review of such methods, see Harlow & Lane (1988) *Antibodies, A Laboratory Manual;* Yelton et al. (1981) *Ann. Rev. of Biochem.* 50:657–80; and Ausubel et al., 1989. Determination of immunoreactivity with a polypeptide encoded by an essential gene may be made by any of several methods well known in the art, including by immunoblot assay and ELISA.

Monoclonal antibodies with affinities of $10^{-8}$ $M^{-1}$ or preferably $10^{-9}$ to $10^{-10}$ $M^{-1}$ or stronger are typically made by standard procedures as described, e.g., in Harlow & Lane, 1988. Briefly, appropriate animals are selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989, *Science* 246:1275–81. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. No. 3,817,837; 3,850,752; 3,939,350; 3,996,345; 4,277,437; 4,275,149 and 4,366,241. Also, recombinant immunoglobulins may be produced (see U.S. Pat. No. 4,816,567).

An antibody of this invention may also be a hybrid molecule formed from immunoglobulin sequences from different species (e.g., mouse and human) or from portions of immunoglobulin light and heavy chain sequences from the same species. An antibody may be a single-chain antibody or a humanized antibody. It may be a molecule that has multiple binding specificities, such as a bifunctional antibody prepared by any one of a number of techniques known to those of skill in the art including the production of hybrid hybridomas, disulfide exchange, chemical cross-linking, addition of peptide linkers between two monoclonal antibodies, the introduction of two sets of immunoglobulin heavy and light chains into a particular cell line, and so forth.

The antibodies of this invention may also be human monoclonal antibodies, for example those produced by immortalized human cells, by SCID-hu mice or other non-human animals capable of producing "human" antibodies, or by the expression of cloned human immunoglobulin genes. The preparation of humanized antibodies is taught by U.S. Pat. Nos. 5,777,085 and 5,789,554.

In sum, one of skill in the art, provided with the teachings of this invention, has available a variety of methods which may be used to alter the biological properties of the antibodies of this invention including methods which would increase or decrease the stability or half-life, immunogenicity, toxicity, affinity or yield of a given antibody molecule, or to alter it in any other way that may render it more suitable for a particular application.

Therapeutic Methods Using Nucleic Acids Encoding Essential Genes

Once a gene has been identified as essential in *S. cerevisiae,* the gene and its nucleotide sequence can be exploited in a number of ways so that the essential gene can be used as an antifungal target. One method is to use the primary sequence of the essential gene itself. For instance, antisense oligonucleotides can be produced which are complementary to the mRNA of the essential gene. Antisense oligonucleotides can be used to inhibit transcription or translation of an essential yeast gene. Production of antisense oligonucleotides effective for therapeutic use is well-known in the art, see Agrawal et al. (1997) *Pharmacology & Therapeutics* 76:151–60; Lavrovsky et al. (1997) *Biochemical and Molecular Medicine* 62:11–22; and Crooke (1998) *Biotechnology and Genetic Engineering Reviews* 15:121–57. Antisense oligonucleotides are often produced using derivatized or modified nucleotides in order to increase half-life or bioavailability.

The primary sequence of the essential gene can also be used to design ribozymes that can target and cleave specific essential gene sequences. There are a number of different types of ribozymes. Most synthetic ribozymes are generally hammerhead, Tetrahymena and hairpin ribozymes. Methods of designing and using ribozymes to cleave specific RNA species are known in the art, see Zhao et al. (1998) *Mol. Cell. Neurosci.* 11:92–97; Lavrovsky et al. (1997); and Eckstein (1997) *Ciba Foundation Symposium* 207–17. Although hammerhead ribozymes are generally ineffective in yeast (Castanotto et al. (1998) *Antisense & Nucleic Acid Drug Development* 8:1–13), other types of ribozymes may be effective as antifungal agents.

As discussed above, one can use essential yeast genes to identify genes critical for growth in insects, plants, humans and other mammals. Therefore, one can design ribozymes and antisense molecules to these genes in insects and plants for use as insecticides and herbicides, respectively. Similarly, one can design ribozymes and antisense molecules to genes important to proliferation in humans or other mammals for use as anti-proliferation drugs.

Methods Using Neutralizing Antibodies to Proteins Encoded by Essential Genes

The protein encoded by the essential gene can be used to elicit neutralizing antibodies for use as antifungal inhibitors, insecticides, herbicides or for anti-proliferation drugs. An antibody may be an especially good antifungal inhibitor, insecticide, herbicide or anti-proliferation drug if the gene of interest encodes a protein which is expressed on the cell surface, such as an integral membrane protein. Although polyclonal antibodies may be made, monoclonal antibodies are preferred. Monoclonal antibodies can be screened individually in order to isolate those that are neutralizing or inhibitory for the protein encoded by the essential gene. Monoclonal antibodies also may be screened for inhibition of a particular function of a protein. For instance, if it is known that the essential gene in yeast encodes a protein kinase, one can identify antibodies that inhibit kinase activity. Alternatively, if the specific function of an essential gene is unknown, one can measure inhibition of yeast proliferation using panels of antibodies. Similarly, one can screen antibodies which are directed against insect, plant or human proteins for inhibition of a particular activity or for inhibition of proliferation of appropriate cells.

Monoclonal antibodies which inhibit yeast growth in vitro may be humanized for therapeutic use using methods well-known in the art, see, e.g., U.S. Pat. Nos. 5,777,085 and 5,789,554. Monoclonal antibodies may also be engineered as single-chain antibodies using methods well-known in the art for therapeutic use, see, e.g., U.S. Pat. Nos. 5,091,513, 5,587,418, and 5,608,039.

Neutralizing antibodies may also be used diagnostically. For instance, the binding site of a neutralizing antibody to the protein encoded by the essential gene can be used to help identify domains that are required for the protein's activity. The information about the critical domains of an essential protein can be used to design inhibitors that bind to the critical domains of the essential protein. In addition, neutralizing antibodies can be used to validate whether a potential inhibitor of an essential protein inhibits the protein in in vitro assays.

Methods of Using Essential Genes To Identify Targets

Once an essential gene in yeast is identified, the Genome Reporter Matrix (see U.S. Pat. Nos. 5,569,588 and 5,777,888) can be used to identify critical functional attributes of the gene. The Genome Reporter Matrix is a library of yeast that contains several thousand yeast strains each of which contains a single gene fusion of a yeast gene to a reporter gene. Thus, each gene of the yeast genome is "tagged" by a reporter gene, and its transcription in response to a particular stimulus can be measured. In order to determine the particular transcripts an essential yeast gene modifies, one overexpresses the essential gene in the cells of the Genome Reporter Matrix. One may also express a conditional allele of the gene in the cells of the Genome Reporter Matrix. One may also express a conditional allele gene in the cells of the Genome Reporter Matrix and measure the response under the non- or semi-permissive condition. Then, one identifies a subset of genes that are either induced or repressed by overexpression of the essential gene. Methods for processing data using the Genome Reporter Matrix are also disclosed in U.S. Pat. Nos. 5,569,588 and 5,777,888. Once the genes that are regulated by an essential gene are identified, one can use this information in a number of ways to identify antifungal compounds. One may be able to ascertain what particular metabolic or signaling pathway an essential gene is part of. This knowledge may allow one to narrow the focus of a search for compounds that will target the essential gene. Alternatively, one may use the subset of cells expressing the regulated genes for screening potential antifungal compounds. For instance, if overexpression of the essential gene leads to an upregulation of particular genes, potential antifungal agents could be screened by looking for down-regulation of those genes. Conversely, if overexpression of the essential gene leads to downregulation of particular genes, antifungal agents could be screened by looking for upregulation of those genes.

Another method for isolating a potential antifungal agent of an essential gene target is to use information obtained from the "two-hybrid system" to identify and clone genes encoding proteins that interact with the polypeptide target encoded by the essential gene (see, e.g., Chien et al.,1991, *Proc. Natl. Acad. Sci. U.S.A.* 88(21):9578–82). The amino acid sequences of the polypeptides identified by the two-hybrid system can be used to design inhibitory peptides to the essential gene. Furthermore, the method may also identify other genes that are essential in yeast that may be good potential antifungal targets as well.

In a similar fashion, both the Genome Reporter Matrix system and the "two-hybird system" can be used to identify genes in other organisms that may be amenable to regulation by compounds for use as insecticides, herbicides and anti-proliferation drugs. For instance, one can overexpress a homologous insect gene in an insect Genome Reporter Matrix system and identify genes that are regulated by the insect gene. One can then screen compounds that upregulate or downregulate these regulated genes in order to identify potential insecticides. Similar plant and human Genome Reporter Matrix systems overexpressing essential or critical genes can be used in the same way to identify herbicides and anti-proliferative agents, respectively. The "two-hybrid" system using libraries of the appropriate species can also be used to identify insecticides, herbicides and/or anti-proliferative agents.

Other methods for identifying targets of genes and assaying up-regulation and/or down-regulation of genes may also be used (see, e.g., PCT publications WO 98/38329 dated Sep. 3, 1998, and WO 97/10365 dated Mar. 20, 1997).

Methods of Using Protein Targets

Recombinantly expressed purified proteins can be used to screen libraries of natural, semisynthetic or synthetic compounds. Particularly useful types of libraries include combinatorial small organic molecule libraries, phage display libraries, and combinatorial peptide libraries. Methods of determining whether components of the library bind to a particular polypeptide are well known in the art. In general, the polypeptide target is attached to solid support surface by non-specific or specific binding. Specific binding can be accomplished using an antibody which recognizes the protein that is bound to a solid support, such as a plate or column. Alternatively, specific binding may be through an epitope tag, such as GST binding to a glutathione-coated solid support, or IgG fusion protein binding to a Protein A solid support. Alternatively, the recombinantly expressed protein or fragments thereof may be expressed on the surface of phage, such as M13. A library in mobile phase is incubated under conditions to promote specific binding between the target and a compound. Compounds which bind to the target can then be identified. Alternately, the library is attached to a solid support and the polypeptide target is in the mobile phase.

Binding between a compound and target can be determined by a number of methods. The binding can be identified by such techniques as competitive ELISAs or RIAs, for example, wherein the binding of a compound to a target will prevent an antibody to the target from binding. These methods are well-known in the art, see, e.g., Harlow and Lane, supra. Another method is to use BiaCORE (BiaCORE) to measure interactions between a target and a compound using methods provided by the manufacturer. A preferred method is automated high throughput screening, see, e.g., Burbaum et al. (1997) *Current Opinion in Chemical Biology* 1:72–8; and Schullek et al. (1997) *Analytical Biochemistry* 246:20–29.

Once a compound that binds to a target is identified, one then determines whether the compound inhibits the activity of the target. For a compound that binds to a antifungal target, one can measure inhibition of proliferation or germination in yeast incubated with the potential antifungal compound. For a potential insecticide or herbicide, one can measure inhibition of proliferation of insect or plant cells, respectively. Alternatively, for a potential anti-proliferative drug, one could measure inhibition of proliferation of a mammalian cell after incubation with the potential anti-proliferative drug. If a biological function for the target protein is known, one could determine whether the compound inhibited the biological activity of the protein. For instance, if it is known that the target protein is a kinase, one can measure the inhibition of kinase activity in the presence of the potential inhibitor.

Another embodiment of the invention is to use the recombinantly expressed protein for rational drug design. The structure of the recombinant protein may be determined using x-ray crystallography or nuclear magnetic resonance (NMR). Alternatively, one could use computer modeling to determine the structure of the protein. The structure can be used in rational drug design to design potential inhibitory compounds of the target (see, e.g., Clackson (1998) *Curr. Opin. Struct. Biol.* 8:451–8; Mattos et al. (1996) *Nature Biotechnol.* 14:595–9; Hubbard (1997) *Curr. Opin. Biotechnol.* 8:696–700; Cunningham et al. (1997) *Curr. Opin. Struct. Biol.* 7:457–62; Kubinyi (1995) *Pharmazie* 50:647–62; Kleinberg et al. (1995) *Am. J. Health Syst. Pharm.* 52:1323–36.). Potential antifungal inhibitors can then be tested for inhibition of proliferation or germination in yeast, while potential anti-proliferative compounds can be tested for inhibition of mammalian, preferably human, cells. Similarly, potential herbicidal and insecticidal compounds can be tested for inhibition of plant and insect cells, respectively. In addition, rational drug design can be used to exploit differences in the sequences of the yeast gene and the host gene homolog.

Pharmaceutical Applications

Potential antifungal compounds can be tested in heterologous host cell systems (e.g., human cells) to verify they do not affect proliferation or other cell functions to a significant degree. For instance, potential antifungal compounds can be used in a mammalian Genome Reporter Matrix system to make sure that the compounds do not adversely alter gene transcription (e.g., in an undesirable way). Similarly, potential anti-proliferative compounds can be tested to be sure that they do not adversely affect functions other than proliferation. Potential herbicidal and insecticidal compounds can also be tested for potential side effects in mammalian, preferably human, cell systems, such as the Genome Reporter Matrix system, for potential side effects on cellular functions. Of course, certain changes in gene transcription may be inevitable and many of these will not be deleterious to the patient or host organism. Once lead compounds have been identified, these compounds can be refined further via rational drug design and other standard pharmaceutical techniques. Ultimately, compounds can be used as effective antifungal agents, anti-proliferative drugs, herbicides and pesticides.

The antifungal agents of this invention may be formulated into pharmaceutical compositions and administered in vivo at an effective dose to treat a particular fungal disease. Similarly, the anti-proliferative drugs of this invention may be formulated into pharmaceutical compositions and administered in vivo at an effective dose to treat a particular proliferative disorder. Determination of a preferred pharmaceutical formulation and a therapeutically efficient dose regiment for a given application is within the skill of the art taking into consideration, for example, the condition and weight of the patient, the extent of desired treatment and the tolerance of the patient for the treatment.

Administration of the antifungal or anti-proliferative agents of this invention, including isolated and purified forms, their salts or pharmaceutically acceptable derivatives thereof, may be accomplished using any conventionally accepted mode of administration. The pharmaceutical compositions of the present invention may be administered to a subject such as a plant or animal in order to treat anti-fungal diseases or proliferative disorders. Such animals to be treated by the pharmaceutical compositions of the present invention include humans, non-human mammals including but not limited to monkeys and other primates, dogs, cats, ferrets, guinea pigs, cattle, sheep, pigs, goats and horses, and birds. The anti-fungal or anti-proliferative agents of the present invention may further be used to prevent contamination of mammalian and non-mammalian cells (e.g., insect cells) grown in tissue culture by fungi, e.g., yeast, by incubating such cells in cell culture medium containing an effective amount of the agent.

The pharmaceutical compositions of this invention may be in a variety of forms, which may be selected according to the preferred modes of administration. These include, for example, solid, semi-solid and liquid dosage forms such as tablets, pills, powders, liquid solutions or suspensions, suppositories, and injectable and infusible solutions. The preferred form depends on the intended mode of administration and therapeutic application. Modes of administration may include oral, parenteral, subcutaneous, intravenous, intralesional or topical administration.

The antifungal or anti-proliferative agents of this invention may, for example, be placed into sterile, isotonic formulations with or without cofactors which stimulate uptake or stability. The formulation is preferably liquid, or may be lyophilized powder. For example, the inhibitors may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Alternatively, the composition may be pressurized and contain a compressed gas, such as nitrogen or a liquified gas propellant. The liquified propellant medium and indeed the total composition is preferably such that the active ingredient does not dissolve therein to any substantial extent.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The pharmaceutical compositions of this invention may also be administered using microspheres, microparticulate delivery systems or other sustained release formulations placed in, near, or otherwise in communication with affected tissues or the bloodstream. Suitable examples of sustained release carriers include semipermeable polymer matrices in the form of shaped articles such as suppositories or microcapsules. Implantable or microcapsular sustained release matrices include polylactides (U.S. Pat. No. 3,773,319; EP 58,481), copolymers of L-glutamic acid and gamma ethyl-L-glutamate (Sidman et al. (1985) *Biopolymers* 22:547–56; poly(2-hydroxyethyl-methacrylate) or ethylene vinyl acetate (Langer et al. (1981) *J. Biomed. Mater. Res.* 15:167–277; Langer (1982) *Chem. Tech.* 12:98–105).

The antifungal or anti-proliferative agents of this invention may also be attached to liposomes, which may optionally contain other agents to aid in targeting or administration of the compositions to the desired treatment site. Attachment of the antifungal or anti-proliferative agents to liposomes may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al. (1992) *J. Cell. Biochem.* Abst. Suppl. 16E:77).

Liposomes containing antifungal or anti-proliferative agents may be prepared by well-known methods (See, e.g. DE 3,218,121; Epstein et al. (1985) *Proc. Natl. Acad. Sci. U.S.A.* 82:3688–92; Hwang et al. (1980) *Proc. Natl. Acad. Sci. U.S.A.* 77:4030–34; U.S. Pat. Nos. 4,485,045 and 4,544,545). Ordinarily the liposomes are of the small (about 200–800 Angstroms) unilamellar type in which the lipid content is greater than about 30 mol. % cholesterol. The proportion of cholesterol is selected to control the optimal rate of MAG derivative and inhibitor release.

The compositions also will preferably include conventional pharmaceutically acceptable carriers well known in the art (see, e.g., *Remington's Pharmaceutical Sciences*, 16th Edition, 1980, Mac Publishing Company). Such pharmaceutically acceptable carriers may include other medicinal agents, carriers, genetic carriers, adjuvants, excipients, etc., such as human serum albumin or plasma preparations. The compositions are preferably in the form of a unit dose and will usually be administered one or more times a day.

EXAMPLE 1

Construction of the YFR003C Mutant Strain and Analysis of Transformants

Construction of the YER003C Mutant Strain
PCR for Chr 6 Round 1a Construct

All of the primers (both for construct PCR and analysis of the mutant) were organized in a 96-well format. The complete set of primers for each gene occupied a defined position on the 96-well plate (e.g. the UPTAG primer for YFR003C was in position F9 of the UPTAG block, and the analytical B primer for YFR003C was in position F9 of the B block). The sequences of the construct primers for the YFR003C locus are shown in FIG. 3. The UPTAG and DOWNTAG primers were resuspended in TE (10 mM Tris-HCl, 1 mM EDTA) to a concentration of 5 $\mu$M (UPTAG) and 7 $\mu$M (DOWNTAG). A PCR master mix for the entire set 6 was prepared by combining: 4263 $\mu$l H2O, 525 $\mu$l 10× Taq buffer (100 mM Tris-HCl (pH 8.5), 500 mM KCl, 15 mM MgCl2), 52.5 $\mu$l 20 mM dNTPs, 4 $\mu$l pFA6A-KanMX4 plasmid (approx. 2.5 $\mu$g), and 52.5 $\mu$l Taq Polymerase (5 units/$\mu$l). For each of the 96 reactions, 46.6 $\mu$l of the PCR master mix was transferred to the PCR plate with 3.4 $\mu$l primer mixes (2 $\mu$l UPTAG and 1.4 $\mu$l DOWNTAG, approx. 10 pmole each). The PCR reactions were performed using a Perkin Elmer 9600 PCR machine. The PCR conditions were as follows:

(1) initial denaturation at 94° C. for 3 minutes,
(2) 94° C. for 30 seconds,
(3) 54° C. for 30 seconds,
(4) 72° C. for 1 minute,
(5) cycle from step #2 for 25 times,
(6) perform final elongation at 72° C. for 3 minutes.

To visualize the PCR reactions, 4 $\mu$l loading buffer (12.5% glycerol, 0.1 mM EDTA, dye) was transferred to each well of a 96-well plate. 6 $\mu$l of each PCR reaction was then mixed with the loading buffer and run on a 1% agarose TBE gel (with 0.4 $\mu$g/ml ethidium bromide), and visualized with UV.
PCR for Chr 6 Round 2b Construct The second round primers were resuspended in TE to a concentration of 23 $\mu$M for UPSTREAM45 and 18 $\mu$M for DOWNSTREAM45. 2 $\mu$l of each round 1a PCR product was transferred to the corresponding well of a 96-well PCR plate. Primers 3.5 $\mu$l UPSTREAM45 and 4.4 $\mu$l DOWNSTREAM45 (approx. 80 pmole each) were added to the PCR plate. A PCR master mix was prepared by combining: 8200 $\mu$l H2O, 1050 $\mu$l 10× Taq buffer, 105 $\mu$l 20 mM dNTPs, and 105 $\mu$l Taq polymerase. 90.1 $\mu$l of the master mix was transferred to each well of the PCR plate. The PCR reactions were performed using a Perkin Elmer 9600 PCR machine. The PCR conditions were as follows:

(1) initial denaturation at 94° C. for 3 minutes,
(2) 94° C. for 30 seconds,
(3) 54° C. for 30 seconds,
(4) 72° C. for 1 minute,
(5) cycle from step #2 for 25 times,
(6) perform final elongation at 72° C. for 3 minutes.

A 6 $\mu$l sample of each reaction was visualized by agarose gel electrophoresis as before. The remainder of each round 2 PCR reaction was purified by precipitation. 10 $\mu$l 3M NaOAc and 100 $\mu$l isopropanol was transferred to each well of a 96-well plate. Then 90 $\mu$l of the round 2 PCR reactions were transferred to the corresponding wells of the NaOAc/isopropanol plated and mixed. The plate was then incubated at −20° C. for 20 minutes, and centrifuged at 3400 rpm in a Sorvall RC-3B centrifuge for 30 minutes. The supernatants were removed and the DNA pellets were allowed to air dry. Shortly before the yeast transformations, the construct PCR products were resuspended in 30 $\mu$l TE.
Transformation of Yeast The construct PCR products were transformed into two *S. cerevisiae* strains: a haploid strain R174 (also known as BY4741, MATa his3$\Delta$1 leu2$\Delta$0 met15$\Delta$0 ura3$\Delta$0) and a diploid strain R176 (also known as BY4743, MATa/MAT$\alpha$ his3$\Delta$1/his3$\Delta$1 leu2$\Delta$0/leu2$\Delta$0 met15$\Delta$0/MET15 LYS2/lys2$\Delta$0 ura3$\Delta$0/ura3$\Delta$0) (Brachmann et al., 1998). The yeast transformations were performed in a 96-well format, and the procedure was adapted from the standard lithium acetate method (Ito et al., 1983; Schiestl & Gietz, 1989), as described below. Two days before the transformations fresh cultures of R174 and R176 were inoculated from the frozen stocks in 3 ml YPD media and allowed to grow overnight at 30° C.; media and standard growth techniques were used (see Guthrie & Fink, 1991; Kaiser et al. (1994) *Methods in Yeast Genetics. A Cold Spring Harbor Laboratory Manual* (Cold Spring Harbor, N.Y.: Cold Spring Harbor Laboratory Press); Rose et al. (1989) *Laboratory Course Manual for Methods in Yeast Genetics* (Cold Spring Harbor, N.Y.: Cold Spring Harbor Laboratory Press)). The day prior to the transformations the cultures were diluted 1:50 in YPD and placed at 30° C. until they reached log phase growth. These actively dividing cells were then used to inoculate 100 ml YPD cultures and placed at 30° C. The volume of the inoculum was calculated such that the cultures would still be in log phase growth after 12 hours. The day of the transformations, the cultures were harvested and made competent. The optical density (O.D.) of the cultures was measured with a spectrophotometer (Hewlett-Packard 8452A Diode Array Spectrophotometer) at a wavelength of 600 nm to ensure that the cultures were in log phase growth (R174 O.D.600=2.04, R176 O.D.600=1.75). The cells were pelleted in a Sorvall RC-5C centrifuge with an SLA-1500 rotor at 2000 rpm for 5 minutes. The cells were washed with 100 ml 100 mM lithium acetate (LiOAc), pelleted again, and resuspended in 2 ml 100 mM LiOAc.

A LiOAc/PEG solution was prepared by dissolving 15 g polyethylene glycol (PEG 3350) in 16.5 ml $H_2O$ followed by filter sterilization. 12 ml of this PEG solution was then added to 1.5 ml sterile $H_2O$ and 1.5 ml sterile 100 mM LiOAc. The 2 ml competent cells were mixed with 22 µl carrier DNA (10 mg/ml sheared and boiled salmon sperm DNA). 10 µl of the round 2b construct PCR products was transferred to the corresponding well of a 96-well U-bottom plate. 25 µl of the cell/carrier DNA mix was added to each well. The plate was then incubated at 30° C. for 15 minutes. 150 µl of the LiOAc/PEG solution was then added to each well and mixed by pipetting up and down. The plate was then incubated at 30° C. for 60 minutes. Next, 17 µl DMSO was added to each well and the cells were heat shocked by placing the plate at 42° C. for 15 minutes. The cells were then pelleted in a Beckman GS-6R centrifuge at 1000 rpm for 3 minutes. The liquid was removed and the cells were resuspended in 200 µl YPD (each well). The cells were allowed to recover for 4 hours at 30° C. on a rotary shaker to express the KanMX marker. Transformants were selected for by plating the cells on YPD-G-418 (300 µg/ml) plates followed by growth at 30° C. Transformants were then colony-purified by restreaking to a second YPD-G-418 plate.

Analysis of Transformants

Whole Cell PCR Analysis

The transformants were analyzed utilizing whole cell PCR. The sequences of the six primers used for the analysis of the YFR003C locus (four gene specific, and two marker specific) are shown in FIG. 3. A sample of cells from a colony-purified transformant was picked with a pipet tip (not a toothpick), and smeared into the bottom of a PCR tube. Generally the cells were less than 3 days old. The tubes were then microwaved on high for 1 minute, and placed on ice in a metal block. A PCR master mix was prepared. For each reaction, the mix contained: 2 µl 2.5 mM dNTPs, 2 µl 10× Klentaq™ PCR reaction buffer (400 mM Tricine-KOH (pH 9.2), 150 mM KOAc, 35 mM Mg(OAc)$_2$, 750 µg/ml bovine serum albumin), 0.5 µl Klentaq™ (Clontech), and 13.5 µl $H_2O$. 18 µl of the PCR master mix was added to each tube containing the microwaved cells. Oligonucleotide primer pairs were then added using 1 µl of a 10 µM solution of each of the two primers of the pair. The following primer pairs were used: A/B, A/KanB, C/D, KanC/D, and A/D. The reactions were mixed by pipetting up and down. When the thermocycler had reached 94° C., the tubes in the metal block were taken off the ice and placed in the thermocycler. This is known as "hot start" PCR. The PCR reactions were generally performed using an MJ Research PTC-100 thermocycler using the following program:
 (1) initial denaturation at 94° C. for 10 minutes,
 (2) 94° C. for 30 seconds,
 (3) 58° C. for 30 seconds,
 (4) 68° C. for 1 minutes 30 seconds,
 (5) cycle from step #2 for 35 times For the A/D primer pairs, the extension time (step #4) was increased to 3 minutes to compensate for the larger product that is produced by these flanking primers. Following the PCR, 2 µl of 10× loading buffer was added to each tube. 10 µl was removed and run on a 0.8% agarose TAE gel (with 0.4 µg/ml ethidium bromide), and visualized with UV. The sizes of the various PCR products were then compared with that which was expected. If all five analytical PCR reactions produced the expected results, it was deemed that the correct gene deletion ("knock-out") had been constructed.

Tetrad Analysis

Tetrad analysis was performed on the heterozygous mutant diploids following sporulation. Freshly grown cells were transferred to sporulation medium (1% KOAc (w/v), 20 µg/ml uracil, 20 µg/ml histidine, 40 µg/ml leucine) and incubated at room temperature for a minimum of 7 days. The asci of the tetrads were partially digested with zymolyase-20T (from Arthrobacter luteus; ICN). 100 µl of the sporulation culture was incubated with 1 µl zymolyase (10 mg/ml, 20 units/mg) for 10 minutes at room temperature. 15 µl was then dribbled onto a YPD plate and allowed to dry.

The tetrads were dissected and arrayed onto the YPD plate (Sherman & Wakem, 1991) utilizing a Narishige micromanipulator mounted onto the stage of an Olympus BH-TU microscope. Four spores of each tetrad were separated and placed in a vertical line on the surface of a YPD plate. The spores were allowed to germinate and grow at 30° C. for 2 days and then replica-plated to the following plates using sterile velveteens:
 (1) YPD,
 (2) YPD-G-418,
 (3) YM-Ura His Leu Met Lys,
 (4) YM-Ura His Leu Lys,
 (5) YM-Ura His Leu Met,
 (6) YM-MATa lawn (ABY57),
 (7) YM-MATα lawn (ABY58).

The plates were incubated at 30° C. and the tetrads were scored for growth. The heterozygous loci (MAT, MET15, and LYS2) showed the expected segregation. The details of the tetrad analysis involving the YFR003C mutation are described in the section "Phenotypic Analysis of the YFR003C Mutant Strain" (below).

Phenotypic Analysis of the YFR003C Mutant Strain

Figure 10:
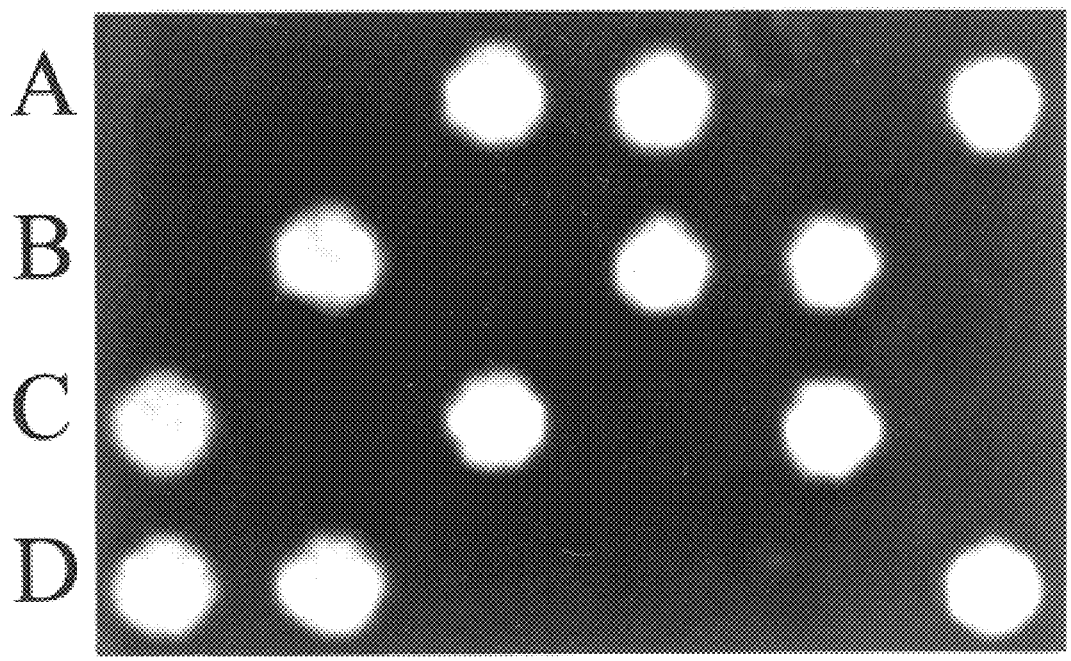
FIG. 10. Lethality of a YFR003C null mutation. A diploid strain containing a heterozygous null mutation of the YFR003C gene (marked by the KanMX gene conferring resistance to the drug G-418) was sporulated and dissected. The four spores of each tetrad were placed in a vertical line (labeled A, B, C and D), and allowed to germinate on rich medium. Six complete tetrads are shown. The observed lethality co-segregated with G-418 resistance, indicating that the lethality was due to the KanMX-marked YFR003C deletion mutation.

Tetrad analysis of the heterozygous yfr003cΔ::KanMX null mutation (R7444) demonstrated that the gene product was essential for germination and/or vegetative growth (FIG. 10). This was consistent with the inability to construct the YFR003C mutation in the haploid strain. Of the six tetrads analyzed, all segregated two live and two dead spores, indicating that there was a single heterozygous lethal mutation in the diploid strain. All of the twelve living spores were sensitive to G-418, indicating that they had inherited the wild-type allele of the YFR003C gene and that all of the dead spores had inherited the yfr003cΔ::KanMX null allele.

Sequence Comparisons

The YFR003C ORF contains 468 bp (FIG. 4), and is predicted to encode a protein of 155 amino acids (FIG. 5). For the sequence analysis for Yfr003cp, the blastp version 2.0.4 (gapped) algorithm (Altschul et al., 1997) at the NCBI web site was used. The search of the amino acid sequence of Yfr003c was performed against the non-redundant database (defined as "nr" at the NCBI web site) and/or the Swiss protein database. Default parameters were used. The default setting of filtering the query sequence for regions of low complexity was also used. A slightly different algorithm, tblastn, was also used to search the same databases, as well as the EST database, using the amino acid sequence of Yfr003cp. The tblastn algorithm performs a dynamic comparison of the amino acid sequence of Yfr003cp against a nucleotide database that has been translated in all six possible reading frames. Although this algorithm is useful because it can identify homologs for nucleotide sequences that have not been translated, the results of this type of search must be carefully checked because many of the possible translations do not represent amino acid sequences of a protein found in nature. The Yfr003cp protein has very weak homologs in C. elegans and C. albicans (FIGS. 6–8).

EXAMPLE 2

Construction of the YGR277c Mutant Strain and Analysis of Transformants

Construction of the YGR277c Mutant Strain
PCR for Chr 7 Round 1a Construct

The PCR conditions for set 7 were essentially the same as 6, with only minor adjustments. Again, all of the primers were organized in a 96-well format. The sequences of the construct primers for the YGR277C locus are shown in FIG. 11. The UPTAG and DOWNTAG primers were resuspended in TE to a concentration of 8.8 $\mu$M (UPTAG) and 8.1 $\mu$M (DOWNTAG). A PCR master mix was prepared by combining: 4379 $\mu$l H$_2$O, 525 $\mu$l 10× Taq buffer, 52.5 $\mu$l 20 mM dNTPs, 4 $\mu$l pFA6A-KanMX4 plasmid (approx. 2.5 $\mu$g), and 52.5 $\mu$l Taq Polymerase (5 units/$\mu$l). For each of the 96 reactions, 47.7 $\mu$l of the PCR master mix was transferred to the PCR plate with 2.3 $\mu$l primer mixes (1.1 $\mu$l UPTAG and 1.2 $\mu$l DOWNTAG, approx. 10 pmole each). The PCR reactions were performed using a Perkin Elmer 9600 PCR machine. The PCR conditions were as follows:

(1) initial denaturation at 94° C. for 3 minutes,
(2) 94° C. for 30 seconds,
(3) 54° C. for 30 seconds,
(4) 72° C. for 1 minute,
(5) cycle from step #2 for 20 times,
(6) final elongation at 72° C. for 3 minutes.

The PCR reactions were visualized by gel electrophoresis as before.

PCR for Chr 7 Round 2a Construct

The conditions for the second round of construct PCR were essentially as described above in Example 1. The second round primers were resuspended in TE to a concentration of 15 $\mu$M for UPSTREAM45 and 18 $\mu$M for DOWNSTREAM45. 2 $\mu$l of each round 1a PCR product was transferred to the corresponding well of a 96-well PCR plate. 2.7 $\mu$l of primer UPSTREAM45 and 2.2 $\mu$l of primer DOWNSTREAM45 (approx. 40 pmole each) were added. A PCR master mix was prepared by combining: 8516 $\mu$l H2O, 1050 $\mu$l 10× Taq buffer, 105 $\mu$l 20 mM dNTPs, and 105 $\mu$l Taq polymerase. 93.1 $\mu$l of the master mix was transferred to each well of the PCR plate with the primers. The PCR conditions were as follows:

(1) initial denaturation at 94° C. for 3 minutes,
(2) 94° C. for 30 seconds,
(3) 54° C. for 30 seconds,
(4) 72° C. for 1 minute,
(5) cycle from step #2 for 20 times,
(6) final elongation at 72° C. for 3 minutes.

A 6 $\mu$l sample of each reaction was visualized by agarose gel electrophoresis as before. The remainder of each round 2 PCR reaction was purified by precipitation as before. Shortly before yeast transformations, the construct PCR products were resuspended in 30 $\mu$l TE.

Transformation of Yeast

The yeast transformation protocol for set 7 was the same as that used to transform set 6. Again, both haploid (R174) and diploid (R176) strains were transformed. The cultures were harvested at the following densities: R174 O.D.600= 1.58, and R176 O.D.600=1.43. As before, following the transformations the cells were allowed to recover in YPD at 30° C. for 4 hours prior to being plated on YPD-G-418 (300 $\mu$g/ml) plates. The transformants were colony-purified by restreaking to a second YPD-G-418 plate.

Analysis of Transformants
Whole Cell PCR Analysis

Analysis of the set 7 mutations (including YGR277C) was performed by whole cell PCR exactly as described in Example 1. This is a standard technique for the analysis of mutant strains, during their construction and otherwise (i.e. for quality control, etc.). The sequences of the six primers used for the analysis of the YGR277C locus (four gene specific, and two marker specific) are shown in FIG. 11. As always, all five analytical PCR primer pairs (A/B, A/KanB, C/D, KanC/D, and A/D) had to give the expected results in order for a mutant to be deemed correct.

Tetrad Analysis

Tetrad analysis was performed essentially as described in Example 1. The analysis was performed on the set 7 heterozygous diploids following at least seven days of sporulation at room temperature. The tetrads were digested with Zymolyase and dissected on YPD plates, followed by growth at 30° C. The germinated tetrads were scored for G-418 resistance, Met auxotrophy, Lys auxotrophy, and mating type by replica-plating on the same seven plates as described in Example 1, followed by growth at 30° C. The heterozygous loci (MAT, MET15, and LYS2) showed the expected segregation. The details of the tetrad analysis involving the YGR277C mutation are described in the section "Phenotypic Analysis of the YGR277C Mutant Strain" (below).

Phenotypic Analysis of the YGR277C Mutant Strain

Figure 15:
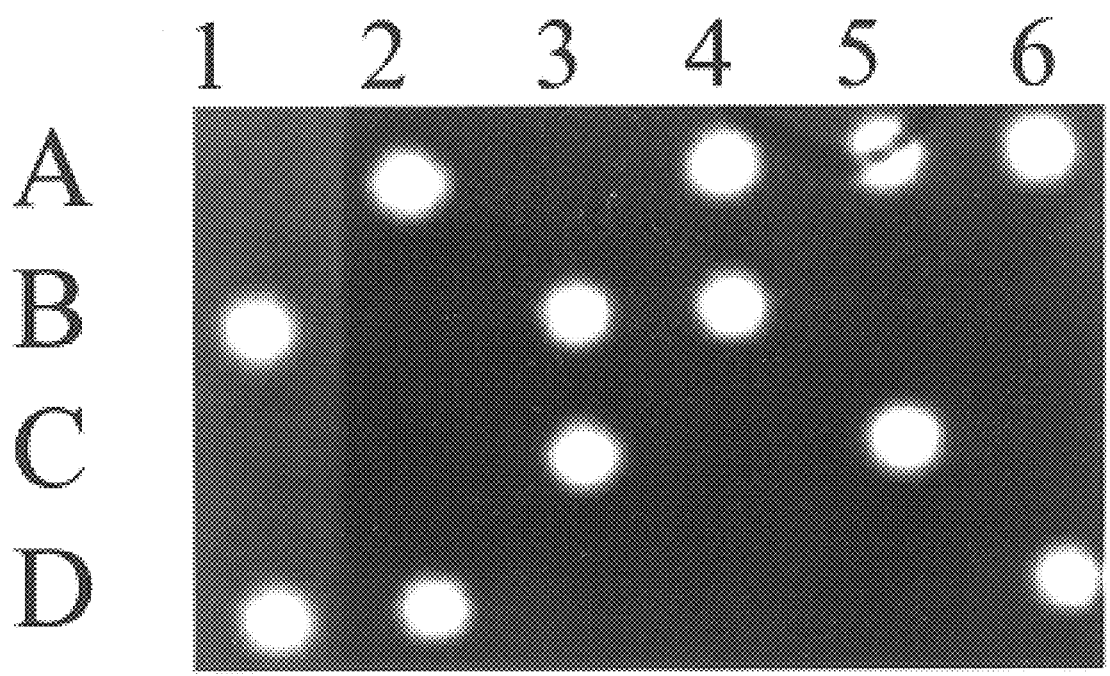
FIG. 15. Lethality of a YGR277C null mutation. A diploid strain containing a heterozygous null mutation of the YGR277C gene (marked by the KanMX gene conferring resistance to the drug G-418) was sporulated and dissected. The four spores of each tetrad were placed in a vertical line (labeled A, B, C and D) and allowed to germinate on rich medium. Six complete tetrads are shown. The observed lethality co-segregated with G-418 resistance, indicating that the lethality was due to the KanMX-marked YGR277C deletion mutation.

Tetrad analysis of the heterozygous ygr277cΔ::KanMX null mutation (R7311) demonstrated that this hypothetical open reading frame not only was in fact a gene, but also that this gene was essential for germination and/or vegetative growth. This was consistent with the inability to construct the YGR277C mutation in the haploid strain. A total of six tetrads were analyzed by dissection. All segregated two live and two dead spores, indicating that there was a single heterozygous lethal mutation in the diploid strain (FIG. 15). All of the twelve living spores were sensitive to G-418, indicating that they had inherited the wild-type allele of the YGR277C gene and that all of the dead spores had inherited the ygr277cΔ::KanMX null allele.

Sequence Comparisons

The YGR277C ORF contains 918 bp (FIG. 12), and is predicted to encode a protein of 305 amino acids (FIG. 13). The sequence analysis of the YGR277C encoded protein was performed using the blastp (version 2.0.4, gapped) and the tblastn algorithms at the NCBI web site. The default settings were used. Blastp was used to search the nr and/or the Swiss protein databases; tblastn was used to search the EST database. The predicted YGR277C encoded protein has Type 2 homologs in Arabidopsis, *S. pombe,* Pyrococcus, Methanococcus, and Methanobacterium (FIG. 14).

EXAMPLE 3

Construction of the YGR278w Mutant Strain and Analysis of Transformants

Construction of the YGR278w Mutant Strain
PCR Conditions

The Chr 7 Round 1a construct PCR and Round 2a construct PCR reactions are described in Example 2. The sequences of the four primers used for the construct PCR of YGR278W are shown in FIG. 16.
Transformation of Yeast The yeast transformation protocol for set 7 was the same as that used to transform set 6 (Example 1). Both haploid (R174) and diploid (R176) strains were transformed. The cultures were harvested at the following densities: R174 O.D.$_{600}$=1.58, and R176 O.D.$_{600}$=1.43. Following the transformations, the cells were allowed to recover in YPD at 30° C. for four hours prior to being plated on YPD-G-418 (300 μg/ml) plates. The transformants were colony-purified by restreaking to a second YPD-G-418 plate.

Analysis of Transformants
Whole Cell PCR Analysis

Figure 20:
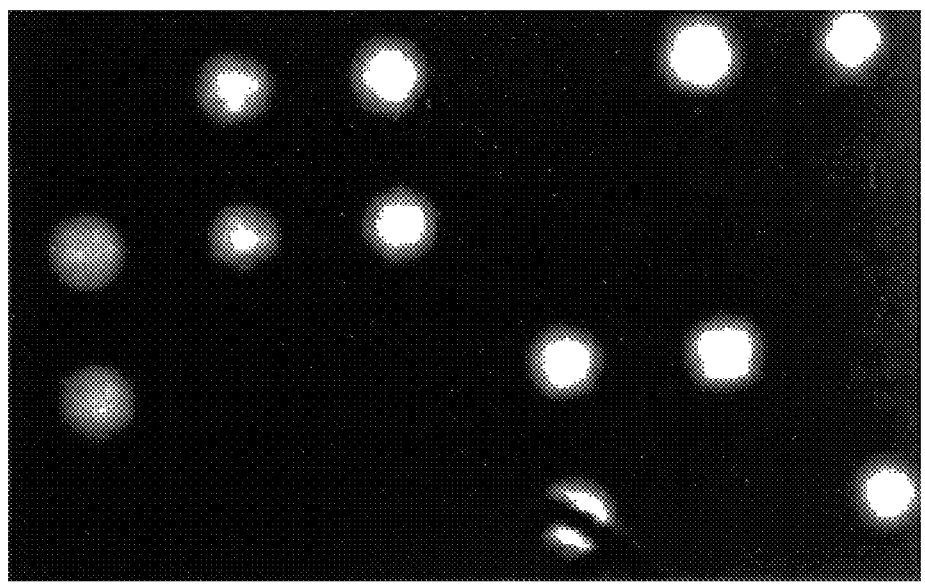
FIG. 20. Lethality of a YGR278W null mutation. A diploid strain containing a heterozygous null mutation of the YGR278W gene (marked by the KanMX gene conferring resistance to the drug G-418) was sporulated and dissected. The four spores of each tetrad were placed in a vertical line (labeled A, B, C and D) and allowed to germinate on rich medium. Six complete tetrads are shown. The observed lethality co-segregated with G-418 resistance, indicating that the lethality was due to the KanMX-marked YGR278W deletion mutation.

Analysis of the set 7 mutations (including YGR278W) was performed by whole cell PCR exactly as described in Example 1. The sequences of the six primers used for the analysis of the YGR278W locus (four gene specific, and two marker specific) are shown in FIG. 16. All five analytical PCR primer pairs (A/B, A/KanB, C/D, KanC/D, and A/D) had to give the expected results in order for a mutant to be deemed correct.
Tetrad Analysis Tetrad analysis was performed on the set 7 heterozygous diploids following at least seven days of sporulation at room temperature. The tetrads were digested with Zymolyase and dissected on YPD plates, followed by growth at 30° C. The germinated tetrads were then scored for G-418 resistance, Met auxotrophy, Lys auxotrophy, and mating type by replica-plating to the same seven plates as in Example 1, followed by growth at 30° C. The heterozygous loci (MAT, MET15, and LYS2) showed the expected segregation. The details of the tetrad analysis involving the YGR278W mutation are described in the section "Phenotypic Analysis of the YGR278W Mutant Strain" (below).
Phenotypic Analysis of the YGR278W Mutant Strain Tetrad analysis of the heterozygous ygr278wΔ::KanMX null mutation (R9861) demonstrated that this hypothetical open reading frame not only was in fact a gene, but also that this gene was essential for germination and/or vegetative growth. This was consistent with the inability to construct the YGR278W mutation in the haploid strain. A total of six tetrads were analyzed by dissection. All segregated two live and two dead spores, indicating that there was a single heterozygous lethal mutation in the diploid strain (FIG. 20). All of the twelve living spores were sensitive to G-418, indicating that they had inherited the wild-type allele of the YGR278W gene and that all of the dead spores had inherited the ygr278wΔ::KanMX null allele.
Sequence Comparisons The YGR278W ORF contains 1,734 bp (FIG. 17), and is predicted to encode a protein of 577 amino acids (FIG. 18). The sequence analysis of the YGR278W encoded protein was performed using the blastp (version 2.0.4, gapped) and the tblastn algorithms at the NCBI web site. The default settings were used. Blastp was used to search the nr (non redundant) and/or the Swiss protein databases; tblastn was used to search the EST database. The predicted YGR278W encoded protein has Type 1 homologs in *S. pombe,* and *C. elegans,* and a Type 2 homolog in its own genome (FIG. 19) and is a protein of unknown function.

EXAMPLE 4

Construction of the YKR071c Mutant Strain and Analysis of Transformants

Construction of the YKR071c Mutant Strain
PCR for Chr 11 Round 1a Construct

The PCR conditions for set 11 were essentially the same as 6, with only minor adjustments. Again, all of the primers were organized in a 96-well format. The sequences of the construct primers for the YKR071C locus are shown in FIG. 21. The UPTAG and DOWNTAG primers were resuspended in TE to a concentration of 8.8 μM (UPTAG) and 8.1 μM (DOWNTAG). A PCR master mix was prepared by combining: 4379 μl H$_2$O, 525 μl 10× Taq buffer, 52.5 μl 20 mM dNTPs, 4 μl pFA6A-KanMX4 plasmid (approx. 2.5 μg), and 52.5 μl Taq Polymerase (5 units/μl). For each of the 96 reactions, 47.7 μl of the PCR master mix was transferred to the PCR plate with 2.3 μl primer mixes (1.1 μl UPTAG and 1.2 μl DOWNTAG, approx. 10 pmole each). The PCR reactions were performed using a Perkin Elmer 9600 PCR machine. The PCR conditions were as follows:
  (1) initial denaturation at 94° C. for 3 minutes,
  (2) 94° C. for 30 seconds,
  (3) 54° C. for 30 seconds,
  (4) 72° C. for 1 minute,
  (5) cycle from step #2 for 20 times,
  (6) final elongation at 72° C. for 3 minutes.

The PCR reactions were visualized by gel electrophoresis as before.
PCR for Chr 11 Round 2a Construct The conditions for the second round of construct PCR were essentially as described above in Example 1. The second round primers were resuspended in TE to a concentration of 15 μM for UPSTREAM45 and 18 μM for DOWNSTREAM45. 2 μl of each round 1a PCR product was transferred to the corresponding well of a 96-well PCR plate. 2.7 μl of primer UPSTREAM45 and 2.2 μl of primer DOWNSTREAM45 (approx. 40 pmole each) were added. A PCR master mix was prepared by combining: 8516 μl H2O, 1050 μl 10× Taq buffer, 105 μl 20 mM dNTPs, and 105 μl Taq polymerase. 93.1 μl of the master mix was transferred to each well of the PCR plate with the primers. The PCR conditions were as follows:
  (1) initial denaturation at 94° C. for 3 minutes,
  (2) 94° C. for 30 seconds,
  (3) 54° C. for 30 seconds,
  (4) 72° C. for 1 minute,
  (5) cycle from step #2 for 20 times,
  (6) final elongation at 72° C. for 3 minutes.

A 6 μl sample of each reaction was visualized by agarose gel electrophoresis as before. The remainder of each round 2 PCR reaction was purified by precipitation as before. Shortly before yeast transformations, the construct PCR products were resuspended in 30 μl TE.
Transformation of Yeast The yeast transformation protocol for set 11 was the same as that used to transform set 6. Again, both haploid (R174) and diploid (R176) strains were transformed. The cultures were harvested at the following densities: R174 O.D.600= 1.58, and R176 O.D.600=1.43. As before, following the transformations the cells were allowed to recover in YPD at 30° C. for 4 hours prior to being plated on YPD-G-418 (300 μg/ml) plates. The transformants were colony-purified by restreaking to a second YPD-G-418 plate.

Analysis of Transformants
Whole Cell PCR Analysis

Analysis of the set 11 mutations (including YKR071C) was performed by whole cell PCR exactly as described in Example 1. This is a standard technique for the analysis of mutant strains, during their construction and otherwise (i.e. for quality control, etc.). The sequences of the six primers used for the analysis of the YKR071C locus (four gene specific, and two marker specific) are shown in FIG. 21. As always, all five analytical PCR primer pairs (A/B, A/KanB, C/D, KanC/D, and A/D) had to give the expected results in order for a mutant to be deemed correct.

Tetrad Analysis

Tetrad analysis was performed essentially as described in Example 1. The analysis was performed on the set 11 heterozygous diploids following at least seven days of sporulation at room temperature. The tetrads were digested with Zymolyase and dissected on YPD plates, followed by growth at 30° C. The germinated tetrads were scored for G-418 resistance, Met auxotrophy, Lys auxotrophy, and mating type by replica-plating on the same seven plates as described in Example 1, followed by growth at 30° C. The heterozygous loci (MAT, MET15, and LYS2) showed the expected segregation. The details of the tetrad analysis involving the YKR071C mutation are described in the section "Phenotypic Analysis of the YKR071C Mutant Strain" (below).

Phenotypic Analysis of the YKR071C Mutant Strain

Figure 27:
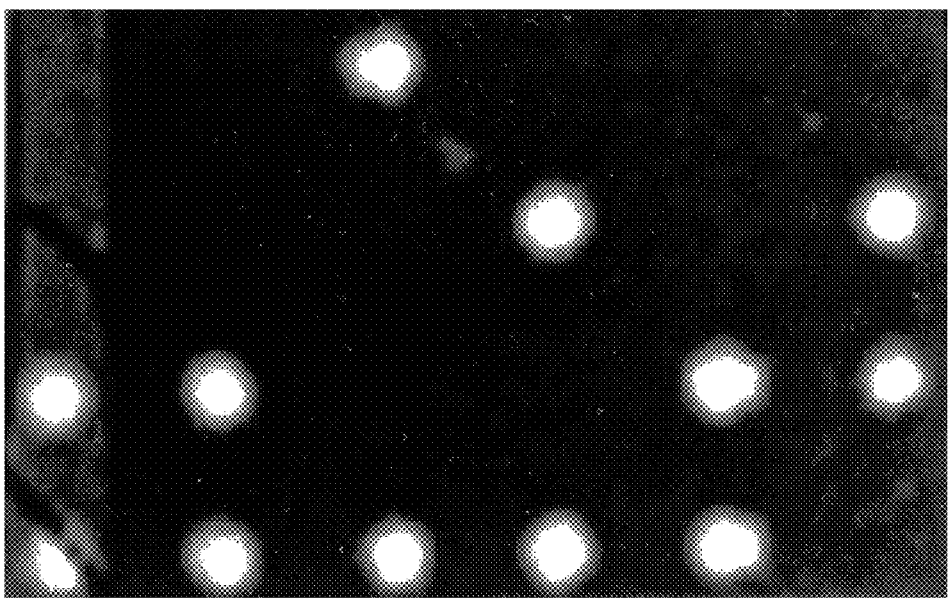
FIG. 27. Lethality of a YKR071C null mutation. A diploid strain containing a heterozygous null mutation of the YKR071C gene (marked by the KanMX gene conferring resistance to the drug G-418) was sporulated and dissected. The four spores of each tetrad were placed in a vertical line (labeled A, B, C and D) and allowed to germinate on rich medium. Six complete tetrads are shown. The observed lethality co-segregated with G-418 resistance, indicating that the lethality was due to the KanMX-marked YKR071C deletion mutation.

Tetrad analysis of the heterozygous ykr071cΔ::KanMX null mutation (R9534) demonstrated that this hypothetical open reading frame not only was in fact a gene, but also that this gene was essential for germination and/or vegetative growth. This was consistent with the inability to construct the YKR071C mutation in the haploid strain. A total of six tetrads were analyzed by dissection. All segregated two live and two dead spores, indicating that there was a single heterozygous lethal mutation in the diploid strain (FIG. 27). All of the twelve living spores were sensitive to G-418, indicating that they had inherited the wild-type allele of the YKR071C gene and that all of the dead spores had inherited the ykr071cΔ::KanMX null allele.

Sequence Comparisons

The YKR071C ORF contains 1,047 bp (FIG. 22), and is predicted to encode a protein of 348 amino acids (FIG. 23). The sequence analysis of the YKR071C encoded protein was performed using the blastp (version 2.0.4, gapped) and the tblastn algorithms at the NCBI web site. The default settings were used. Blastp was used to search the nr and/or the Swiss protein databases; tblastn was used to search the EST database. The predicted YKR071C encoded protein has a Type 2 homolog in *S. pombe* (FIG. 24). A 30 amino acid polypeptide fragment of the protein encoded by YKR071C has 70% sequence identity (and 86% sequence homology) with a 30 amino acid polypeptide of an unknown gene product from *H. sapiens* (FIG. 25). The protein encoded by YKR071C also has weak sequence homology to the *H. sapiens* chemokine STCP-1 (FIG. 26).

EXAMPLE 5

Construction of the YKR079c Mutant Strain and Analysis of Transformants

Construction of the YKR079c Mutant Strain
PCR Conditions

The Chr 11 Round 1a construct PCR and Round 2a construct PCR reactions are described in Example 4. The sequences of the four primers used for the construct PCR of YKR079C are shown in FIG. 28.

Transformation of Yeast

The yeast transformation protocol for set 11 was the same as that used to transform set 6 (Example 1). Both haploid (R174) and diploid (R176) strains were transformed. The cultures were harvested at the following densities: R174 O.D.$_{600}$=1.58, and R176 O.D.$_{600}$=1.43. Following the transformations the cells were allowed to recover in YPD at 30° C. for four hours prior to being plated on YPD-G-418 (300 μg/ml) plates. The transformants were colony-purified by restreaking to a second YPD-G-418 plate.

Analysis of Transformants
Whole Cell PCR Analysis

Analysis of the set 11 mutations (including YKR079C) was performed by whole cell PCR exactly described in Example 1. The sequences of the six primers used for the analysis of the YKR079C locus (four gene specific, and two marker specific) are shown in FIG. 28. All five analytical PCR primer pairs (A/B, A/KanB, C/D, KanC/D, and A/D) had to give the expected results in order for a mutant to be deemed correct.

Tetrad Analysis

Tetrad analysis was performed on the set 11 heterozygous diploids following at least seven days of sporulation at room temperature. The tetrads were digested with Zymolyase and dissected on YPD plates, followed by growth at 30° C. The germinated tetrads were then scored for G-418 resistance, Met auxotrophy, Lys auxotrophy, and mating type by replica-plating to the same seven plates as in Example 1, followed by growth at 30° C. The heterozygous loci (MAT, MET15, and LYS2) showed the expected segregation. The details of the tetrad analysis involving the YKR079C mutation are described in the section "Phenotypic Analysis of the YKR079C Mutant Strain" (below).

Phenotypic Analysis of the YKR079C Mutant Strain

Figure 32:
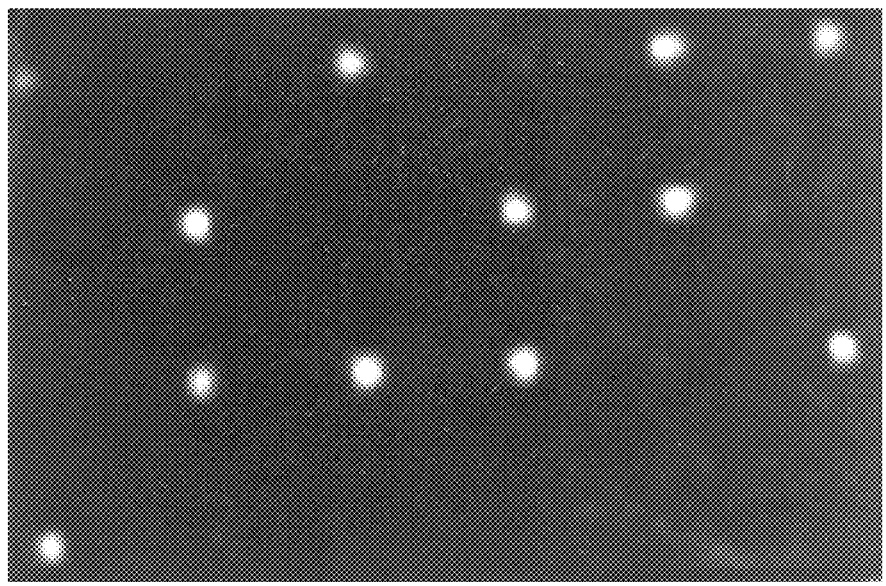
FIG. 32. Lethality of a YKR079C null mutation. A diploid strain containing a heterozygous null mutation of the YKR079C gene (marked by the KanMX gene conferring resistance to the drug G-418) was sporulated and dissected. The four spores of each tetrad were placed in a vertical line (labeled A, B, C and D) and allowed to germinate on rich medium. Six complete tetrads are shown. The observed lethality co-segregated with G-418 resistance, indicating that the lethality was due to the KanMX-marked YKR079C deletion mutation.

Tetrad analysis of the heterozygous ykr079cΔ:KanMX null mutation (R9670) demonstrated that this hypothetical open reading frame not only was in fact a gene, but also that this gene was essential for germination and/or vegetative growth. This was consistent with the inability to construct the YKR079C mutation in the haploid strain. A total of six tetrads were analyzed by dissection. All segregated two live and two dead spores, indicating that there was a single heterozygous lethal mutation in the diploid strain (FIG. 32). All of the twelve living spores were sensitive to G-418, indicating that they had inherited the wild-type allele of the YKR079C gene and that all of the dead spores had inherited the ykr079cΔ::KanMX null allele. Thus, the lethality was linked to the mutant ykr079c allele.

Sequence Comparisons

The YKR079C ORF contains 2,517 bp (FIG. 29), and is predicted to encode a protein of 838 amino acids (FIG. 30). The sequence analysis of the YKR079C encoded protein was performed using the blastp (version 2.0.4, gapped) and the tblastn algorithms at the NCBI web site. The default settings were used. Blastp was used to search the nr and/or the Swiss protein databases; tblastn was used to search the EST database. The predicted YKR079C encoded protein has a Type 1 homolog in *S. pombe,* as well as Type 2 homologs in *C. elegans, S. pombe,* Archaeoglobus, Methanococcus, Pyrococcus, and Methanobacterium (FIG. 31).

EXAMPLE 6

Construction of the YKR083c Mutant Strain and Analysis of Transformants

Construction of the YKR083c Mutant Strain
PCR Conditions

The Chr 11 Round 1a construct PCR and Round 2a construct PCR reactions are described in Example 4. The sequences of the four primers used for the construct PCR of YKR083C are shown in FIG. 33.
Transformation of Yeast The yeast transformation protocol for set 11 was the same as that used to transform set 6 (Example 1). Both haploid (R174) and diploid (R176) strains were transformed. The cultures were harvested at the following densities: R174 O.D.$_{600}$=1.58, and R176 O.D.$_{600}$=1.43. Following the transformations the cells were allowed to recover in YPD at 30° C. for four hours prior to being plated on YPD-G-418 (300 µg/ml) plates. The transformants were colony-purified by restreaking to a second YPD-G-418 plate.

Analysis of Transformants
Whole Cell PCR Analysis

Figure 37:
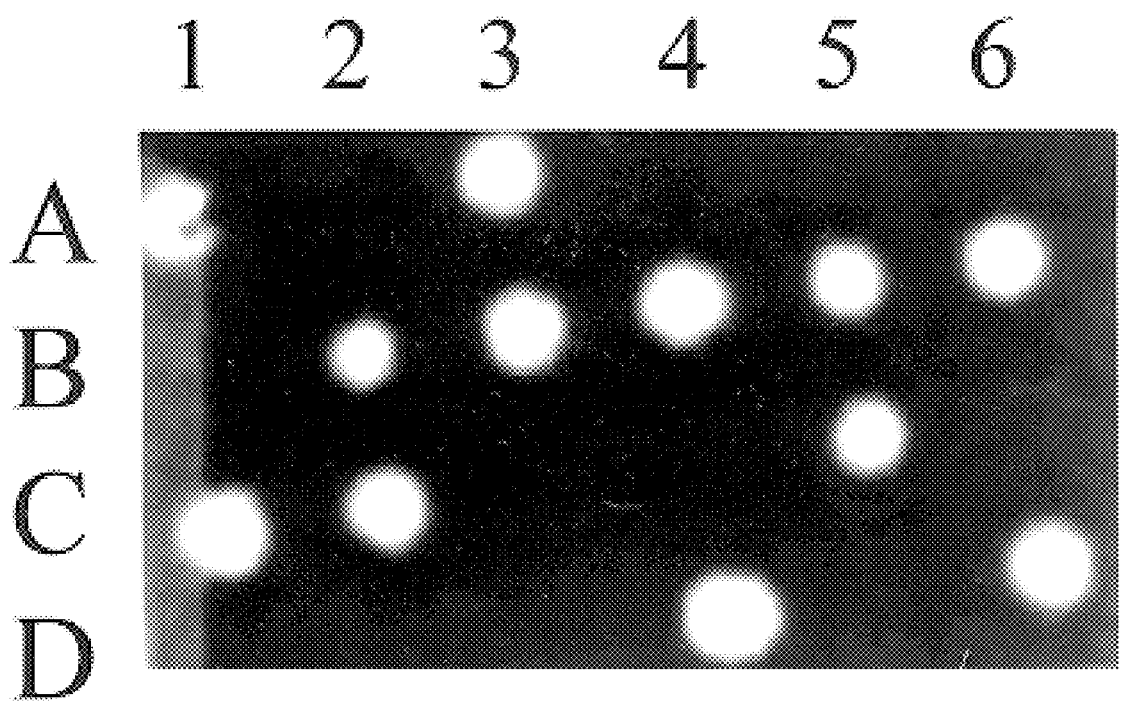
FIG. 37. Lethality of a YKR083C null mutation. A diploid strain containing a heterozygous null mutation of the YKR083C gene (marked by the KanMX gene conferring resistance to the drug G-418) was sporulated and dissected. The four spores of each tetrad were placed in a vertical line (labeled A, B, C and D) and allowed to germinate on rich medium. Six complete tetrads are shown. The observed lethality co-segregated with G-418 resistance, indicating that the lethality was due to the KanMX-marked YKR083C deletion mutation.

Analysis of the set 11 mutations (including YKR083C) was performed by whole cell PCR exactly described in Example 1. The sequences of the six primers used for the analysis of the YKR083C locus (four gene specific, and two marker specific) are shown in FIG. 33. All five analytical PCR primer pairs (A/B, A/KanB, C/D, KanC/D, and A/D) had to give the expected results in order for a mutant to be deemed correct.
Tetrad Analysis Tetrad analysis was performed on the set 11 heterozygous diploids following at least seven days of sporulation at room temperature. The tetrads were digested with Zymolyase and dissected on YPD plates, followed by growth at 30° C. The germinated tetrads were then scored for G-418 resistance, Met auxotrophy, Lys auxotrophy, and mating type by replica-plating to the same seven plates as in Example 1, followed by growth at 30° C. The heterozygous loci (MAT, MET15, and LYS2) showed the expected segregation. The details of the tetrad analysis involving the YKR083C mutation are described in the section "Phenotypic Analysis of the YKR083C Mutant Strain" (below).
Phenotypic Analysis of the YKR083C Mutant Strain Tetrad analysis of the heterozygous ykr083cΔ::KanMX null mutation (R9740) demonstrated that this hypothetical open reading frame not only was in fact a gene, but also that this gene was essential for germination and/or vegetative growth. This was consistent with the inability to construct the YKR083C mutation in the haploid strain. A total of six tetrads were analyzed by dissection. All segregated two live and two dead spores, indicating that there was a single heterozygous lethal mutation in the diploid strain (FIG. 37). All of the twelve living spores were sensitive to G-418, indicating that they had inherited the wild-type allele of the YKR083C gene and that all of the dead spores had inherited the ykr083cΔ::KanMX null allele. Thus, the lethality was linked to the mutant ykr083c allele.
Sequence Comparisons The YKR083C ORF contains 402 bp (FIG. 34), and is predicted to encode a protein of 133 amino acids (FIG. 35).

The sequence analysis of the YKR083C encoded protein was performed using the blastp (version 2.0.4, gapped) and the tblastn algorithms at the NCBI web site. The default settings were used. Blastp was used to search the nr and/or the Swiss protein databases; tblastn was used to search the EST database. The predicted YKR083C encoded protein does not have any sequence comparisons that would indicate either a Type 1 or a Type 2 homolog (FIG. 36). The protein encoded by YKR083C has homology to paramyosin and has an unknown function.

EXAMPLE 7

Screening Assay Using Hybridization Chips to Identify Potential Antifungal Agents A conditional allele of an essential yeast gene is produced as discussed above. The allele may be conditional either for function or expression. For instance, the conditional allele may be a temperature-sensitive allele of the essential gene or the essential gene may be operably linked to an inducible promoter for regulated expression.

The conditional allele is introduced into a yeast strain containing a functional deletion of the essential gene. The yeast strain containing the conditional allele is first grown under the permissive condition, allowing expression of the functional product of the essential gene, to permit the growth of the yeast strain for the assay. Then, the yeast strain is shifted to the nonpermissive condition, in which the product of the essential gene is either not made or is non-functional. The mRNA from the cells is extracted, reverse transcribed and labeled according to standard methods (see Sambrook et al., supra). The resultant cDNA is hybridized to an array of probes, e.g., a hybridization chip, the array is washed free of unhybridized labeled cDNA, the hybridization signal at each unit of the array quantified using a confocal microscope scanner, and the resultant matrix response data stored in digital form.

Hybridization chips may be made by any method known in the art, e.g., as described in U.S. Pat. No. 5,569,588. Unlabeled oligonucleotide hybridization probes complementary to the mRNA transcript of each yeast gene are arrayed on a silicon substrate etched by standard techniques. The probes are of length and sequence to ensure specificity for the corresponding yeast gene, typically about 24–240 nucleotides in length.

The genome expression profile of the yeast strain under the nonpermissive condition is compared to the expression profile of either the same yeast strain grown under permissive conditions or a wildtype yeast strain and identifies those genes which are either induced or repressed by expression of the essential gene. The genes are that are regulated by the expression of the essential gene are then used to screen for antifungal agents.

Wildtype yeast cells or yeast cells grown under permissive conditions are incubated with compounds that are potential antifungal agents. These compounds may be drawn from libraries of natural compounds, combinatorial libraries, or other synthetic compounds. The mRNA from the each of the treated yeast cells is extracted and labeled cDNA is prepared. The cDNA is hybridized to hybridization chips to obtain genome expression profiles for each compound tested. If a genome expression profile of the yeast cell treated with a compound is similar to that of the yeast strain grown under the non-permissive conditions, then the compound is tested for its ability to inhibit wildtype yeast vegetative growth and germination. See U.S. Pat. Nos. 5,569,588 and 5,777,888.

Potential herbicides, insecticides and anti-proliferation agents may be screened in a similar fashion by using plant, insect or mammalian cells, respectively, rather than yeast cells.

EXAMPLE 8

Screening Assay Using the Genome Reporter Matrix to Identify Antifungal Compounds The essential gene of interest is transfected and overexpressed in yeast cells of the Genome Reporter Matrix (GRM). See U.S. Pat. No. 5,569,588. The transcription of all of the genes of the GRM is measured in response to the overexpression and compared to the transcription of these genes in cells that do not overexpress the essential gene. Thus, one can identify a subset of genes that are either induced or repressed by overexpression of the essential gene.

The yeast strains containing the subset of genes regulated by overexpression of the essential gene are then used to screen potential antifungal compounds. The yeast strains are incubated with potential antifungal compounds. If a tagged gene in a particular yeast strain is induced by overexpression of the essential gene, then potential antifungal compounds are screened for the ability to downregulate the tagged gene. Conversely, if a tagged gene is repressed by overexpression of the essential gene, then potential antifungal compounds are screened for the ability to upregulate the tagged gene.

Potential antifungal compounds are screened for the ability to appropriately upregulate and downregulate a number of the genes that whose expression is altered by overexpression of the essential gene. When potential antifungal compounds are identified, these candidate compounds are tested for their ability to inhibit wildtype yeast vegetative growth and germination.

In a similar fashion, potential herbicides may be tested by using a GRM derived from plant cells, potential insecticides may be tested by using a GRM derived from insect cells, and potential anti-proliferation compounds may be tested by using a GRM derived from mammalian cells. Mammalian, insect and plant GRMs are described in U.S. Pat. No. 5,569,588.

References Cited

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method to identify a potential antifungal compound, comprising the steps of
   a) contacting a protein comprising an amino acid sequence encoded by a gene selected from the group consisting of YFR003C, YGR277C, YGR278W, YKR071C, YKR079C, and YKR083C with a compound under conditions effective to promote specific binding between the protein and the compound; and
   b) determining whether the protein bound to the compound;
wherein the compound is a potential antifungal compound if the compound binds to the protein.

2. The method according to claim 1 wherein the protein comprises the mature polypeptide encoded by the essential gene.

3. The method according to claim 1 wherein the protein comprises a functional fragment of the amino acid sequence encoded by the essential gene.

4. The method according to claim 1 wherein the protein is a fusion protein comprising an epitope tag or reporter sequence.

5. The method according to claim 1 wherein the protein is attached to a solid support surface and the compound is in mobile phase.

6. The method according to claim 1 wherein the compound is attached to a solid support surface and the protein is in mobile phase.

7. The method according to claim 1 wherein the compound is a library selected from the group consisting of a combinatorial small organic library, a phage display library and a combinatorial peptide library.

8. The method according to claim 1 wherein said determining is performed by ELISA, RIA or BiaCORE analysis.

9. The method of claim 1 wherein the protein is recombinantly expressed by a cell and is contacted by the compound in situ.

10. The method according to claim 1 wherein said determining is performed by high throughput screening.

11. The method according to claim 1 further comprising the step of determining whether the potential antifungal compound can inhibit yeast germination or vegetative growth.

12. A method to identify genes that an essential gene selected from the group consisting of YFR003C, YGR277C, YGR278W, YKR071C, YKR079C, and YKR083C regulates, comprising the steps of
   a) overexpressing the essential gene in one or more cells; and
   b) identifying genes that are either induced or repressed by overexpression of the essential gene.

13. The method according to claim 12 wherein the cells are of a Genome Reporter Matrix.

14. A method to identify potential antifungal compounds, comprising the steps of
   a) overexpressing an essential gene of yeast selected from the group consisting of YFR003C, YGR277C, YGR278W, YKR071C, YKR079C, and YKR083C in one or more cells;
   b) isolating a subset of genes that are either induced or repressed by overexpression of the essential gene; and
   c) determining the effects of compounds on the down-regulation or up-regulation of any of said subset of genes induced or repressed by overexpression of the essential gene;

wherein a compound is a potential antifungal compound if it downregulates a gene that is induced by overexpression of the essential gene or if it upregulates a gene that is repressed by overexpression of the essential gene.

15. The method according to claim 14 wherein the cells are of a Genome Reporter Matrix.

\* \* \* \* \*